United States Patent
Teitler et al.

(10) Patent No.: US 6,255,089 B1
(45) Date of Patent: Jul. 3, 2001

(54) CONSTITUTIVELY ACTIVATED SEROTONIN RECEPTORS

(75) Inventors: Milt Teitler, Glenmont; Katharine Herrick-Davis, Niskayuna; Christina C. Egan, Guilderland, all of NY (US)

(73) Assignee: Albany Medical College, Albany, NY (US)

( * ) Notice: Subject to any disclaimer, the term of this patent is extended or adjusted under 35 U.S.C. 154(b) by 0 days.

(21) Appl. No.: 09/032,742

(22) Filed: Feb. 27, 1998

Related U.S. Application Data

(60) Provisional application No. 60/061,268, filed on Oct. 7, 1997, and provisional application No. 60/039,465, filed on Feb. 27, 1997.

(51) Int. Cl.⁷ .......................... C07K 14/72; C12N 15/12; G01N 33/53
(52) U.S. Cl. .................. 435/172.3; 435/7.1; 435/7.2; 436/501; 530/350; 536/23.5
(58) Field of Search .......................... 435/7.1, 7.2, 172.3; 436/501; 536/23.5; 530/350

(56) References Cited

PUBLICATIONS

Ren et al. "Constitutively Active Mutants of the alpha2–Adrenergic Receptor". J. Biol. Chem. 268 (22):16483–16487, Aug. 1993.*

Samama et al. "A Mutation–induced Activated State of the beta2–Adrenergic Receptor". J. Biol. Chem. 268(7):4625–4636, Mar. 1993.*

Saudou et al. "Cloning and characterization of a *Drosophila* *tyramine* receptor". EMBO J. 9(11):3611–3617, Aug. 1993.*

* cited by examiner

*Primary Examiner*—John Ulm
(74) *Attorney, Agent, or Firm*—Ann A. Nguyen; Richard P. Burgoon, Jr.

(57) ABSTRACT

Mutations have been discovered in mammalian G protein-coupled serotonin $5-HT_{2A}$ and $5-HT_{2C}$ receptors which render the mutated receptors constitutively active. An alignment methodology based on the highly conserved sixth transmembrane domain has been discovered for the monoamine receptors which accurately predicts the amino acid position in the third intracellular loop which, when mutated, produces constitutive activation of the receptor. Constitutive activation of the G protein-coupled serotonin receptors has been shown by the demonstration of an enhanced affinity and potency for serotonin, by increased basal activity of the second messenger system in the absence of agonist, and by reduction of the basal second messenger activity by inverse agonists.

19 Claims, 45 Drawing Sheets

FIG. 1A

Rat 5-HT$_{2A}$

| | | | | | |
|---|---|---|---|---|---|
| CCCAGGCTAT | GAACCCCTAG | TCTCTCCACA | CTTCATCTGC | TACAACTTCC | GGCTTAGACA | 60
| TGGAAATTCT | TTGTGAAGAC | AATATCTCTC | TGAGCTCAAT | TCCAAACTCC | TTAATGCAAT | 120
| TAGGTGATGG | CCCGAGGCTC | TACCATAATG | ACTTCAACTC | CAGAGATGCT | AACACTTCGG | 180
| AAGCATCGAA | CTGGACAATT | GATGCTGAAA | ACAGAACCAA | CCTCTCCTGT | GAAGGGTACC | 240
| TCCCACCGAC | ATGCCTCTCC | ATTCTTCATC | TCCAGGAAAA | AAACTGGTCT | GCTTTATTGA | 300
| CAACTGTCGT | GATTATTCTC | ACCATTGCTG | GAAATATACT | GGTCATCATG | GCAGTGTCCC | 360
| TAGAAAAAAA | GCTGCAGAAT | GCCACCAACT | ATTTCCTGAT | GTCACTTGCC | ATAGCTGATA | 420
| TGCTGCTGGG | TTTCCTTGTC | ATGCCTGTGT | CCATGTTAAC | CATCCTGTAT | GGGTACCGGT | 480
| GGCCTTTGCC | TAGCAAGCTC | TGTGCGATCT | GGATTTACCT | GGATGTGCTC | TTTTCTACGG | 540
| CATCCATCAT | GCACCTCTGC | GCCATCTCCC | TGGACCGCTA | TGTCGCCATC | CAGAACCCCA | 600
| TTCACCACAG | CCGCTTCAAC | TCCAGAACCA | AGCCTTCCT | GAAAATCATT | GCCGTGTGGA | 660
| CCATATCTGT | AGGTATATCC | ATGCCAATCC | CAGTCTTTGG | ACTACAGGAT | GATTCGAAGG | 720
| TCTTTAAGGA | GGGGAGCTGC | CTGCTTGCCG | ATGACAACTT | TGTTCTCATA | GGCTCTTTTG | 780
| TGGCATTTTT | CATCCCCCTA | ACCATCATGG | TGATCACCTA | CTTCCTGACT | ATCAAGTCAC | 840
| TTCAGAAAGA | AGCCACCTTG | TGTGTGAGTG | ACCTCAGCAC | TCGAGCCAAA | CTAGCCTCCT | 900
| TCAGCTTCCT | CCCTCAGAGT | TCTCTGTCAT | CAGAAAAGCT | CTTCCAACGG | TCCATCCACA | 960
| GAGAGCCAGG | CTCCTACGCA | GGCCGAAGGA | CGATGCAGTC | CATCAGCAAT | GAGCAAAAGG | 1020
| CGTGCAAGGT | GCTGGGCATC | GTGTTCTTCC | TGTTTGTTGT | AATGTGGTGC | CCATTCTTCA | 1080
| TCACCAATAT | CATGGCCGTC | ATCTGCAAAG | AATCCTGCAA | TGAAAATGTC | ATCGGAGCCC | 1140
| TGCTCAATGT | GTTTGTCTGG | ATTGGTTATC | TCTCCTCAGC | TGTCAATCCA | CTGGTATATA | 1200
| CGTTGTTCAA | TAAAACTTAT | AGGTCCGCCT | TCTCAAGGTA | CATTCAGTGT | CAGTACAAGG | 1260
| AAAACAGAAA | GCCACTGCAG | TTAATTTTAG | TGAACACTAT | ACCAGCATTG | GCCTACAAGT | 1320

FIG. 1B

```
CTAGTCAGCT CCAGGTGGGA CAGAAAAAGA ACTCACAGGA AGATGCTGAG CAGACAGTTG   1380
ATGACTGCTC CATGGTTACA CTGGGGAAAC AACAGTCGGA AGAGAATTGT ACAGACAATA   1440
TTGAAACCGT GAATGAAAAG GTTAGCTGTG TGTGATGAAC TGGATGCTAT GGCAATTGCC   1500
CAGGGCATGT GAACAAGGTT ATACCCATGT GTGTGGGGCG GGGATAAGGA GGCTGCAACA   1560
AATTAG                                                             1566
```

FIG. 2

Rat 5-HT$_{2A}$

MEILCEDNISLSSIPNSLMQLGDGPRLYHNDFNSRDANTSEASN

WTIDAENRTNLSCEGYLPPTCLSILHLQEKNWSALLTTVVIILTIAGNILVIMAVSLE

KKLQNATNYFLMSLAIADMLLGFLVMPVSMLTILYGYRWPLPSKLCAIWIYLDVLFST

ASIMHLCAISLDRYVAIQNPIHHSRFNSRTKAFLKIIAVWTISVGISMPIPVFGLQDD

SKVFKEGSCLLADDNFVLIGSFVAFFIPLTIMVITYFLTIKSLQKEATLCVSDLSTRA

KLASFSFLPQSSLSSEKLFQRSIHREPGSYAGRRTMQSISNEQKACKVLGIVFFLFVV

MWCPFFITNIMAVICKESCNENVIGALLNVFVWIGYLSSAVNPLVYTLFNKTYRSAFS

RYIQCQYKENRKPLQLILVNTIPALAYKSSQLQVGQKKNSQEDAEQTVDDCSMVTLGK

QQSEENCTDNIETVNEKVSCV

FIG. 3A

Rat 5-HT$_{2C}$

ORIGIN 23 bp upstream of HindhIII site

| | | | | | |
|---|---|---|---|---|---|
| GGCGCTCTGG | TGCTCACTGA | GGAAGCTTCC | TTAGGTGTAC | CGATCTTAAT | GATTGAGCCC | 60 |
| TTGGAGCAGC | AAGATTGTTA | ATCTTGGTTG | CTCCTTTGGC | CTGTCTATCC | CTTACCTTCC | 120 |
| TATTACATAT | GAACTTTTCT | TCGTTCTGCA | CATCGATTGT | CGTCGGCGTC | GTGGAGATCG | 180 |
| TCGTGGTGCT | CCGGTGGTGG | TCTTCGTCCG | CTTAGAATAG | TGTAGTTAGT | TAGGGGCCTT | 240 |
| CAAAGAAGAA | AGAAGAAGCG | ATTGGCGCGG | AGAGATGCTG | GAGGTGTCAG | TTTCTATGCT | 300 |
| AGAGTAGGGT | AGTGAAACAA | TCCCCAGCCA | AACCTTTCCG | GGGGCGCAG | GTTGCCCACA | 360 |
| GGAGGTCGAC | TTGCCGGCGC | TGTCCTTCGC | GCCGAGCTCC | CTCCATCCTT | CTTTCCGTCT | 420 |
| GCTGAGACGC | AAGGTTGCGG | CGCGCACGCT | GAGCAGCGCA | CTGACTGCCG | CGGGCTCCGC | 480 |
| TGGGCGATTG | CAGCCGAGTC | CGTTTCTCGT | CTAGCTGCCG | CCGCGGCGAC | CTGCCTGGTC | 540 |
| TTCCTCCCGG | ACGCTAGCGG | GTTGTCAACT | ATTACCTGCA | AGCATAGGCC | AACGAACACC | 600 |
| TTCTTTCCAA | ATTAATTGGA | ATGAAACAAT | TCTGTTAACT | TCCTAATTCT | CAGTTTGAAA | 660 |
| CTCTGGTTGC | TTAAGCCTGA | AGCAATCATG | GTGAACCTTG | GCAACGCGGT | GCGCTCGCTC | 720 |
| CTGATGCACC | TAATCGGCCT | ATTGGTTTGG | CAATTCGATA | TTTCCATAAG | TCCAGTAGCA | 780 |
| GCTATAGTAA | CTGACACTTT | TAATTCCTCC | GATGGTGGAC | GCTTGTTTCA | ATTCCCGGAC | 840 |
| GGGGTACAAA | ACTGGCCAGC | ACTTTCAATC | GTCGTGATTA | TAATCATGAC | AATAGGGGGC | 900 |
| AACATTCTTG | TTATCATGGC | AGTAAGCATG | GAGAAGAAAC | TGCACAATGC | AACCAATTAC | 960 |
| TTCTTAATGT | CCCTAGCCAT | TGCTGATATG | CTGGTGGGAC | TACTTGTCAT | GCCCCTGTCC | 1020 |
| CTGCTTGCTA | TTCTTTATGA | TTATGTCTGG | CCTTTACCTA | GATATTTGTG | CCCCGTCTGG | 1080 |
| ATTTCACTAG | ATGTGCTATT | TTCAACTGCG | TCCATCATGC | ACCTCTGCGC | CATATCGCTG | 1140 |
| GACCGGTATG | TAGCAATACG | TAATCCTATT | GAGCATAGCC | GGTTCAATTC | GCGGACTAAG | 1200 |
| GCCATCATGA | AGATTGCCAT | CGTTTGGGCA | ATATCAATAG | GAGTTTCAGT | TCCTATCCCT | 1260 |

FIG. 3B

```
GTGATTGGAC TGAGGGACGA AAGCAAAGTG TTCGTGAATA ACACCACGTG CGTGCTCAAT    1320

GACCCCAACT TCGTTCTCAT CGGGTCCTTC GTGGCATTCT TCATCCCGTT GACGATTATG    1380

GTGATCACCT ACTTCTTAAC GATCTACGTC CTGCGCCGTC AAACTCTGAT GTTACTTCGA    1440

GGTCACACCG AGGAGGAACT GGCTAATATG AGCCTGAACT TCTGAACTG CTGCTGCAAG     1500

AAGAATGGTG GTGAGGAAGA GAACGCTCCG AACCCTAATC CAGATCAGAA ACCACGTCGA    1560

AAGAAGAAAG AAAAGCGTCC CAGAGGCACC ATGCAAGCTA TCAACAACGA AAAGAAAGCT    1620

TCCAAAGTCC TTGGCATTGT ATTCTTTGTG TTTCTGATCA TGTGGTGCCC GTTTTTCATC    1680

ACCAATATCC TGTCGGTTCT TTGTGGGAAG GCCTGTAACC AAAAGCTAAT GGAGAAGCTT    1740

CTCAATGTGT TTGTGTGGAT TGGCTATGTG TGTTCAGGCA TCAATCCTCT GGTGTACACT    1800

CTCTTTAATA AAATTTACCG AAGGGCTTTC TCTAAATATT GCGCTGCGA TTATAAGCCA     1860

GACAAAAAGC CTCCTGTTCG ACAGATTCCT AGGGTTGCTG CCACTGCTTT GTCTGGGAGG    1920

GAGCTCAATG TTAACATTTA TCGGCATACC AATGAACGTG TGGCTAGGAA AGCTAATGAC    1980

CCTGAGCCTG GCATAGAGAT GCAGGTGGAG AACTTAGAGC TGCCAGTCAA CCCCTCTAAT    2040

GTGGTCAGCG AGAGGATTAG TAGTGTGTAA GCGAAGAGCA GCGCAGACTT CCTACAGGAA    2100

AGTTCCTGTA GGAAAGTCCT CCCCACCCCC CGTGATTTTC CTGTGAATCA TAACTAATGT    2160

AAATATTGCT GTGTGACAAG ACAGTGTTTT TATAAATAGC TTTGCAACCC TGTACTTTAC    2220

ATCATGCGTT AATAGTGAGA TTCGGG                                         2246
```

FIG. 4

Rat 5-HT₂C

MVNLGNAVRSLLMHLIGLLVWQFDISISPVAAIVTDTFNSSDGG

RLFQFPDGVQNWPALSIVVIIIMTIGGNILVIMAVSMEKKLHNATNYFLMSLAIADML

VGLLVMPLSLLAILYDYVWPLPRYLCPVWISLDVLFSTASIMHLCAISLDRYVAIRNP

IEHSRFNSRTKAIMKIAIVWAISIGVSVP1PVIGLRDESKVFVNNTTCVLNDPNFVLI

GSFVAFFIPLTIMVITYFLTIYVLRRQTLMLLRGHTEEELANMSLNFLNCCCKKNGGE

EENAPNPNPDQKPRRKKKEKRPRGTMQAINNEKKASKVLGIVFFVFLIMWCPFFITNI

LSVLCGKACNQKLMEKLLNVFVWIGYVCSGINPLVYTLFNKIYRRAFSKYLRCDYKPD

KKPPVRQIPRVAATALSGRELNVNIYRHTNERVARKANDPEPGIEMQVENLELPVNPS

NVVSERISSV

FIG. 5

Rat α₁B-adrenergic

MNPDLDTGHNTSAPAHWGELKDDNFTGPNQTSSNSTLPQLDVTR

AISVGLVLGAFILFAIVGNILVILSVACNRHLRTPTNYFIVNLAIADLLLSFTVLPFS

ATLEVLGYWVLLSFFCDIWAAVDVLCCTASILSLCAISIDRYIGVRYSLQYPTLVTRR

KAILALLSVWVLSTVISIGPLLGWKEPAPNDDKECGVTEEPFYALFSSLGSFYIPLAV

ILVMYCRVYIVAKRTTKNLEAGVMKEMSNDKELTLRIHSKNFHEDTLSSTKAKGHNPR

SSIAVKLFKFSREKKAAKTLGIVVGMFILCWLPFFIALPLGSLFSTLKPPDAVFKVVF

WLGYFNSCLNPIIYPCSSKEFKRAFMRILGCQCRGGRRRRRRRRLGACAYTYRPWTRG

GSLERSQSRKDSLDDSGSCMSGTQRTLPSASPSPGYLGRGTQPPVELCAFPEWKPGAL

LSLPEPPGRRGRLDSGPLFTFKLLGDPESPGTEGDTSNGGCDTTTDLANGQPGFKSNM

PLAPGHF

FIG. 6A

Rat α₁B-adrenergic

| | |
|---|---|
| GGGCGGACTT TAAAATGAAT CCCGATCTGG ACACCGGCCA CAACACATCA GCACCTGCCC | 60 |
| ACTGGGGAGA GTTGAAAGAT GACAACTTCA CTGGCCCCAA CCAGACCTCG AGCAACTCCA | 120 |
| CACTGCCCCA GCTGGACGTC ACCAGGGCCA TCTCTGTGGG CCTGGTGCTG GGCGCCTTCA | 180 |
| TCCTCTTTGC CATCGTGGGC AACATCTTGG TCATCCTGTC GGTGGCCTGC AACCGGCACC | 240 |
| TGCGGACGCC CACCAACTAC TTTATCGTCA ACCTGGCCAT TGCTGACCTG CTGTTGAGTT | 300 |
| TCACAGTACT GCCCTTCTCC GCTACCCTAG AAGTGCTTGG CTACTGGGTG CTGTTGAGTT | 360 |
| TCTTCTGTGA CATCTGGGCA GCGGTAGATG TCCTGTGCTG TACGGCCTCC ATCCTGAGCC | 420 |
| TATGTGCCAT CTCCATTGAC CGCTACATTG GGGTGCGATA CTCTCTGCAG TACCCCACGC | 480 |
| TGGTCACCCG CAGGAAGGCC ATCTTGGCGC TCCTCAGTGT GTGGGTCTTG TCCACGGTCA | 540 |
| TCTCCATCGG GCCTCTCCTT GGATGGAAAG AACCTGCGCC CAATGATGAC AAAGAATGTG | 600 |
| GGGTCACCGA AGAACCCTTC TACGCCCTCT TTTCCTCCCT GGGCTCCTTC TACATCCCGC | 660 |
| TCGCGGTCAT CCTGGTCATG TACTGCCGGG TCTACATCGT GGCCAAGAGG ACCACCAAGA | 720 |
| ATCTGGAGGC GGGAGTCATG AAGGAAATGT CCAACTCCAA GGAGCTGACC CTGAGGATCC | 780 |
| ACTCCAAGAA CTTTCATGAG GACACCCTCA GCAGTACCAA GGCCAAGGGC CACAACCCCA | 840 |
| GGAGTTCCAT AGCTGTCAAA CTTTTTAAGT TCTCCAGGGA AAAGAAAGCA GCCAAAACCT | 900 |
| TGGGCATTGT AGTCGGAATG TTCATCTTAT GTTGGCTCCC CTTCTTCATC GCTCTCCCGC | 960 |
| TTGGCTCCCT GTTCTCCACC CTAAAGCCCC CGGACGCCGT GTTCAAGGTG GTGTTCTGGC | 1020 |
| TGGGCTACTT CAACAGCTGC CTCAATCCCA TCATCTACCC GTGCTCCAGC AAGGAGTTCA | 1080 |
| AGCGCGCCTT CATGCGTATC CTTGGGTGCC AGTGCCGCGG TGGCCGCCGC CGCCGCCGCC | 1140 |
| GTCGCCGTCT AGGCGCGTGC GCTTACACCT ACCGGCCGTG GACCCGCGGC GGCTCGCTGG | 1200 |
| AGAGATCACA GTCGCGGAAG GACTCTCTGG ATGACAGCGG CAGCTGCATG AGCGGCACGC | 1260 |
| AGAGGACCCT GCCCTCGGCG TCGCCCAGCC CGGGCTACCT GGGTCGAGGA ACGCAGCCAC | 1320 |

FIG. 6B

```
CCGTGGAGCT GTGCGCCTTC CCCGAGTGGA AACCCGGGGC GCTGCTCAGC TTGCCAGAGC  1380
CTCCTGGCCG CCGCGGCCGT CTCGACTCTG GGCCACTCTT CACCTTCAAG CTCCTGGGCG  1440
ATCCTGAGAG CCCGGGAACC GAAGGCGACA CCAGCAACGG GGGCTGCGAC ACCACGACCG  1500
ACCTGGCCAA CGGGCAGCCC GGCTTCAAGA GCAACATGCC CCTGGCGCCC GGGCACTTTT  1560
AGGGTCCCTT TTCATCCTCC CCCTCAACAC ACTCACACAT CGGGGTGGGG GAGAACACCA  1620
TCGTAGGGGC GGGAGGGCGC GTGGGGGGAG TGTCAGCCCT AGGTAGACAC AGGGTCGCAA  1680
GGGGACAAGG GGGGAGGGGG GCGGGGAGAG GGGCAGCTGC TTTTCTGGCA GGGGCATGGG  1740
TGCCAGGTAC AGCGAAGAGC TGGGCTGAGC ATGCTGAGAG CGTGGGGGGC CCCCCTAGTG  1800
GTTCCGGGAC TTAAGTCTCT CTCTCTTCTC TCTCTGTATA TACATAAAAT GAGTTCCTCT  1860
ATTCGTATTT ATCTGTGGGT ACACGTGCGT GTGTCTGTTC GGTGTACGTG TGGGCTGCAT  1920
GGGTGTGAGT GTGAGGCCTG CCCGCACGCG CGTGCCGGGG CAGAGCGAGT GCGCCCCCTG  1980
GTGACGTCCA GGTGTGTTGT TTGTCTCTTG ACTTTGTACC TCTCAAGCCC CTCCCTGTTC  2040
TCTAGTCAAT GCTGGCACTT TGATAGGATC GGAAAACAAG TCAGATATTA AAGATCATTT  2100
CTCCTGTG                                                            2108
```

| $\alpha_{1B}$-adrenergic | 5HT$_{2A}$- | 5HT$_{2C}$- |
|---|---|---|
| 285 K | S | A |
| F | I  315 | I  305 |
| S | S | N |
| R | N | N |
| E | E | E |
| 290 K | Q | K |
| K | K  320 | K  310 |
| A | A | A |
| 293 A | C  322 | S  312 |
| K | K | K |
| 295 T | V | V |
| L | L  325 | L  315 |
| G | G | G |
| I | I | I |
| V | V | V |
| 300 V | F | F |
| G | F  330 | F  320 |
| M | L | V |
| F | F | F |
| I | V | L |
| 305 L | V | I |
| C | M  335 | M  325 |
| W | W | W |
| L | C | C |
| P | P | P |
| 310 F | F | F |
| F | F  340 | F  330 |
| I | I | I |
| A | T | T |
| L | N | N |
| 315 P | I | I |
| L | M  345 | L  335 |
| G | A | S |
| S | V | V |
| 319 L | I | L |

Transmembrane Domain VI

↓
c-terminus

FIG. 7

|  | Native 5-HT$_{2A}$ | Cys → Lys Mutant | Cys → Arg Mutant | Cys → Glu Mutant |
|---|---|---|---|---|
| Agonists |  |  |  |  |
| 5-HT | 293±3.0 | 25±2.1* | 10±1.7 | 86±2.9 |
| DOB | 17±1.4 | 2.3±0.3* |  |  |
| DOM | 144±52 | 28±0.3* |  |  |
| Antagonists |  |  |  |  |
| Spiperone | 1.1±0.1 | 2.4±1.0 |  |  |
| Methysergide | 0.3±0.1 | 6.0±0.7* |  |  |
| Ketaserin | 1.0±0.3 | 1.0±0.1 |  |  |
| Mianserin | 3.9±2.2 | 13±2.0* |  |  |

FIG. 14
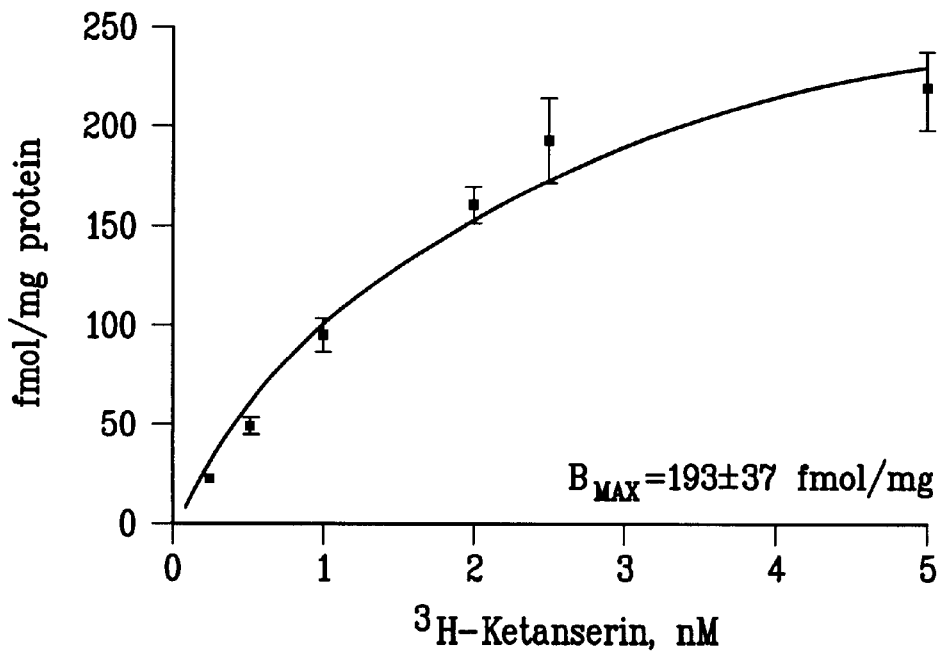
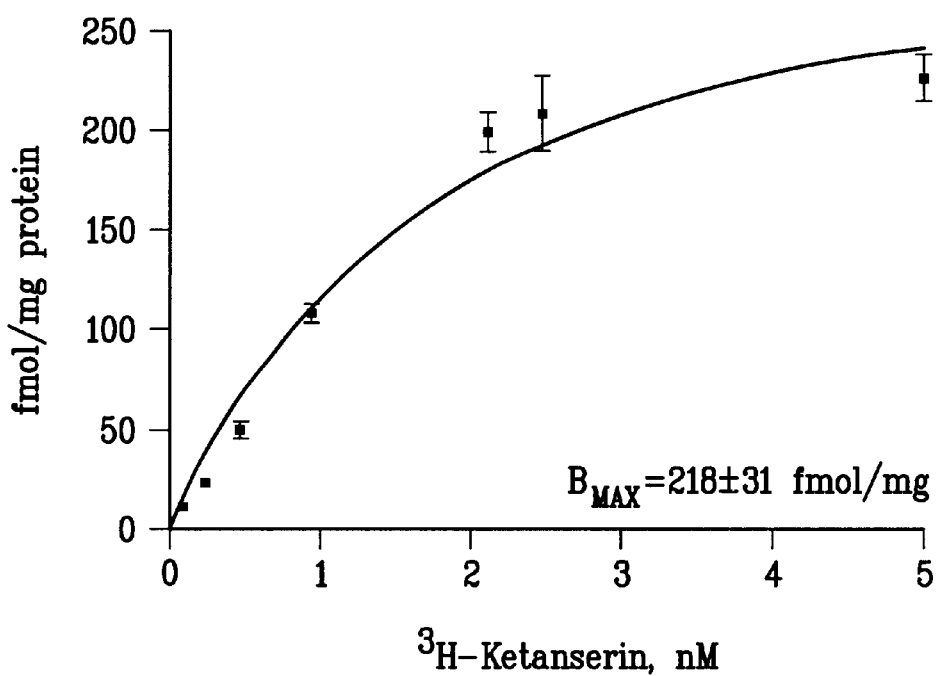

Ki, nM

| Agonists | Native | K Mutant | F Mutant |
|---|---|---|---|
| 5-HT | 203+/−10 | 6.6+/−1.2* | 76+/−7.1* |
| 5-HT | 519+/−104 | 5.8+/−1.1* | ND |
| (+/−)DOB | 256+/−38 | 6.7+/−0.7* | ND |
| Antagonists | | | |
| Mesulergine[a] | 0.6+/−0.1 | 1.2+/−0.1* | 1.3+/−0.2* |
| Mianserin | 1.7+/−0.2 | 3.0+/−0.7** | ND |
| Methysergide | 0.5+/−0.1 | 0.9+/−0.1** | ND |

| 5-HT$_{2C}$ Receptor | 5-HT EC$_{50}$, nM | K$_D$, nM | Bmax, pm/mg |
|---|---|---|---|
| Native | 70+/−18 | 0.6+/−0.1 | 1.5+/−0.2 |
| F Mutant | 28+/−2.5* | 1.3+/−0.2* | 0.6+/−0.1* |
| K Mutant | 2.7+/−1.1* | 1.2+/−0.1* | 1.4+/−0.2 |

FIG.23A

Human 5-HT₂ₐ

| | | | | | |
|---|---|---|---|---|---|
| GAATTCGGGT | GAGCCAGCTC | CGGGAGAACA | GCATGTACAC | CAGCCTCAGT | GTTACAGAGT | 60
| GTGGGTACAT | CAAGGTGAAT | GGTGAGCAGA | AACTATAACC | TGTTAGTCCT | TCTACACCTC | 120
| ATCTGCTACA | AGTTCTGGCT | TAGACATGGA | TATTCTTTGT | GAAGAAAATA | CTTCTTTGAG | 180
| CTCAACTACG | AACTCCCTAA | TGCAATTAAA | TGATGACACC | AGGCTCTACA | GTAATGACTT | 240
| TAACTCTGGA | GAAGCTAACA | CTTCTGATGC | ATTTAACTGG | ACAGTCGACT | CTGAAAATCG | 300
| AACCAACCTT | TCCTGTGAAG | GGTGCCTCTC | ACCGTCGTGT | CTCTCCTTAC | TTCATCTCCA | 360
| GGAAAAAAAC | TGGTCTGCTT | TACTGACAGC | CGTAGTGATT | ATTCTAACTA | TTGCTGGAAA | 420
| CATACTCGTC | ATCATGGCAG | TGTCCCTAGA | GAAAAAGCTG | CAGAATGCCA | CCAACTATTT | 480
| CCTGATGTCA | CTTGCCATAG | CTGATATGCT | GCTGGGTTTC | CTTGTCATGC | CCGTGTCCAT | 540
| GTTAACCATC | CTGTATGGGT | ACCGGTGGCC | TCTGCCGAGC | AAGCTTTGTG | CAGTCTGGAT | 600
| TTACCTGGAC | GTGCTCTTCT | CCACGGCCTC | CATCATGCAC | CTCTGCGCCA | TCTCGCTGGA | 660
| CCGCTACGTC | GCCATCCAGA | ATCCCATCCA | CCACAGCCGC | TTCAACTCCA | GAACTAAGGC | 720
| ATTTCTGAAA | ATCATTGCTG | TTTGGACCAT | ATCAGTAGGT | ATATCCATGC | CAATACCAGT | 780
| CTTTGGGCTA | CAGGACGATT | CGAAGGTCTT | TAAGGAGGGG | AGTTGCTTAC | TCGCCGATGA | 840
| TAACTTTGTC | CTGATCGGCT | CTTTTGTGTC | ATTTTTCATT | CCCTTAACCA | TCATGGTGAT | 900
| CACCTACTTT | CTAACTATCA | AGTCACTCCA | GAAAGAAGCT | ACTTTGTGTG | TAAGTGATCT | 960
| TGGCACACGG | GCCAAATTAG | CTTCTTTCAG | CTTCCTCCCT | CAGAGTTCTT | TGTCTTCAGA | 1020
| AAAGCTCTTC | CAGCGGTCGA | TCCATAGGGA | GCCAGGGTCC | TACACAGGCA | GGAGGACTAT | 1080
| GCAGTCCATC | AGCAATGAGC | AAAAGGCATG | CAAGGTGCTG | GCATCGTCT | TCTTCCTGTT | 1140
| TGTGGTGATG | TGGTGCCCTT | TCTTCATCAC | AAACATCATG | GCCGTCATCT | GCAAAGAGTC | 1200
| CTGCAATGAG | GATGTCATTG | GGGCCCTGCT | CAATGTGTTT | GTTTGGATCG | GTTATCTCTC | 1260
| TTCAGCAGTC | AACCCACTAG | TCTACACACT | GTTCAACAAG | ACCTATAGGT | CAGCCTTTTC | 1320

FIG. 23B

```
ACGGTATATT CAGTGTCAGT ACAAGGAAAA CAAAAAACCA TTGCAGTTAA TTTTAGTGAA   1380
CACAATACCG GCTTTGGCCT ACAAGTCTAG CCAACTTCAA ATGGGACAAA AAAAGAATTC   1440
AAAGCAAGAT GCCAAGACAA CAGATAATGA CTGCTCAATG GTTGCTCTAG GAAAGCAGCA   1500
TTCTGAAGAG GCTTCTAAAG ACAATAGCGA CGGAGTGAAT GAAAAGGTGA GCTGTGTGTG   1560
ATAGGCTAGT TGCCGTGGCA ACTGTGGAAG GCACACTGAG CAAGTTTTCA CCTATCTGGA   1620
AAAAAAAAAT ATGAGATTGG AAAAAATTAG ACAAGTCTAG TGGAACCAAC GATCATATCT   1680
GTATGCCTCA TTTTATTCTG TCAATGAAAA GCGGGGTTCA ATGCTACAAA ATGTGTGCTT   1740
GGAAAATGTT CTGACAGCAT TCAGCTGTG AGCTTTCTGA TACTTATTTA TAACATTGTA    1800
AATGATATGT CTTTAAAATG ATTCACTTTT ATTGTATAAT TATGAAGCCC TAAGTAAATC   1860
TAAATTAACT TCTATTTTCA AGTGGAAACC TTGCTGCTAT GCTGTTCATT GATGACATGG   1920
GATTGAGTTG GTTACCTATT GCCGTAAATA AAAATAGCTA TAAATAGTGA AAATTTTATT   1980
GAATATAATG GCCTCTTAAA AATTATCTTT AAAACTTACT ATGGTATATA TTTTGAAAGG   2040
AGAAAAAAAA AAAGCCACTA AGGTCAGTGT TATAAAATCT GTATTGCTAA GATAATTAAA   2100
TGAAATACTT GACAACATTT TTCATAGATA CCATTTTGAA ATATTCACAA GGTTGCTGGC   2160
ATTTGCTGCA TTTCAAGTTA ATTCTCAGAA GTGAAAAGA CTTCAAATGT TATTCAATAA    2220
CTATTGCTGC TTTCTCTTCT ACTTCTTGTG CTTTACTCTG AATTTCCAGT GTGGTCTTGT   2280
TTAATATTTG TTCCTCTAGG TAAACTAGCA AAAGGATGAT TTAACATTAC CAAATGCCTT   2340
TCTAGCAATT GCTTCTCTAA AACAGCACTA TCGAGGTATT TGGTAACTTG CTGTGAAATG   2400
ACTGCATCAT GCATGCACTC TTTTGAGCAG TAAATGTATA TTGATGTAAC TGTGTCAGGA   2460
TTGAGGATGA ACTCAGGTTT CCGGCTACTG ACAGTGGTAG AGTCCTAGGA CATCTCTGTA   2520
AAAAGCAGGT GACTTTCCTA TGACACTCAT CAGGTAAACT GATGCTTTCA GATCCATCGG   2580
TTTATACTAT TTATTAAAAC CATTCTGCTT GGTTCCACAA TCATCTATTG AGTGTACATT   2640
TATGTGTGAA GCAAATTTCT AGATATGAGA AATATAAAAA TAATTAAAAC AAAATCCTTG   2700
```

FIG. 23C

```
CCTTCAAACG AAATGGCTCG GCCAGGCACG GAGGCTCGTG CATGTAATCC TAGCACTTTG   2760
GGAGGCTGAG ATGGGAGGAT CACTTGAGGC CAAGAGTTTG AGACCAACCT GGGTAACAAA   2820
GTGAGACCTC CCTGTCTCTA CAAAAAAAAT CAAAAAATTA TCTGATCCTT GTGGCACACA   2880
ACTGTGGTCC CAGCTACAGG GGAGGCTGAG ACGCAAGGAT CACTTGAGCC CAGAAGCTCA   2940
AGGCTGCAGT GAGCCAAGTT CACACCACTG CCATTTCCTC CTGGGCAACA GAGTGAGACC   3000
CTATCACCCC GAATTC                                                   3016
```

FIG. 24

```
MDILCEENTSLSSTTNSLMQLNDDTRLYSNDFNSGEANTSDAFN
WTVDSENRTNLSCEGCLSPSCLSLLHLQEKNWSALLTAVVIILTIAGNILVIMAVSLE
KKLQNATNYFLMSLAIADMLLGFLVMPVSMLTILYGRWPLPSKLCAVWIYLDVLFST
ASIMHLCAISLDRYVAIQNPIHHSRFNSRTKAFLKIIAVWTISVGISMPIPVFGLQDD
SKVFKEGSCLLADDNFVLIGSFVSFFIPLTIMVITYFLTIKSLQKEATLCVSDLGTRA
KLASFSFLPQSSLSSEKLFQRSIHREPGSYTGRRTMQSISNEQKACKVLGIVFFLFVV
MWCPFFITNIMAVICKESCNEDVIGALLNVFVWIGYLSSAVNPLVYTLFNKTYRSAFS
RYIQCQYKENKKPLQLILVNTIPALAYKSSQLQMGQKKNSKQDAKTTDNDCSMVALGK
QHSEEASKDNSDGVNEKVSCV
```

FIG. 25A

Human 5-HT₂C

| | | | | | |
|---|---|---|---|---|---|
| GAATTCGGGA | GCGTCCTCAG | ATGCACCGAT | CTTCCCGATA | CTGCCTTTGG | AGCGGCTAGA | 60 |
| TTGCTAGCCT | TGGCTGCTCC | ATTGGCCTGC | CTTGCCCCTT | ACCTGCCGAT | TGCATATGAA | 120 |
| CTCTTCTTCT | GTCTGTACAT | CGTTGTCGTC | GGAGTCGTCG | CGATCGTCGT | GGCGCTCGTG | 180 |
| TGATGGCCTT | CGTCCGTTTA | GAGTAGTGTA | GTTAGTTAGG | GGCCAACGAA | GAAGAAAGAA | 240 |
| GACGCGATTA | GTGCAGAGAT | GCTGGAGGTG | GTCAGTTACT | AAGCTAGAGT | AAGATAGCGG | 300 |
| AGCGAAAAGA | GCCAAACCTA | GCCGGGGGGC | GCACGGTCAC | CCAAAGGAGG | TCGACTCGCC | 360 |
| GGCGCTTCCT | ATCGCGCCGA | GCTCCCTCCA | TTCCTCTCCC | TCCGCCGAGG | CGCGAGGTTG | 420 |
| CGGCGCGCAG | CGCAGCGCAG | CTCAGCGCAC | CGACTGCCGC | GGGCTCCGCT | GGGCGATTGC | 480 |
| AGCCGAGTCC | GTTTCTCGTC | TAGCTGCCGC | CGCGGCGACC | GCTGCCTGGT | CTTCCTCCCG | 540 |
| GACGCTAGTG | GGTTATCAGC | TAACACCCGC | GAGCATCTAT | AACATAGGCC | AACTGACGCC | 600 |
| ATCCTTCAAA | AACAACTGTC | TGGGAAAAAA | AGAATAAAAA | GTAGTGTGAG | AGCAGAAAAC | 660 |
| GTGATTGAAA | CACGACCAAT | CTTTCTTCAG | TGCCAAAGGG | TGGAAAAGAA | AGGATGATAT | 720 |
| GATGAACCTA | GCCTGTTAAT | TTCGTCTTCT | CAATTTTAAA | CTTTGGTTGC | TTAAGACTGA | 780 |
| AGCAATCATG | GTGAACCTGA | GGAATGCGGT | GCATTCATTC | CTTGTGCACC | TAATTGGCCT | 840 |
| ATTGGTTTGG | CAATGTGATA | TTTCTGTGAG | CCCAGTAGCA | GCTATAGTAA | CTGACATTTT | 900 |
| CAATACCTCC | GATGGTGGAC | GCTTCAAATT | CCCAGACGGG | GTACAAAACT | GGCCAGCACT | 960 |
| TCAATCGTC | ATCATAATAA | TCATGACAAT | AGGTGGCAAC | ATCCTTGTGA | TCATGGCAGT | 1020 |
| AAGCATGGAA | AAGAAACTGC | ACAATGCCAC | CAATTACTTC | TTAATGTCCC | TAGCCATTGC | 1080 |
| TGATATGCTA | GTGGGACTAC | TTGTCATGCC | CCTGTCTCTC | CTGGCAATCC | TTTATGATTA | 1140 |
| TGTCTGGCCA | CTACCTAGAT | ATTTGTGCCC | CGTCTGGATT | TCTTTAGATG | TTTTATTTTC | 1200 |
| AACAGCGTCC | ATCATGCACC | TCTGCGCTAT | ATCGCTGGAT | CGGTATGTAG | CAATACGTAA | 1260 |
| TCCTATTGAG | CATAGCCGTT | TCAATTCGCG | GACTAAGGCC | ATCATGAAGA | TTGCTATTGT | 1320 |

FIG. 25B

```
TTGGGCAATT TCTATAGGTG TATCAGTTCC TATCCCTGTG ATTGGACTGA GGGACGAAGA  1380
AAAGGTGTTC GTGAACAACA CGACGTGCGT GCTCAACGAC CCAAATTTCG TTCTTATTGG  1440
GTCCTTCGTA GCTTTCTTCA TACCGCTGAC GATTATGGTG ATTACGTATT GCCTGACCAT  1500
CTACGTTCTG CGCCGACAAG CTTTGATGTT ACTGCACGGC CACACCGAGG AACCGCCTGG  1560
ACTAAGTCTG GATTTCCTGA AGTGCTGCAA GAGGAATACG GCCGAGGAAG AGAACTCTGC  1620
AAACCCTAAC CAAGACCAGA ACGCACGCCG AAGAAAGAAG AAGGAGAGAC GTCCTAGGGG  1680
CACCATGCAG GCTATCAACA ATGAAAGAAA AGCTTCGAAA GTCCTTGGGA TTGTTTTCTT  1740
TGTGTTTCTG ATCATGTGGT GCCCATTTTT CATTACCAAT ATTCTGTCTG TTCTTTGTGA  1800
GAAGTCCTGT AACCAAAAGC TCATGGAAAA GCTTCTGAAT GTGTTTGTTT GGATTGGCTA  1860
TGTTTGTTCA GGAATCAATC CTCTGGTGTA TACTCTGTTC AACAAAATTT ACCGAAGGGC  1920
ATTCTCCAAC TATTTGCGTT GCAATTATAA GGTAGAGAAA AAGCCTCCTG TCAGGCAGAT  1980
TCCAAGAGTT GCCGCCACTG CTTTGTCTGG GAGGGAGCTT AATGTTAACA TTTATCGGCA  2040
TACCAATGAA CCGGTGATCG AGAAAGCCAG TGACAATGAG CCCGGTATAG AGATGCAAGT  2100
TGAGAATTTA GAGTTACCAG TAAATCCCTC CAGTGTGGTT AGCGAAAGGA TTAGCAGTGT  2160
GTGAGAAAGA ACAGCACAGT CTTTTCTACG GTACAAGCTA CATATGTAGG AAAATTTTCT  2220
TCTTTAATTT TTCTGTTGGT CTTAACTAAT GTAAATATTG CTGTCTGAAA AAGTGTTTTT  2280
ACATATAGCT TTGCAACCTT GTACTTTACA ATCATGCCTA CATTAGTGAG ATTTAGGGTT  2340
CTATATTTAC TGTTTATAAT AGGTGGAGAC TAACTTATTT TGATTGTTTG ATGAATAAAA  2400
TGTTTATTTT TGCTCTCCCT CCCTTCTTTC CTTCCTTTTT TCCTTTCTTC CTTCCTTTCT  2460
CTCTTTCTTT TGTGCATATG GCAACGTTCA TGTTCATCTC AGGTGGCATT TGCAGGTGAC  2520
CAGAATGAGG CACATGACAG TGGTTATATT TCAACCACAC CTAAATTAAC AAATTCAGTG  2580
GACATTTGTT CTGGGTTAAC AGTAAATATA CACTTTACAT TCTTGCTCTG CTCATCTACA  2640
CATATAAACA CAGTAAGATA GGTTCTGCTT TCTGATACAT CTGTCAGTGA GTCAGAGGCA  2700
```

FIG. 25C

GAACCTAGTC TTGTTGTTCA TATAGGGGAA TTC                    2733

FIG. 26

Human 5-HT$_{2C}$

MVNLRNAVHSFLVHLIGLLVWQCDISVSPVAAIVTDIFNTSDGG

RFKFPDGVQNWPALSIVIIIMTIGGNILVIMAVSMEKKLHNATNYFLMSLAIADMLV

GLLVMPLSLLAILYDYVWPLPRYLCPVWISLDVLFSTASIMHLCAISLDRYVAIRNPI

EHSRFNSRTKAIMKIAIVWAISIGVSVPIPVIGLRDEEKVFVNNTTCVLNDPNFVLIG

SFVAFFIPLTIMVITYCLTIYVLRRQALMLLHGHTEEPPGLSLDFLKCCKRNTAEEEN

SANPNQDQNARRRKKKERRPRGTMQAINNERKASKVLGIVFFVFLIMWCPFFITNILS

VLCEKSCNQKLMEKLLNVFVWIGYVCSGINPLVYTLFNKIYRRAFSNYLRCNYKVEKK

PPVRQIPRVAATALSGRELNVNIYRHTNEPVIEKASDNEPGIEMQVENLELPVNPSSV

VSERISSV

FIG. 27

Rat 5-HT$_{2A}$ Cysteine -> Lysine Mutant

MEILCEDNISLSSIPNSLMQLGDGPRLYHNDFNSRDANTSEASN

WTIDAENRTNLSCEGYLPPTCLSILHLQEKNWSALLTTVVIILTIAGNILVIMAVSLE

KKLQNATNYFLMSLAIADMLLGFLVMPVSMLTILYGYRWPLPSKLCAIWIYLDVLFST

ASIMHLCAISLDRYVAIQNPIHHSRFNSRTKAFLKIIAVWTISVGISMPIPVFGLQDD

SKVFKEGSCLLADDNFVLIGSFVAFFIPLTIMVITYFLTIKSLQKEATLCVSDLSTRA

KLASFSFLPQSSLSSEKLFQRSIHREPGSYAGRRTMQSISNEQKA<u>K</u>KVLGIVFFLFVV

MWCPFFITNIMAVICKESCNENVIGALLNVFVWIGYLSSAVNPLVYTLFNKTYRSAFS

RYIQCQYKENRKPLQLILVNTIPALAYKSSQLQVGQKKNSQEDAEQTVDDCSMVTLGK

QQSEENCTDNIETVNEKVSCV

FIG. 28A

Rat 5-HT$_{2A}$ Cysteine -> Lysine Mutant

```
CCCAGGCTAT GAACCCCTAG TCTCTCCACA CTTCATCTGC TACAACTTCC GGCTTAGACA    60
TGGAAATTCT TTGTGAAGAC AATATCTCTC TGAGCTCAAT TCCAAACTCC TTAATGCAAT   120
TAGGTGATGG CCCGAGGCTC TACCATAATG ACTTCAACTC AGAGATGCT AACACTTCGG   180
AAGCATCGAA CTGGACAATT GATGCTGAAA ACAGAACCAA CCTCTCCTGT GAAGGGTACC   240
TCCCACCGAC ATGCCTCTCC ATTCTTCATC TCCAGGAAAA AAACTGGTCT GCTTTATTGA   300
CAACTGTCGT GATTATTCTC ACCATTGCTG GAAATATACT GGTCATCATG GCAGTGTCCC   360
TAGAAAAAAA GCTGCAGAAT GCCACCAACT ATTTCCTGAT GTCACTTGCC ATAGCTGATA   420
TGCTGCTGGG TTTCCTTGTC ATGCCTGTGT CCATGTTAAC CATCCTGTAT GGGTACCGGT   480
GGCCTTTGCC TAGCAAGCTC TGTGCGATCT GGATTTACCT GGATGTGCTC TTTTCTACGG   540
CATCCATCAT GCACCTCTGC GCCATCTCCC TGGACCGCTA TGTCGCCATC CAGAACCCCA   600
TTCACCACAG CCGCTTCAAC TCCAGAACCA AAGCCTTCCT GAAAATCATT GCCGTGTGGA   660
CCATATCTGT AGGTATATCC ATGCCAATCC CAGTCTTTGG ACTACAGGAT GATTCGAAGG   720
TCTTTAAGGA GGGGAGCTGC CTGCTTGCCG ATGACAACTT TGTTCTCATA GGCTCTTTTG   780
TGGCATTTTT CATCCCCCTA ACCATCATGG TGATCACCTA CTTCCTGACT ATCAAGTCAC   840
TTCAGAAAGA AGCCACCTTG TGTGTGAGTG ACCTCAGCAC TCGAGCCAAA CTAGCCTCCT   900
TCAGCTTCCT CCCTCAGAGT TCTCTGTCAT CAGAAAAGCT CTTCCAACGG TCCATCCACA   960
```
                              Start C322K primer ———▼
```
GAGAGCCAGG CTCCTACGCA GGCCGAAGGA CGATGCAGTC CATCAGCAAT GAGCAAAAGG  1020
```
                                    ┌——— End C322K primer
```
CGAAGAAGGT GCTGGGCATC GTGTTCTTCC TGTTTGTTGT AATGTGGTGC CCATTCTTCA  1080
TCACCAATAT CATGGCCGTC ATCTGCAAAG AATCCTGCAA TGAAAATGTC ATCGGAGCCC  1140
TGCTCAATGT GTTTGTCTGG ATTGGTTATC TCTCCTCAGC TGTCAATCCA CTGGTATATA  1200
CGTTGTTCAA TAAAACTTAT AGGTCCGCCT TCTCAAGGTA CATTCAGTGT CAGTACAAGG  1260
AAAACAGAAA GCCACTGCAG TTAATTTTAG TGAACACTAT ACCAGCATTG GCCTACAAGT  1320
```

FIG. 28B

```
CTAGTCAGCT CCAGGTGGGA CAGAAAAAGA ACTCACAGGA AGATGCTGAG CAGACAGTTG   1380

ATGACTGCTC CATGGTTACA CTGGGGAAAC AACAGTCGGA AGAGAATTGT ACAGACAATA   1440

TTGAAACCGT GAATGAAAAG GTTAGCTGTG TGTGATGAAC TGGATGCTAT GGCAATTGCC   1500

CAGGGCATGT GAACAAGGTT ATACCCATGT GTGTGGGGCG GGGATAAGGA GGCTGCAACA   1560

AATTAG                                                             1566
```

FIG. 29A

Rat 5-HT₂ₐ Cysteine -> Lysine Mutant with Restriction Site

```
CCCAGGCTAT GAACCCCTAG TCTCTCCACA CTTCATCTGC TACAACTTCC GGCTTAGACA    60
TGGAAATTCT TGTGAAGAC AATATCTCTC TGAGCTCAAT TCCAAACTCC TTAATGCAAT   120
TAGGTGATGG CCCGAGGCTC TACCATAATG ACTTCAACTC CAGAGATGCT AACACTTCGG   180
AAGCATCGAA CTGGACAATT GATGCTGAAA ACAGAACCAA CCTCTCCTGT GAAGGGTACC   240
TCCCACCGAC ATGCCTCTCC ATTCTTCATC TCCAGGAAAA AAACTGGTCT GCTTTATTGA   300
CAACTGTCGT GATTATTCTC ACCATTGCTG GAAATATACT GGTCATCATG GCAGTGTCCC   360
TAGAAAAAAA GCTGCAGAAT GCCACCAACT ATTTCCTGAT GTCACTTGCC ATAGCTGATA   420
TGCTGCTGGG TTTCCTTGTC ATGCCTGTGT CCATGTTAAC CATCCTGTAT GGGTACCGGT   480
GGCCTTTGCC TAGCAAGCTC TGTGCGATCT GGATTTACCT GGATGTGCTC TTTTCTACGG   540
CATCCATCAT GCACCTCTGC GCCATCTCCC TGGACCGCTA TGTCGCCATC CAGAACCCCA   600
TTCACCACAG CCGCTTCAAC TCCAGAACCA AAGCCTTCCT GAAAATCATT GCCGTGTGGA   660
CCATATCTGT AGGTATATCC ATGCCAATCC CAGTCTTTGG ACTACAGGAT GATTCGAAGG   720
TCTTTAAGGA GGGGAGCTGC CTGCTTGCCG ATGACAACTT TGTTCTCATA GGCTCTTTTG   780
TGGCATTTTT CATCCCCCTA ACCATCATGG TGATCACCTA CTTCCTGACT ATCAAGTCAC   840
TTCAGAAAGA AGCCACCTTG TGTGTGAGTG ACCTCAGCAC TCGAGCCAAA CTAGCCTCCT   900
TCAGCTTCCT CCCTCAGAGT TCTCTGTCAT CAGAAAAGCT CTTCCAACGG TCCATCCACA   960
                             Start C322K primer
GAGAGCCAGG CTCCTACGCA GGCCGAAGGA CGATGCAGTC CATCAGCAAT GAGCAAAAGG  1020
                                End C322K primer
CGAAGAAAGT ACTGGGCATC GTGTTCTTCC TGTTTGTTGT AATGTGGTGC CCATTCTTCA  1080
  ↑    ↑                Mutations to create ScaI site
TCACCAATAT CATGGCCGTC ATCTGCAAAG AATCCTGCAA TGAAAATGTC ATCGGAGCCC  1140
TGCTCAATGT GTTTGTCTGG ATTGGTTATC TCTCCTCAGC TGTCAATCCA CTGGTATATA  1200
CGTTGTTCAA TAAAACTTAT AGGTCCGCCT TCTCAAGGTA CATTCAGTGT CAGTACAAGG  1260
AAAACAGAAA GCCACTGCAG TTAATTTTAG TGAACACTAT ACCAGCATTG GCCTACAAGT  1320
```

FIG. 29B

```
CTAGTCAGCT CCAGGTGGGA CAGAAAAAGA ACTCACAGGA AGATGCTGAG CAGACAGTTG   1380
ATGACTGCTC CATGGTTACA CTGGGGAAAC AACAGTCGGA AGAGAATTGT ACAGACAATA   1440
TTGAAACCGT GAATGAAAAG GTTAGCTGTG TGTGATGAAC TGGATGCTAT GGCAATTGCC   1500
CAGGGCATGT GAACAAGGTT ATACCCATGT GTGTGGGGCG GGGATAAGGA GGCTGCAACA   1560
AATTAG                                                              1566
```

FIG. 30

Rat 5-HT$_{2A}$ Cysteine -> Arginine Mutant

MEILCEDNISLSSIPNSLMQLGDGPRLYHNDFNSRDANTSEASN

WTIDAENRTNLSCEGYLPPTCLSILHLQEKNWSALLTTVVIILTIAGNILVIMAVSLE

KKLQNATNYFLMSLAIADMLLGFLVMPVSMLTILYGYRWPLPSKLCAIWIYLDVLFST

ASIMHLCAISLDRYVAIQNPIHHSRFNSRTKAFLKIIAVWTISVGISMPIPVFGLQDD

SKVFKEGSCLLADDNFVLIGSFVAFFIPLTIMVITYFLTIKSLQKEATLCVSDLSTRA

KLASFSFLPQSSLSSEKLFQRSIHREPGSYAGRRTMQSISNEQKARKVLGIVFFLFVV

MWCPFFITNIMAVICKESCNENVIGALLNVFVWIGYLSSAVNPLVYTLFNKTYRSAFS

RYIQCQYKENRKPLQLILVNTIPALAYKSSQLQVGQKKNSQEDAEQTVDDCSMVTLGK

QQSEENCTDNIETVNEKVSCV

FIG. 31A

Rat 5HT₂ₐ Cysteine -> Arginine Mutant

```
CCCAGGCTAT GAACCCCTAG TCTCTCCACA CTTCATCTGC TACAACTTCC GGCTTAGACA   60
TGGAAATTCT TTGTGAAGAC AATATCTCTC TGAGCTCAAT TCCAAACTCC TTAATGCAAT  120
TAGGTGATGG CCCGAGGCTC TACCATAATG ACTTCAACTC CAGAGATGCT AACACTTCGG  180
AAGCATCGAA CTGGACAATT GATGCTGAAA ACAGAACCAA CCTCTCCTGT GAAGGGTACC  240
TCCCACCGAC ATGCCTCTCC ATTCTTCATC TCCAGGAAAA AAACTGGTCT GCTTTATTGA  300
CAACTGTCGT GATTATTCTC ACCATTGCTG GAAATATACT GGTCATCATG GCAGTGTCCC  360
TAGAAAAAAA GCTGCAGAAT GCCACCAACT ATTTCCTGAT GTCACTTGCC ATAGCTGATA  420
TGCTGCTGGG TTTCCTTGTC ATGCCTGTGT CCATGTTAAC CATCCTGTAT GGGTACCGGT  480
GGCCTTTGCC TAGCAAGCTC TGTGCGATCT GGATTTACCT GGATGTGCTC TTTTCTACGG  540
CATCCATCAT GCACCTCTGC GCCATCTCCC TGGACCGCTA TGTCGCCATC CAGAACCCCA  600
TTCACCACAG CCGCTTCAAC TCCAGAACCA AAGCCTTCCT GAAAATCATT GCCGTGTGGA  660
CCATATCTGT AGGTATATCC ATGCCAATCC CAGTCTTTGG ACTACAGGAT GATTCGAAGG  720
TCTTTAAGGA GGGGAGCTGC CTGCTTGCCG ATGACAACTT TGTTCTCATA GGCTCTTTTG  780
TGGCATTTTT CATCCCCCTA ACCATCATGG TGATCACCTA CTTCCTGACT ATCAAGTCAC  840
TTCAGAAAGA AGCCACCTTG TGTGTGAGTG ACCTCAGCAC TCGAGCCAAA CTAGCCTCCT  900
TCAGCTTCCT CCCTCAGAGT TCTCTGTCAT CAGAAAAGCT CTTCCAACGG TCCATCCACA  960
                                Start C322R primer
GAGAGCCAGG CTCCTACGCA GGCCGAAGGA CGATGCAGTC CATCAGCAAT GAGCAAAAGG 1020
                                    End C322R primer
CGAGGAAGGT GCTGGGCATC GTGTTCTTCC TGTTTGTTGT AATGTGGTGC CCATTCTTCA 1080
TCACCAATAT CATGGCCGTC ATCTGCAAAG AATCCTGCAA TGAAAATGTC ATCGGAGCCC 1140
TGCTCAATGT GTTTGTCTGG ATTGGTTATC TCTCCTCAGC TGTCAATCCA CTGGTATATA 1200
CGTTGTTCAA TAAAACTTAT AGGTCCGCCT TCTCAAGGTA CATTCAGTGT CAGTACAAGG 1260
AAAACAGAAA GCCACTGCAG TTAATTTTAG TGAACACTAT ACCAGCATTG GCCTACAAGT 1320
```

FIG. 31B

```
CTAGTCAGCT CCAGGTGGGA CAGAAAAAGA ACTCACAGGA AGATGCTGAG CAGACAGTTG   1380

ATGACTGCTC CATGGTTACA CTGGGGAAAC AACAGTCGGA AGAGAATTGT ACAGACAATA   1440

TTGAAACCGT GAATGAAAAG GTTAGCTGTG TGTGATGAAC TGGATGCTAT GGCAATTGCC   1500

CAGGGCATGT GAACAAGGTT ATACCCATGT GTGTGGGGCG GGGATAAGGA GGCTGCAACA   1560

AATTAG                                                              1566
```

FIG. 32A

Rat 5HT$_{2A}$ Cysteine -> Arginine Mutant with Restriction Site

```
CCCAGGCTAT GAACCCCTAG TCTCTCCACA CTTCATCTGC TACAACTTCC GGCTTAGACA    60
TGGAAATTCT TTGTGAAGAC AATATCTCTC TGAGCTCAAT TCCAAACTCC TTAATGCAAT   120
TAGGTGATGG CCCGAGGCTC TACCATAATG ACTTCAACTC AGAGATGCT  AACACTTCGG   180
AAGCATCGAA CTGGACAATT GATGCTGAAA ACAGAACCAA CCTCTCCTGT GAAGGGTACC   240
TCCCACCGAC ATGCCTCTCC ATTCTTCATC TCCAGGAAAA AAACTGGTCT GCTTTATTGA   300
CAACTGTCGT GATTATTCTC ACCATTGCTG GAAATATACT GGTCATCATG GCAGTGTCCC   360
TAGAAAAAAA GCTGCAGAAT GCCACCAACT ATTTCCTGAT GTCACTTGCC ATAGCTGATA   420
TGCTGCTGGG TTTCCTTGTC ATGCCTGTGT CCATGTTAAC CATCCTGTAT GGGTACCGGT   480
GGCCTTTGCC TAGCAAGCTC TGTGCGATCT GGATTTACCT GGATGTGCTC TTTTCTACGG   540
CATCCATCAT GCACCTCTGC GCCATCTCCC TGGACCGCTA TGTCGCCATC CAGAACCCCA   600
TTCACCACAG CCGCTTCAAC TCCAGAACCA AGCCTTCCT  GAAAATCATT GCCGTGTGGA   660
CCATATCTGT AGGTATATCC ATGCCAATCC CAGTCTTTGG ACTACAGGAT GATTCGAAGG   720
TCTTTAAGGA GGGGAGCTGC CTGCTTGCCG ATGACAACTT TGTTCTCATA GGCTCTTTTG   780
TGGCATTTTT CATCCCCCTA ACCATCATGG TGATCACCTA CTTCCTGACT ATCAAGTCAC   840
TTCAGAAAGA AGCCACCTTG TGTGTGAGTG ACCTCAGCAC TCGAGCCAAA CTAGCCTCCT   900
TCAGCTTCCT CCCTCAGAGT TCTCTGTCAT CAGAAAAGCT CTTCCAACGG TCCATCCACA   960
                                       Start C322R primer ─┐
GAGAGCCAGG CTCCTACGCA GGCCGAAGGA CGATGCAGTC CATCAGCAAT GAGCAAAAGG  1020
                                 ┌─────────End C322R primer
CGAGGAAGGT GCTGGGCATC GTGTTCTTCC TGTTTGTTGT AATGTGGTGC CCATTCTTCA  1080
TCACCAATAT CATGGCCGTC ATCTGCAAAG AATCCTGCAA TGAAAATGTC ATCGGAGCCC  1140
TGCTCAATGT GTTTGTCTGG ATTGGTTATC TCTCCTCAGC TGTCAATCCA CTGGTATATA  1200
CGTTGTTCAA TAAAACTTAT AGGTCCGCCT TCTCAAGGTA CATTCAGTGT CAGTACAAGG  1260
AAAACAGAAA GCCACTGCAG TTAATTTTAG TGAACACTAT ACCAGCATTG GCCTACAAGT  1320
```

FIG. 32B

```
CTAGTCAGCT CCAGGTGGGA CAGAAAAAGA ACTCACAGGA AGATGCTGAG CAGACAGTTG   1380
ATGACTGCTC CATGGTTACA CTGGGGAAAC AACAGTCGGA AGAGAATTGT ACAGACAATA   1440
TTGAAACCGT GAATGAAAAG GTTAGCTGTG TGTGATGAAC TGGATGCTAT GGCAATTGCC   1500
```
CAGGGCATGT GAACAAGGTT ATACCCATGT GTGTGGGGCG GGGATAAGGA GGCTGCAACA   1560
AATTAG                                                              1566

FIG. 33

Rat 5HT₂ₐ Cysteine -> Glutamic Acid Mutant

MEILCEDNISLSSIPNSLMQLGDGPRLYHNDFNSRDANTSEASN

WTIDAENRTNLSCEGYLPPTCLSILHLQEKNWSALLTTVVIILTIAGNILVIMAVSLE

KKLQNATNYFLMSLAIADMLLGFLVMPVSMLTILYGYRWPLPSKLCAIWIYLDVLFST

ASIMHLCAISLDRYVAIQNPIHHSRFNSRTKAFLKIIAVWTISVGISMPIPVFGLQDD

SKVFKEGSCLLADDNFVLIGSFVAFFIPLTIMVITYFLTIKSLQKEATLCVSDLSTRA

KLASFSFLPQSSLSSEKLFQRSIHREPGSYAGRRTMQSISNEQKAEKVLGIVFFLFVV

MWCPFFITNIMAVICKESCNENVIGALLNVFVWIGYLSSAVNPLVYTLFNKTYRSAFS

RYIQCQYKENRKPLQLILVNTIPALAYKSSQLQVGQKKNSQEDAEQTVDDCSMVTLGK

QQSEENCTDNIETVNEKVSCV

FIG. 34A

Rat 5HT$_{2A}$ Cysteine -> Glutamic Acid Mutant

```
CCCAGGCTAT GAACCCCTAG TCTCTCCACA CTTCATCTGC TACAACTTCC GGCTTAGACA    60
TGGAAATTCT TTGTGAAGAC AATATCTCTC TGAGCTCAAT TCCAAACTCC TTAATGCAAT   120
TAGGTGATGG CCCGAGGCTC TACCATAATG ACTTCAACTC CAGAGATGCT AACACTTCGG   180
AAGCATCGAA CTGGACAATT GATGCTGAAA ACAGAACCAA CCTCTCCTGT GAAGGGTACC   240
TCCCACCGAC ATGCCTCTCC ATTCTTCATC TCCAGGAAAA AAACTGGTCT GCTTTATTGA   300
CAACTGTCGT GATTATTCTC ACCATTGCTG GAAATATACT GGTCATCATG GCAGTGTCCC   360
TAGAAAAAAA GCTGCAGAAT GCCACCAACT ATTTCCTGAT GTCACTTGCC ATAGCTGATA   420
TGCTGCTGGG TTTCCTTGTC ATGCCTGTGT CCATGTTAAC CATCCTGTAT GGGTACCGGT   480
GGCCTTTGCC TAGCAAGCTC TGTGCGATCT GGATTTACCT GGATGTGCTC TTTTCTACGG   540
CATCCATCAT GCACCTCTGC GCCATCTCCC TGGACCGCTA TGTCGCCATC CAGAACCCCA   600
TTCACCACAG CCGCTTCAAC TCCAGAACCA AGCCTTCCT GAAAATCATT GCCGTGTGGA   660
CCATATCTGT AGGTATATCC ATGCCAATCC CAGTCTTTGG ACTACAGGAT GATTCGAAGG   720
TCTTTAAGGA GGGGAGCTGC CTGCTTGCCG ATGACAACTT TGTTCTCATA GGCTCTTTTG   780
TGGCATTTTT CATCCCCCTA ACCATCATGG TGATCACCTA CTTCCTGACT ATCAAGTCAC   840
TTCAGAAAGA AGCCACCTTG TGTGTGAGTG ACCTCAGCAC TCGAGCCAAA CTAGCCTCCT   900
TCAGCTTCCT CCCTCAGAGT TCTCTGTCAT CAGAAAAGCT CTTCCAACGG TCCATCCACA   960
                                        Start C322E primer
GAGAGCCAGG CTCCTACGCA GGCCGAAGGA CGATGCAGTC CATCAGCAAT GAGCAAAAGG  1020
                                              End C322E primer
CGGAGAAGGT GCTGGGCATC GTGTTCTTCC TGTTTGTTGT AATGTGGTGC CCATTCTTCA  1080
TCACCAATAT CATGGCCGTC ATCTGCAAAG AATCCTGCAA TGAAAATGTC ATCGGAGCCC  1140
TGCTCAATGT GTTTGTCTGG ATTGGTTATC TCTCCTCAGC TGTCAATCCA CTGGTATATA  1200
CGTTGTTCAA TAAAACTTAT AGGTCCGCCT TCTCAAGGTA CATTCAGTGT CAGTACAAGG  1260
AAAACAGAAA GCCACTGCAG TTAATTTTAG TGAACACTAT ACCAGCATTG GCCTACAAGT  1320
```

FIG. 34B

```
CTAGTCAGCT CCAGGTGGGA CAGAAAAAGA ACTCACAGGA AGATGCTGAG CAGACAGTTG  1380

ATGACTGCTC CATGGTTACA CTGGGGAAAC AACAGTCGGA AGAGAATTGT ACAGACAATA  1440

TTGAAACCGT GAATGAAAAG GTTAGCTGTG TGTGATGAAC TGGATGCTAT GGCAATTGCC  1500

CAGGGCATGT GAACAAGGTT ATACCCATGT GTGTGGGGCG GGATAAGGA GGCTGCAACA   1560

AATTAG                                                             1566
```

FIG. 35A

Rat 5HT₂ₐ Cysteine -> Glutamic Acid Mutant with Restriction Site

```
CCCAGGCTAT GAACCCCTAG TCTCTCCACA CTTCATCTGC TACAACTTCC GGCTTAGACA    60
TGGAAATTCT TTGTGAAGAC AATATCTCTC TGAGCTCAAT TCCAAACTCC TTAATGCAAT   120
TAGGTGATGG CCCGAGGCTC TACCATAATG ACTTCAACTC CAGAGATGCT AACACTTCGG   180
AAGCATCGAA CTGGACAATT GATGCTGAAA ACAGAACCAA CCTCTCCTGT GAAGGGTACC   240
TCCCACCGAC ATGCCTCTCC ATTCTTCATC TCCAGGAAAA AAACTGGTCT GCTTTATTGA   300
CAACTGTCGT GATTATTCTC ACCATTGCTG AAATATACT GGTCATCATG GCAGTGTCCC   360
TAGAAAAAAA GCTGCAGAAT GCCACCAACT ATTTCCTGAT GTCACTTGCC ATAGCTGATA   420
TGCTGCTGGG TTTCCTTGTC ATGCCTGTGT CCATGTTAAC CATCCTGTAT GGGTACCGGT   480
GGCCTTTGCC TAGCAAGCTC TGTGCGATCT GGATTTACCT GGATGTGCTC TTTTCTACGG   540
CATCCATCAT GCACCTCTGC GCCATCCCC TGGACCGCTA TGTCGCCATC CAGAACCCCA   600
TTCACCACAG CCGCTTCAAC TCCAGAACCA AAGCCTTCCT GAAAATCATT GCCGTGTGGA   660
CCATATCTGT AGGTATATCC ATGCCAATCC CAGTCTTTGG ACTACAGGAT GATTCGAAGG   720
TCTTTAAGGA GGGGAGCTGC CTGCTTGCCG ATGACAACTT TGTTCTCATA GGCTCTTTTG   780
TGGCATTTTT CATCCCCCTA ACCATCATGG TGATCACCTA CTTCCTGACT ATCAAGTCAC   840
TTCAGAAAGA AGCCACCTTG TGTGTGAGTG ACCTCAGCAC TCGAGCCAAA CTAGCCTCCT   900
TCAGCTTCCT CCCTCAGAGT TCTCTGTCAT CAGAAAAGCT CTTCCAACGG TCCATCCACA   960
                          Start C322E primer
GAGAGCCAGG CTCCTACGCA GGCCGAAGGA CGATGCAGTC CATCAGCAAT GAGCAAAAGG  1020
                                        End C322E primer
CGGAGAAGGT ACTGGGCATC GTGTTCTTCC TGTTTGTTGT AATGTGGTGC CCATTCTTCA  1080
         ▲ ──Mutation to create RsaI site
TCACCAATAT CATGGCCGTC ATCTGCAAAG AATCCTGCAA TGAAAATGTC ATCGGAGCCC  1140
TGCTCAATGT GTTTGTCTGG ATTGGTTATC TCTCCTCAGC TGTCAATCCA CTGGTATATA  1200
CGTTGTTCAA TAAAACTTAT AGGTCCGCCT TCTCAAGGTA CATTCAGTGT CAGTACAAGG  1260
AAAACAGAAA GCCACTGCAG TTAATTTTAG TGAACACTAT ACCAGCATTG GCCTACAAGT  1320
```

FIG. 35B

```
CTAGTCAGCT CCAGGTGGGA CAGAAAAAGA ACTCACAGGA AGATGCTGAG CAGACAGTTG  1380
ATGACTGCTC CATGGTTACA CTGGGGAAAC AACAGTCGGA AGAGAATTGT ACAGACAATA  1440
TTGAAACCGT GAATGAAAAG GTTAGCTGTG TGTGATGAAC TGGATGCTAT GGCAATTGCC  1500
CAGGGCATGT GAACAAGGTT ATACCCATGT GTGTGGGGCG GGGATAAGGA GGCTGCAACA  1560
AATTAG                                                             1566
```

FIG. 36

Rat 5-HT$_{2C}$ Serine -> Lysine Mutant

MVNLGNAVRSLLMHLIGLLVWQFDISISPVAAIVTDTFNSSDGG

RLFQFPDGVQNWPALSIVVIIMTIGGNILVIMAVSMEKKLHNATNYFLMSLAIADML

VGLLVMPLSLLAILYDYVWPLPRYLCPVWISLDVLFSTASIMHLCAISLDRYVAIRNP

IEHSRFNSRTKAIMKIAIVWAISIGVSVPIPVIGLRDESKVFVNNTTCVLNDPNFVLI

GSFVAFFIPLTIMVITYFLTIYVLRRQTLMLLRGHTEEELANMSLNFLNCCCKKNGGE

EENAPNPNPDQKPRRKKKEKRPRGTMQAINNEKKAKKVLGIVFFVFLIMWCPFFITNI

LSVLCGKACNQKLMEKLLNVFVWIGYVCSGINPLVYTLFNKIYRRAFSKYLRCDYKPD

KKPPVRQIPRVAATALSGRELNVNIYRHTNERVARKANDPEPGIEMQVENLELPVNPS

NVVSERISSV

FIG. 37A

Rat 5HT$_{2C}$ Serine -> Lysine Mutant

ORIGIN    23 bp upstream of HindIII site

| | | | | | |
|---|---|---|---|---|---|
| GGCGCTCTGG | TGCTCACTGA | GGAAGCTTCC | TTAGGTGTAC | CGATCTTAAT | GATTGAGCCC | 60 |
| TTGGAGCAGC | AAGATTGTTA | ATCTTGGTTG | CTCCTTTGGC | CTGTCTATCC | CTTACCTTCC | 120 |
| TATTACATAT | GAACTTTTCT | TCGTTCTGCA | CATCGATTGT | CGTCGGCGTC | GTGGAGATCG | 180 |
| TCGTGGTGCT | CCGGTGGTGG | TCTTCGTCCG | CTTAGAATAG | TGTAGTTAGT | TAGGGGCCTT | 240 |
| CAAAGAAGAA | AGAAGAAGCG | ATTGGCGCGG | AGAGATGCTG | GAGGTGTCAG | TTTCTATGCT | 300 |
| AGAGTAGGGT | AGTGAAACAA | TCCCCAGCCA | AACCTTTCCG | GGGGCGCAG  | GTTGCCCACA | 360 |
| GGAGGTCGAC | TTGCCGGCGC | TGTCCTTCGC | GCCGAGCTCC | CTCCATCCTT | CTTTCCGTCT | 420 |
| GCTGAGACGC | AAGGTTGCGG | CGCGCACGCT | GAGCAGCGCA | CTGACTGCCG | CGGGCTCCGC | 480 |
| TGGGCGATTG | CAGCCGAGTC | CGTTTCTCGT | CTAGCTGCCG | CCGCGGCGAC | CTGCCTGGTC | 540 |
| TTCCTCCCGG | ACGCTAGCGG | GTTGTCAACT | ATTACCTGCA | AGCATAGGCC | AACGAACACC | 600 |
| TTCTTTCCAA | ATTAATTGGA | ATGAAACAAT | TCTGTTAACT | TCCTAATTCT | CAGTTTGAAA | 660 |
| CTCTGGTTGC | TTAAGCCTGA | AGCAATCATG | GTGAACCTTG | GCAACGCGGT | GCGCTCGCTC | 720 |
| CTGATGCACC | TAATCGGCCT | ATTGGTTTGG | CAATTCGATA | TTTCCATAAG | TCCAGTAGCA | 780 |
| GCTATAGTAA | CTGACACTTT | TAATTCCTCC | GATGGTGGAC | GCTTGTTTCA | ATTCCCGGAC | 840 |
| GGGGTACAAA | ACTGGCCAGC | ACTTTCAATC | GTCGTGATTA | TAATCATGAC | AATAGGGGGC | 900 |
| AACATTCTTG | TTATCATGGC | AGTAAGCATG | GAGAAGAAAC | TGCACAATGC | AACCAATTAC | 960 |
| TTCTTAATGT | CCCTAGCCAT | TGCTGATATG | CTGGTGGGAC | TACTTGTCAT | GCCCCTGTCC | 1020 |
| CTGCTTGCTA | TTCTTTATGA | TTATGTCTGG | CCTTTACCTA | GATATTTGTG | CCCCGTCTGG | 1080 |
| ATTTCACTAG | ATGTGCTATT | TTCAACTGCG | TCCATCATGC | ACCTCTGCGC | CATATCGCTG | 1140 |
| GACCGGTATG | TAGCAATACG | TAATCCTATT | GAGCATAGCC | GGTTCAATTC | GCGGACTAAG | 1200 |
| GCCATCATGA | AGATTGCCAT | CGTTTGGGCA | ATATCAATAG | GAGTTTCAGT | TCCTATCCCT | 1260 |

FIG. 37B

```
GTGATTGGAC TGAGGGACGA AAGCAAAGTG TTCGTGAATA ACACCACGTG CGTGCTCAAT  1320

GACCCCAACT TCGTTCTCAT CGGGTCCTTC GTGGCATTCT TCATCCCGTT GACGATTATG  1380

GTGATCACCT ACTTCTTAAC GATCTACGTC CTGCGCCGTC AAACTCTGAT GTTACTTCGA  1440

GGTCACACCG AGGAGGAACT GGCTAATATG AGCCTGAACT TTCTGAACTG CTGCTGCAAG  1500

AAGAATGGTG GTGAGGAAGA GAACGCTCCG AACCCTAATC CAGATCAGAA ACCACGTCGA  1560
                                            Start S312K primer
AAGAAGAAAG AAAAGCGTCC CAGAGGCACC ATGCAAGCTA TCAACAACGA AAAGAAAGCT  1620
                  End S312K primer
AAGAAAGTCC TTGGCATTGT ATTCTTTGTG TTTCTGATCA TGTGGTGCCC GTTTTTCATC  1680

ACCAATATCC TGTCGGTTCT TTGTGGGAAG GCCTGTAACC AAAAGCTAAT GGAGAAGCTT  1740

CTCAATGTGT TTGTGTGGAT TGGCTATGTG TGTTCAGGCA TCAATCCTCT GGTGTACACT  1800

CTCTTTAATA AAATTTACCG AAGGGCTTTC TCTAAATATT GCGCTGCGA TTATAAGCCA  1860

GACAAAAAGC CTCCTGTTCG ACAGATTCCT AGGGTTGCTG CCACTGCTTT GTCTGGGAGG  1920

GAGCTCAATG TTAACATTTA TCGGCATACC AATGAACGTG TGGCTAGGAA AGCTAATGAC  1980

CCTGAGCCTG GCATAGAGAT GCAGGTGGAG AACTTAGAGC TGCCAGTCAA CCCCTCTAAT  2040

GTGGTCAGCG AGAGGATTAG TAGTGTGTAA GCGAAGAGCA GCGCAGACTT CCTACAGGAA  2100

AGTTCCTGTA GGAAAGTCCT CCCCACCCCC CGTGATTTTC CTGTGAATCA TAACTAATGT  2160

AAATATTGCT GTGTGACAAG ACAGTGTTTT TATAAATAGC TTTGCAACCC TGTACTTTAC  2220

ATCATGCGTT AATAGTGAGA TTCGGG                                       2246
```

FIG. 38A

Rat 5HT₂c Serine -> Lysine Mutant with Restriction Site

ORIGIN 23 bp upstream of HindIII site.

| | | | | | |
|---|---|---|---|---|---|
| GGCGCTCTGG | TGCTCACTGA | GGAAGCTTCC | TTAGGTGTAC | CGATCTTAAT | GATTGAGCCC | 60 |
| TTGGAGCAGC | AAGATTGTTA | ATCTTGGTTG | CTCCTTTGGC | CTGTCTATCC | CTTACCTTCC | 120 |
| TATTACATAT | GAACTTTTCT | TCGTTCTGCA | CATCGATTGT | CGTCGGCGTC | GTGGAGATCG | 180 |
| TCGTGGTGCT | CCGGTGGTGG | TCTTCGTCCG | CTTAGAATAG | TGTAGTTAGT | TAGGGCCTT | 240 |
| CAAAGAAGAA | AGAAGAAGCG | ATTGGCGCGG | AGAGATGCTG | GAGGTGTCAG | TTTCTATGCT | 300 |
| AGAGTAGGGT | AGTGAAACAA | TCCCCAGCCA | AACCTTTCCG | GGGGCGCAG | GTTGCCCACA | 360 |
| GGAGGTCGAC | TTGCCGGCGC | TGTCCTTCGC | GCCGAGCTCC | CTCCATCCTT | CTTTCCGTCT | 420 |
| GCTGAGACGC | AAGGTTGCGG | CGCGCACGCT | GAGCAGCGCA | CTGACTGCCG | CGGGCTCCGC | 480 |
| TGGGCGATTG | CAGCCGAGTC | CGTTTCTCGT | CTAGCTGCCG | CCGCGGCGAC | CTGCCTGGTC | 540 |
| TTCCTCCCGG | ACGCTAGCGG | GTTGTCAACT | ATTACCTGCA | AGCATAGGCC | AACGAACACC | 600 |
| TTCTTTCCAA | ATTAATTGGA | ATGAAACAAT | TCTGTTAACT | TCCTAATTCT | CAGTTTGAAA | 660 |
| CTCTGGTTGC | TTAAGCCTGA | AGCAATCATG | GTGAACCTTG | GCAACGCGGT | GCGCTCGCTC | 720 |
| CTGATGCACC | TAATCGGCCT | ATTGGTTTGG | CAATTCGATA | TTTCCATAAG | TCCAGTAGCA | 780 |
| GCTATAGTAA | CTGACACTTT | TAATTCCTCC | GATGGTGGAC | GCTTGTTTCA | ATTCCCGGAC | 840 |
| GGGGTACAAA | ACTGGCCAGC | ACTTTCAATC | GTCGTGATTA | TAATCATGAC | AATAGGGGGC | 900 |
| AACATTCTTG | TTATCATGGC | AGTAAGCATG | GAGAAGAAAC | TGCACAATGC | AACCAATTAC | 960 |
| TTCTTAATGT | CCCTAGCCAT | TGCTGATATG | CTGGTGGGAC | TACTTGTCAT | GCCCCTGTCC | 1020 |
| CTGCTTGCTA | TTCTTTATGA | TTATGTCTGG | CCTTTACCTA | GATATTTGTG | CCCCGTCTGG | 1080 |
| ATTTCACTAG | ATGTGCTATT | TTCAACTGCG | TCCATCATGC | ACCTCTGCGC | CATATCGCTG | 1140 |
| GACCGGTATG | TAGCAATACG | TAATCCTATT | GAGCATAGCC | GGTTCAATTC | GCGGACTAAG | 1200 |
| GCCATCATGA | AGATTGCCAT | CGTTTGGGCA | ATATCAATAG | GAGTTTCAGT | TCCTATCCCT | 1260 |

FIG. 38B

```
GTGATTGGAC TGAGGGACGA AAGCAAAGTG TTCGTGAATA ACACCACGTG CGTGCTCAAT  1320

GACCCCAACT TCGTTCTCAT CGGGTCCTTC GTGGCATTCT TCATCCCGTT GACGATTATG  1380

GTGATCACCT ACTTCTTAAC GATCTACGTC CTGCGCCGTC AAACTCTGAT GTTACTTCGA  1440

GGTCACACCG AGGAGGAACT GGCTAATATG AGCCTGAACT TCTGAACTG CTGCTGCAAG  1500

AAGAATGGTG GTGAGGAAGA GAACGCTCCG AACCCTAATC CAGATCAGAA ACCACGTCGA  1560
                                          Start S312K primer
AAGAAGAAAG AAAAGCGTCC CAGAGGCACC ATGCAAGCTA TCAACAACGA AAAGAAAGCT  1620
                End S312K primer
AAGAAAGTAC TTGGCATTGT ATTCTTTGTG TTTCTGATCA TGTGGTGCCC GTTTTTCATC  1680
            Mutation to create ScaI site
ACCAATATCC TGTCGGTTCT TTGTGGGAAG GCCTGTAACC AAAAGCTAAT GGAGAAGCTT  1740

CTCAATGTGT TTGTGTGGAT TGGCTATGTG TGTTCAGGCA TCAATCCTCT GGTGTACACT  1800

CTCTTTAATA AAATTTACCG AAGGGCTTTC TCTAAATATT TGCGCTGCGA TTATAAGCCA  1860

GACAAAAAGC CTCCTGTTCG ACAGATTCCT AGGGTTGCTG CCACTGCTTT GTCTGGGAGG  1920

GAGCTCAATG TTAACATTTA TCGGCATACC AATGAACGTG TGGCTAGGAA AGCTAATGAC  1980

CCTGAGCCTG GCATAGAGAT GCAGGTGGAG AACTTAGAGC TGCCAGTCAA CCCCTCTAAT  2040

GTGGTCAGCG AGAGGATTAG TAGTGTGTAA GCGAAGAGCA GCGCAGACTT CCTACAGGAA  2100

AGTTCCTGTA GGAAAGTCCT CCCCACCCCC CGTGATTTTC CTGTGAATCA TAACTAATGT  2160

AAATATTGCT GTGTGACAAG ACAGTGTTTT TATAAATAGC TTTGCAACCC TGTACTTTAC  2220

ATCATGCGTT AATAGTGAGA TTCGGG                                      2246
```

FIG. 39

Rat 5-HT$_{2C}$ Serine -> Phenylalanine Mutant

MVNLGNAVRSLLMHLIGLLVWQFDISISPVAAIVTDTFNSSDGG

RLFQFPDGVQNWPALSIVVIIIMTIGGNILVIMAVSMEKKLHNATNYFLMSLAIADML

VGLLVMPLSLLAILYDYVWPLPRYLCPVWISLDVLFSTASIMHLCAISLDRYVAIRNP

IEHSRFNSRTKAIMKIAIVWAISIGVSVPIPVIGLRDESKVFVNNTTCVLNDPNFVLI

GSFVAFFIPLTIMVITYFLTIYVLRRQTLMLLRGHTEEELANMSLNFLNCCCKKNGGE

EENAPNPNPDQKPRRKKKEKRPRGTMQAINNEKKAFKVLGIVFFVFLIMWCPFFITNI

LSVLCGKACNQKLMEKLLNVFVWIGYVCSGINPLVYTLFNKIYRRAFSKYLRCDYKPD

KKPPVRQIPRVAATALSGRELNVNIYRHTNERVARKANDPEPGIEMQVENLELPVNPS

NVVSERISSV

FIG. 40A

Rat 5HT$_{2C}$ Serine -> Phenylalanine Mutant

ORIGIN 23 bp upstream of HindIII site.

```
GGCGCTCTGG TGCTCACTGA GGAAGCTTCC TTAGGTGTAC CGATCTTAAT GATTGAGCCC    60
TTGGAGCAGC AAGATTGTTA ATCTTGGTTG CTCCTTTGGC CTGTCTATCC CTTACCTTCC   120
TATTACATAT GAACTTTTCT TCGTTCTGCA CATCGATTGT CGTCGGCGTC GTGGAGATCG   180
TCGTGGTGCT CCGGTGGTGG TCTTCGTCCG CTTAGAATAG TGTAGTTAGT TAGGGCCTT    240
CAAAGAAGAA AGAAGAAGCG ATTGGCGCGG AGAGATGCTG GAGGTGTCAG TTTCTATGCT   300
AGAGTAGGGT AGTGAAACAA TCCCCAGCCA AACCTTTCCG GGGGCGCAG GTTGCCCACA    360
GGAGGTCGAC TTGCCGGCGC TGTCCTTCGC GCCGAGCTCC CTCCATCCTT CTTTCCGTCT   420
GCTGAGACGC AAGGTTGCGG CGCGCACGCT GAGCAGCGCA CTGACTGCCG CGGGCTCCGC   480
TGGGCGATTG CAGCCGAGTC CGTTTCTCGT CTAGCTGCCG CCGCGGCGAC CTGCCTGGTC   540
TTCCTCCCGG ACGCTAGCGG GTTGTCAACT ATTACCTGCA AGCATAGGCC AACGAACACC   600
TTCTTTCCAA ATTAATTGGA ATGAAACAAT TCTGTTAACT TCCTAATTCT CAGTTTGAAA   660
CTCTGGTTGC TTAAGCCTGA AGCAATCATG GTGAACCTTG GCAACGCGGT GCGCTCGCTC   720
CTGATGCACC TAATCGGCCT ATTGGTTTGG CAATTCGATA TTTCCATAAG TCCAGTAGCA   780
GCTATAGTAA CTGACACTTT TAATTCCTCC GATGGTGGAC GCTTGTTTCA ATTCCCGGAC   840
GGGGTACAAA ACTGGCCAGC ACTTTCAATC GTCGTGATTA TAATCATGAC AATAGGGGGC   900
AACATTCTTG TTATCATGGC AGTAAGCATG GAGAAGAAAC TGCACAATGC AACCAATTAC   960
TTCTTAATGT CCCTAGCCAT TGCTGATATG CTGGTGGGAC TACTTGTCAT GCCCCTGTCC  1020
CTGCTTGCTA TTCTTTATGA TTATGTCTGG CCTTTACCTA GATATTTGTG CCCCGTCTGG  1080
ATTTCACTAG ATGTGCTATT TTCAACTGCG TCCATCATGC ACCTCTGCGC CATATCGCTG  1140
GACCGGTATG TAGCAATACG TAATCCTATT GAGCATAGCC GGTTCAATTC GCGGACTAAG  1200
GCCATCATGA AGATTGCCAT CGTTTGGGCA ATATCAATAG GAGTTTCAGT TCCTATCCCT  1260
```

FIG. 40B

```
GTGATTGGAC TGAGGGACGA AAGCAAAGTG TTCGTGAATA ACACCACGTG CGTGCTCAAT  1320

GACCCCAACT TCGTTCTCAT CGGGTCCTTC GTGGCATTCT TCATCCCGTT GACGATTATG  1380

GTGATCACCT ACTTCTTAAC GATCTACGTC CTGCGCCGTC AAACTCTGAT GTTACTTCGA  1440

GGTCACACCG AGGAGGAACT GGCTAATATG AGCCTGAACT TTCTGAACTG CTGCTGCAAG  1500

AAGAATGGTG GTGAGGAAGA GAACGCTCCG AACCCTAATC CAGATCAGAA ACCACGTCGA  1560
                                      Start S312F primer
AAGAAGAAAG AAAAGCGTCC CAGAGGCACC ATGCAAGCTA TCAACAACGA AAAGAAAGCT  1620
                    End S312F primer
TTCAAAGTCC TTGGCATTGT ATTCTTTGTG TTTCTGATCA TGTGGTGCCC GTTTTTCATC  1680

ACCAATATCC TGTCGGTTCT TTGTGGGAAG GCCTGTAACC AAAAGCTAAT GGAGAAGCTT  1740

CTCAATGTGT TTGTGTGGAT TGGCTATGTG TGTTCAGGCA TCAATCCTCT GGTGTACACT  1800

CTCTTTAATA AAATTTACCG AAGGGCTTTC TCTAAATATT GCGCTGCGA TTATAAGCCA  1860

GACAAAAAGC CTCCTGTTCG ACAGATTCCT AGGGTTGCTG CCACTGCTTT GTCTGGGAGG  1920

GAGCTCAATG TTAACATTTA TCGGCATACC AATGAACGTG TGGCTAGGAA AGCTAATGAC  1980

CCTGAGCCTG GCATAGAGAT GCAGGTGGAG AACTTAGAGC TGCCAGTCAA CCCCTCTAAT  2040

GTGGTCAGCG AGAGGATTAG TAGTGTGTAA GCGAAGAGCA GCGCAGACTT CCTACAGGAA  2100

AGTTCCTGTA GGAAAGTCCT CCCCACCCCC CGTGATTTTC CTGTGAATCA TAACTAATGT  2160

AAATATTGCT GTGTGACAAG ACAGTGTTTT TATAAATAGC TTTGCAACCC TGTACTTTAC  2220

ATCATGCGTT AATAGTGAGA TTCGGG                                       2246
```

FIG. 41A

Rat 5HT$_{2C}$ 312Serine -> Phenylalanine Mutant with Restriction Site

ORIGIN    23 bp upstream of HindIII site

| | | | | | |
|---|---|---|---|---|---|
| GGCGCTCTGG | TGCTCACTGA | GGAAGCTTCC | TTAGGTGTAC | CGATCTTAAT | GATTGAGCCC | 60 |
| TTGGAGCAGC | AAGATTGTTA | ATCTTGGTTG | CTCCTTTGGC | CTGTCTATCC | CTTACCTTCC | 120 |
| TATTACATAT | GAACTTTTCT | TCGTTCTGCA | CATCGATTGT | CGTCGGCGTC | GTGGAGATCG | 180 |
| TCGTGGTGCT | CCGGTGGTGG | TCTTCGTCCG | CTTAGAATAG | TGTAGTTAGT | TAGGGCCTT | 240 |
| CAAAGAAGAA | AGAAGAAGCG | ATTGGCGCGG | AGAGATGCTG | GAGGTGTCAG | TTTCTATGCT | 300 |
| AGAGTAGGGT | AGTGAAACAA | TCCCCAGCCA | AACCTTTCCG | GGGGCGCAG | GTTGCCCACA | 360 |
| GGAGGTCGAC | TTGCCGGCGC | TGTCCTTCGC | GCCGAGCTCC | CTCCATCCTT | CTTTCCGTCT | 420 |
| GCTGAGACGC | AAGGTTGCGG | CGCGCACGCT | GAGCAGCGCA | CTGACTGCCG | CGGGCTCCGC | 480 |
| TGGGCGATTG | CAGCCGAGTC | CGTTTCTCGT | CTAGCTGCCG | CCGCGGCGAC | CTGCCTGGTC | 540 |
| TTCCTCCCGG | ACGCTAGCGG | GTTGTCAACT | ATTACCTGCA | AGCATAGGCC | AACGAACACC | 600 |
| TTCTTTCCAA | ATTAATTGGA | ATGAAACAAT | TCTGTTAACT | TCCTAATTCT | CAGTTTGAAA | 660 |
| CTCTGGTTGC | TTAAGCCTGA | AGCAATCATG | GTGAACCTTG | GCAACGCGGT | GCGCTCGCTC | 720 |
| CTGATGCACC | TAATCGGCCT | ATTGGTTTGG | CAATTCGATA | TTTCCATAAG | TCCAGTAGCA | 780 |
| GCTATAGTAA | CTGACACTTT | TAATTCCTCC | GATGGTGGAC | GCTTGTTTCA | ATTCCCGGAC | 840 |
| GGGGTACAAA | ACTGGCCAGC | ACTTTCAATC | GTCGTGATTA | TAATCATGAC | AATAGGGGGC | 900 |
| AACATTCTTG | TTATCATGGC | AGTAAGCATG | GAGAAGAAAC | TGCACAATGC | AACCAATTAC | 960 |
| TTCTTAATGT | CCCTAGCCAT | TGCTGATATG | CTGGTGGGAC | TACTTGTCAT | GCCCCTGTCC | 1020 |
| CTGCTTGCTA | TTCTTTATGA | TTATGTCTGG | CCTTTACCTA | GATATTTGTG | CCCCGTCTGG | 1080 |
| ATTTCACTAG | ATGTGCTATT | TTCAACTGCG | TCCATCATGC | ACCTCTGCGC | CATATCGCTG | 1140 |
| GACCGGTATG | TAGCAATACG | TAATCCTATT | GAGCATAGCC | GGTTCAATTC | GCGGACTAAG | 1200 |
| GCCATCATGA | AGATTGCCAT | CGTTTGGGCA | ATATCAATAG | GAGTTTCAGT | TCCTATCCCT | 1260 |

FIG. 41B

```
GTGATTGGAC TGAGGGACGA AAGCAAAGTG TTCGTGAATA ACACCACGTG CGTGCTCAAT  1320

GACCCCAACT TCGTTCTCAT CGGGTCCTTC GTGGCATTCT TCATCCCGTT GACGATTATG  1380

GTGATCACCT ACTTCTTAAC GATCTACGTC CTGCGCCGTC AAACTCTGAT GTTACTTCGA  1440

GGTCACACCG AGGAGGAACT GGCTAATATG AGCCTGAACT TTCTGAACTG CTGCTGCAAG  1500

AAGAATGGTG GTGAGGAAGA GAACGCTCCG AACCCTAATC CAGATCAGAA ACCACGTCGA  1560
                             Start S312F primer
AAGAAGAAAG AAAAGCGTCC CAGAGGCACC ATGCAAGCTA TCAACAA CGA AAAGAAAGCT  1620
                              End S312F primer
TTCAAAGTAC TTGGCATT GT ATTCTTTGTG TTTCTGATCA TGTGGTGCCC GTTTTTCATC  1680
         Mutation to create ScaI site
ACCAATATCC TGTCGGTTCT TGTGGGAAG GCCTGTAACC AAAAGCTAAT GGAGAAGCTT  1740

CTCAATGTGT TTGTGTGGAT TGGCTATGTG TGTTCAGGCA TCAATCCTCT GGTGTACACT  1800

CTCTTTAATA AAATTTACCG AAGGGCTTTC TCTAAATATT GCGCTGCGA TTATAAGCCA  1860

GACAAAAAGC CTCCTGTTCG ACAGATTCCT AGGGTTGCTG CCACTGCTTT GTCTGGGAGG  1920

GAGCTCAATG TTAACATTTA TCGGCATACC AATGAACGTG TGGCTAGGAA AGCTAATGAC  1980

CCTGAGCCTG GCATAGAGAT GCAGGTGGAG AACTTAGAGC TGCCAGTCAA CCCCTCTAAT  2040

GTGGTCAGCG AGAGGATTAG TAGTGTGTAA GCGAAGAGCA GCGCAGACTT CCTACAGGAA  2100

AGTTCCTGTA GGAAAGTCCT CCCCACCCCC CGTGATTTTC CTGTGAATCA TAACTAATGT  2160

AAATATTGCT GTGTGACAAG ACAGTGTTTT TATAAATAGC TTTGCAACCC TGTACTTTAC  2220

ATCATGCGTT AATAGTGAGA TTCGGG                                      2246
```

CONSTITUTIVELY ACTIVATED SEROTONIN RECEPTORS

The benefit of U.S. Provisional Application No. 60/039,465 filed Feb. 27, 1997, and U.S. Provisional Application No. 60/061,268 filed Oct. 7, 1997 is claimed for this application.

BACKGROUND OF THE INVENTION

1. Field of the Invention

The present invention relates generally to the field of transmembrane receptors, more particularly to seven segment transmembrane G protein-coupled receptors, and most particularly to the serotonin (5-HT) receptors. Through genetic mutational techniques, the amino acid sequences of the native $5\text{-HT}_{2A}$ and $5\text{-HT}_{2C}$ receptors have been modified so that the receptors exist in a constitutively activated state exhibiting both a greater response to agonists and a coupling to the G Protein second messenger system even in the absence of agonist. A method for constitutively activating G protein-coupled 5-HT receptors in general is also disclosed.

2. Description of Related Art

The research interest in G protein-coupled cell surface receptors has exploded in recent years as it has been apparent that variants of these receptors play a significant role in the etiology of many severe human diseases. These receptors serve a diverse array of signalling pathways in a wide variety of cells and tissue types. Indeed, over the past 20 years, G protein-coupled receptors have proven to be excellent therapeutic targets with the development of several hundred drugs directed towards activating or deactivating them.

G protein-coupled receptors form a superfamily of receptors which are related both in their structure and their function. Structurally the receptors are large macromolecular proteins embedded in and spanning the cell membrane of the receiving cell and are distinguished by a common structural motif. All the receptors have seven domains of between 22 to 24 hydrophobic amino acids forming seven α helixes arranged in a bundle which span the cell membrane substantially perpendicular to the cell membrane. The transmembrane helixes are joined by chains of hydrophilic amino acids. The amino terminal and three connecting chains extend into the extracellular environment while the carboxy terminal and three connecting chains extend into the intracellular environment. Signalling molecules are believed to be recognized by the parts of the receptor which span the membrane or lie on or above the extracellular surface of the cell membrane. The third intracellular loop joining helixes five and six is thought to be the most crucial domain involved in receptor/G protein coupling and responsible for the receptor selectivity for specific types of G proteins.

Functionally, all the receptors transmit the signal of an externally bound signalling molecule across the cell membrane to activate a heterotrimeric transducing protein which binds GDP (guanosine diphosphate). Upon activation, the bound GDP is converted to GTP (guanosine triphosphate). The activated G protein complex then triggers further intracellular biochemical activity. Different G proteins mediate different intracellular activities through various second messenger systems including, for example, 3'5'-cyclic AMP (cAMP), 3'5'-cyclic GMP (cGMP), 1,2-diacylglycerol, inositol 1,4,5-triphosphate, and $Ca^{2+}$. Within the human genome, several hundred G protein-coupled receptors have been identified and endogenous ligands are known for approximately 100 of the group. While the seven transmembrane motif is common among the known receptors, the amino acid sequences vary considerably, with the most conserved regions consisting of the transmembrane helixes.

Binding of a signalling molecule to a G protein-coupled receptor is believed to alter the conformation of the receptor, and it is this conformational change which is thought responsible for the activation of the G protein. Accordingly, G protein-coupled receptors are thought to exist in the cell membrane in equilibrium between two states or conformations: an "inactive" state and an "active" state. In the "inactive" state (conformation) the receptor is unable to link to the intracellular transduction pathway and no biological response is produced. In the altered conformation, or "active" state, the receptor is able to link to the intracellular pathway to produce a biological response. Signalling molecules specific to the receptor are believed to produce a biological response by stabilizing the receptor in the active state.

Discoveries over the past several years have shown that G protein-coupled receptors can also be stabilized in the active conformation by means other than binding with the appropriate signal molecule. Four principal methods have been identified: 1) molecular alterations in the amino acid sequence at specific sites; 2) stimulation with anti-peptide antibodies; 3) over-expression in in vitro systems; and 4) over-expression of the coupling G proteins. These other means simulate the stabilizing effect of the signalling molecule to keep the receptor in the active, coupled, state. Such stabilization in the active state is termed "constitutive receptor activation".

Several features distinguish the constitutively activated receptors. First, they have an affinity for the native signalling molecule and related agonists which is typically greater than that of the native receptors. Second, where several known agonists of varying activity (to the native receptor) were known, it was found that the greater the initial activity of the agonist, the greater was the increase in its affinity for the constitutively activated receptor. Third, the affinity of the constitutively activated receptor for antagonists is not increased over the affinity for the antagonist of the native receptor. Fourth, the constitutively activated receptors remain coupled to the second messenger pathway and produce a biological response even in the absence of the signalling molecule or other agonist.

The importance of constitutively activated receptors to biological research and drug discovery cannot be overstated. First, these receptors provide an opportunity to study the structure of the active state and provide insights into how the receptor is controlled and the steps in receptor activation. Second, the constitutively active receptors allow study of the mechanisms by which coupling to G proteins is achieved as well as how G protein specificity is determined. Third, mutated constitutively active receptors are now recognized in disease states. Study of constitutively activated receptors has demonstrated that many mutations may lead to constitutive activation and that a whole range of activation is possible. Fourth, the existence of constitutively active receptors provides a novel screening mechanism with which compounds which act to increase or decrease receptor activity can be identified and evaluated. Such compounds may become lead compounds for drug research. Finally, studying the affect of classical antagonists (compounds previously identified as, in the absence of agonist, binding to the receptor but causing no change in receptor activitiy, and, in the presence of agonist, competitively decreasing the activity of a receptor) and other drugs used as treatments on the constitutively active receptors has led to the discovery that there are compounds, inverse agonists, which decrease the constitutive activity of the active state of the receptors but which have no or little affect on the inactive state. The difference between antagonists, which act on the inactive state, and inverse agonists, which act on the active state, is only discernable when the receptor exhibits constitutive activity. These inverse agonists, identifiable with constitutively active receptors, present an entirely new class of potential compounds for drug discovery.

About 10 years ago, it was recognized that neurotransmitter receptors can be divided into two general classes depending on the rapidity of their response. Fast receptors were identified with ion channels and mediate millisecond responses while slower receptors were identified with G protein-coupled receptors. These G protein-coupled receptors include certain subtypes of the adrenergic as well as the muscarinic cholinergic (M1–M5), dopaminergic (D1–D5), serotonergic (5-HT1, 5-HT2, 5-HT4–5-HT7) and opiate ($\delta$, $\kappa$, and $\mu$) receptors. Each of these G protein-coupled neurotransmitter receptors has been associated with profound changes in mental activity and functioning, and it is believed that abnormal activity of these receptors may contribute to certain psychiatric disorders. Consequently, the elucidation of the mechanism of action of these receptors has been the focus of vigorous research efforts.

Serotonin receptors are of particular importance. Serotonin-containing cell bodies are found at highest density in the raphe regions of the pons and upper brain stem. However, these cells project into almost all brain regions and the spinal column. Serotonin does not cross the blood-brain barrier and is synthesized directly in neurons from L-tryptophan. In the CNS serotonin is thought to be involved in learning and memory, sleep, thermoregulation, motor activity, pain, sexual and aggressive behaviors, appetite, neuroendocrine regulation, and biological rhythms. Serotonin has also been linked to pathophysiological conditions such as anxiety, depression, obsessive-compulsive disorders, schizophrenia, suicide, autism, migraine, emesis, alcoholism and neurodegenerative disorders. Presently several drugs are used to modify serotonin receptors: 1) 5-HT1: sumatriptan for treatment of migraine, ipsapirone and buspirone for treatment of anxiety; 2) 5-HT2: clozapine and risperidone for treatment of schizophrenia; and 3) 5-HT3: odanestron for the prevention of emesis in chemotherapy.

To date, fourteen serotonin receptors have been identified in 7 subfamilies based on structural homology, second messenger system activation, and drug affinity for certain ligands. The $5-HT_2$ subfamily is divided into 3 classes: $5-HT_{2A}$, $5-HT_{2B}$, and $5-HT_{2C}$. $5-HT_{2A}$ and $5-HT_{2C}$ receptor antagonists are thought to be useful in treating depression, anxiety, psychosis, and eating disorders. $5-HT_{2A}$ and $5-HT_{2C}$ receptors exhibit 51% amino acid homology overall and approximately 80% homology in the transmembrane domains. The $5-HT_{2C}$ receptor was cloned in 1987 and led to the cloning of the $5-HT_{2A}$ receptor in 1990. Studies of the $5-HT_{2A}$ receptor in recombinant mammalian cell lines revealed that the receptor possessed two affinity states, high and low. Both the $5-HT_{2A}$ and $5-HT_{2C}$ receptors are coupled to phospholipase C and mediate responses through the phosphatidylinositol pathway. Studies with agonists and antagonists display a wide range of receptor responses suggesting that there is a wide diversity of regulatory mechanisms governing receptor activity. The $5-HT_{2A}$ and $5-HT_{2C}$ receptors have also been implicated as the site of action of hallucinogenic drugs.

Much of the knowledge about the structure of G protein-coupled receptors has come from the study of the $\beta_2$-adrenergic receptor. Over the last several years, site-directed mutagenesis has been used to try to determine the amino acid residues important for ligand binding in both the $\beta_2$-adrenergic and $5-HT_{2A}$ receptors. In addition, studies have suggested that in a native (inactive) state of G protein-coupled receptors, the third intracellular loop is tucked into the receptor and is not available for interaction with the G protein. A change of receptor conformation (active) results in the availability or exposure of the C-terminal region of the third intracellular loop.

In 1990 Cotecchia et al.[1] were studying the G protein specificity determining characteristics of the third intracellular loop by creating chimeric receptors in which the third intracellular loops had been exchanged between the $\alpha_1$-adrenergic receptor and the $\beta_2$-adrenergic receptor. The specific G protein coupled activation was essentially switched between the two receptors. While attempting to determine which portions of the loop were responsible for the specificity, Cotecchia et al. discovered an unexpected phenomena; namely that the modification in the third intracellular loop of the $\alpha_1$-adrenergic receptor of three residues, Arg288, Lys290, and Ala293, created a mutant receptor with two orders of magnitude greater affinity for agonist and which coupled to the second messenger system even in the absence of agonist. These modifications were made in the carboxy end of the third cytoplasmic loop adjacent to the sixth transmembrane helix. The changes responsible for this increase were isolated to either a Ala293→Leu or a Lys290→His mutation. Thus, a constitutively active state of a G protein-coupled neuroreceptor had been created. Subsequently, Kjelsberg et al.[2] demonstrated that mutation of the amino acid at position 293 in the $\alpha_{1B}$-adrenergic receptor to any other of the 19 amino acids also produced a constitutively active state. Subsequently, mutations in the $\beta_2$-adrenergic receptor near the carboxy end of the third cytoplasmic loop have also been shown by Samama et al.[3] to constitutively activate this receptor.

When foci resulting from constitutively active $\alpha_{1B}$-adrenergic receptors were injected into nude mice, tumor formation occurred. Over the past 5 years, since the discovery that several thyroid adenomas contained mutations of the thyroid stimulating hormone (TSH) receptor, constitutively activated receptors have been found associated with several human disease states. The mutations responsible for these disease states have been found in the transmembrane domains and intracellular loops. For the TSH receptor, mutations at 13 different amino acid positions have been found in the transmembrane domain, the third intracellular loop, and the second and third extracellular loops. Clearly, constitutively activating mutations are not limited to the third intracellular loop and the critical site for constitutive activation varies with each G protein-coupled receptor. The importance of the initial observations was well stated in Cotecchia et al.[1]: "Such mutations might not only help to illuminate the biochemical mechanisms involved in receptor-G protein coupling but also provide models for how point mutations might activate potentially oncogenic receptors."

In light of the above referenced discoveries, the importance and utility of discovering other constitutively activated neuronal receptors cannot be understated. However, the hope that other neuronal receptors could be easily and readily mutated to a constitutively active form by mutations in the third cytoplasmic loop was destroyed by the report of Burstein et al.[4] in 1995 of a comprehensive mutational approach to the G protein coupled M5 muscarinic acetylcholine receptor. In that approach, Burstein et al. had randomly and comprehensively mutated the C-terminal region of the third intracellular loop of the M5 muscarinic acetylcholine receptor, but no constitutive activating mutations were found.

Definition:

CONSTITUTIVELY ACTIVATED RECEPTOR shall mean a G protein-coupled receptor which: 1) exhibits an increase in basal activity of the second messenger pathway in the absence of agonist above the level of activity observed in the wild type receptor in the absence of agonist; 2) may exhibit an increased affinity and potency for agonists; 3) exhibits an unmodified or decreased affinity for antagonists; and 4) exhibits a decrease in basal activity by inverse agonists.

SUMMARY OF THE INVENTION

Constitutively active forms of the rat 5-HT$_{2A}$ and 5-HT$_{2C}$ serotonin receptors have been obtained by a site-directed mutational method that will permit the constitutive activation of all mammalian G protein-coupled serotonin receptors. An amino acid position that will lead to a successful mutation in the serotonin receptor may be identified by alignment of the serotonin receptor against the amino acid sequence of the $\alpha_{1B}$-adrenergic receptor. Mutating the amino acid in the serotonin receptor which corresponds to the most sensitive position in the $\alpha_{1B}$-adrenergic receptor, alanine 293, yields a constitutively active serotonin receptor. A strongly constitutively active serotonin receptor is achieved when the mutation in the serotonin receptor is to one of the amino acids which produces the highest level of basal activation in constitutively activated $\alpha_{1B}$-adrenergic receptors. Successful constitutive activation of the serotonin receptor can be shown by increased high basal levels of second messenger activity in the absence of agonist, increased affinity and potency for agonists, and an unmodified or decreased affinity for antagonists. While standard methods of site-directed mutagenesis may be employed, the careful placement of restriction sites in the primer permits the more rapid and direct determination of the clone containing the desired mutated receptor.

It is the object of this invention to provide a general methodology for obtaining constitutively active forms of the G protein-coupled mammalian monoamine receptors.

It is a further object of this invention to provide a general methodology for obtaining constitutively active forms of the G protein-coupled mammalian serotonin receptors.

It is another object of this invention to provide a constitutively active 5-HT$_{2A}$ serotonin receptor.

It is a further object of this invention to provide a constitutively active 5-HT$_{2C}$ serotonin receptor.

Yet another object of this invention is to provide a method for rapidly identifying the clone containing the desired mutated receptor.

These and other achievements of the present invention will become apparent from the detailed description which follows.

DESCRIPTION OF THE FIGURES

FIGS. 1A–1B (SEQ ID NO: 1) shows the full DNA sequence for the rat 5-HT$_{2A}$ serotonin receptor including the 5' and 3' untranslated regions with the translated codons underlined.

FIG. 2 (SEQ ID NO: 2) shows the translated amino acid sequence for the rat 5-HT$_{2A}$ receptor.

FIGS. 3A–3B (SEQ ID NO: 3) shows the full DNA sequence for the rat 5-HT$_{2C}$ serotonin receptor including the 5' and 3' untranslated regions with the translated codons underlined.

FIG. 4 (SEQ ID NO: 4) shows the translated amino acid sequence for the rat 5-HT$_{2C}$ receptor.

FIG. 5 (SEQ ID NO: 5) shows the full DNA sequence for the rat $\alpha_{1B}$-adrenergic receptor including the 5' and 3' untranslated regions with the translated codons underlined.

FIGS. 6B–6B (SEQ ID NO: 6) shows the translated amino acid sequence for the rat $\alpha_{1B}$-adrenergic receptor.

FIG. 7 shows the amino acid sequences for part of the C-terminal third intracellular loop and transmembrane domain VI for the 5-HT$_{2A}$ and 5-HT$_{2C}$ receptors aligned opposite the corresponding part of the $\alpha_{1B}$-adrenergic receptor with numerals representing the amino acid positions in each receptor.

FIG. 14 shows a saturation analysis of $^3$H-ketanserin labeled native and cys→lys mutant receptors. Bmax values were determined by a BCA assay.

FIG. 18 also shows the results of $^3$H-mesulergine saturation analyses. Saturation experiments were performed using $^3$H-mesulergine (0.1 nM–5.0 nM).

FIGS. 23A–23C (SEQ ID NO: 7) sets forth the full DNA sequence for the human 5-HT$_{2A}$ serotonin receptor with the translated codons underlined. The sixth transmembrane domain conserved sequence of WxPFFI is indicated with block letters. FIG. 24 (SEQ ID NO: 8) shows the translated amino acid sequence for the human 5-HT$_{2A}$ receptor.

FIGS. 25A–25C (SEQ ID NO: 9) sets forth the full DNA sequence for the human 5-HT$_{2C}$ serotonin receptor with the translated codons underlined. The sixth transmembrane domain conserved sequence of WxPFFI is indicated with block letters. FIG. 26 (SEQ ID NO: 10) shows the translated amino acid sequence for the human 5-HT$_{2C}$ receptor.

FIG. 27 (SEQ ID NO: 11) is the amino acid sequence of the 5-HT$_{2A}$ cys→lys mutant receptor with the mutated amino acid shown as a larger outlined letter.

FIGS. 28A–28B (SEQ ID NO: 12) is the DNA sequence of the 5-HT$_{2A}$ cys→lys mutant receptor including the 5' and 3' untranslated regions with the translated codons underlined. The bases specifying the #322 lysine mutant are shown as larger outlined letters, and the starting and ending locations of the primer are also indicated.

FIGS. 29A–29B (SEQ ID NO: 13) is the DNA sequence of the 5-HT$_{2A}$ cys→lys mutant receptor including the 5' and 3' untranslated regions with the translated codons underlined. The bases specifying the #322 lysine mutant are shown as larger outlined letters, and the starting and ending locations of the primer are also indicated. In addition the two bases which were mutated to create the Sca1 site are shown as larger outlined letters and are indicated with arrows.

FIG. 30 (SEQ ID NO: 14) is the amino acid sequence of the 5-HT$_{2A}$ cys→arg mutant receptor with the mutated amino acid shown as a larger outlined letter.

FIGS. 31A–31B (SEQ ID NO: 15) is the DNA sequence of the 5-HT$_{2A}$ cys→arg mutant receptor including the 5' and 3' untranslated regions with the translated codons underlined. The bases specifying the #322 arginine mutant are shown as larger outlined letters, and the starting and ending locations of the primer are also indicated.

FIGS. 32A–32B (SEQ ID NO: 16) is identical to FIGS. 31A–31B (SEQ ID NO: 15) since the AGG mutation introduced for arginine creates an Mnl1 restriction site by itself at #319.

FIG. 33 (SEQ ID NO: 17) is the amino acid sequence of the 5-HT$_{2A}$ cys→glu mutant receptor with the mutated amino acid shown as a larger outlined letter.

FIGS. 34A–34B (SEQ ID NO: 18) is the DNA sequence of the 5-HT$_{2A}$ cys→glu mutant receptor including the 5' and 3' untranslated regions with the translated codons underlined. The bases specifying the #322 glutamic acid mutant are shown as larger outlined letters, and the starting and ending locations of the primer are also indicated.

FIGS. 35A–35B (SEQ ID NO: 19) is the DNA sequence of the 5-HT$_{2A}$ cys→glu mutant receptor including the 5' and 3' untranslated regions with the translated codons underlined. The bases specifying the #322 glutamic acid mutant are shown as larger outlined letters, and the starting and ending locations of the primer are also indicated. In addition the additional base which was mutated to create the Rsa1 site is shown as a larger outlined letter and is indicated with an arrow.

FIG. 36 (SEQ ID NO: 20) is the amino acid sequence of the 5-HT$_{2C}$ ser→lys mutant receptor with the mutated amino acid shown as a larger outlined letter.

FIGS. 37A–37B (SEQ ID NO: 21) is the DNA sequence of the 5-HT$_{2C}$ ser→lys mutant receptor including the 5' and 3' untranslated regions with the translated codons underlined. The bases specifying the #312 lysine mutant are shown as larger outlined letters, and the starting and ending locations of the primer are also indicated.

FIGS. 38A–38B (SEQ ID NO: 22) is the DNA sequence of the 5-HT$_{2C}$ ser→lys mutant receptor including the 5' and 3' untranslated regions with the translated codons underlined. The bases specifying the #312 lysine mutant are shown as larger outlined letters, and the starting and ending locations of the primer are also indicated. In addition the base which was mutated to create the Sca1 site is shown as a larger outlined letter and is indicated with an arrow.

FIG. 39 (SEQ ID NO: 23) is the amino acid sequence of the 5-HT$_{2C}$ ser→phe mutant receptor with the mutated amino acid shown as a larger outlined letter.

FIGS. 40A–40B (SEQ ID NO: 24) is the DNA sequence of the 5-HT$_{2C}$ ser→phe mutant receptor including the 5' and 3' untranslated regions with the translated codons underlined. The bases specifying the #312 phenylalanine mutant are shown as larger outlined letters, and the starting and ending locations of the primer are also indicated.

FIGS. 41A–41B (SEQ ID NO: 25) is the DNA sequence of the 5-HT$_{2C}$ ser→phe mutant receptor including the 5' and 3' untranslated regions with the translated codons underlined. The bases specifying the #312 phenylalanine mutant are shown as larger outlined letters, and the starting and ending locations of the primer are also indicated. In addition the base which was mutated to create the Sca1 site is shown as a larger outlined letter and is indicated with an arrow.

DETAILED DESCRIPTION OF THE INVENTION

Figure 8:
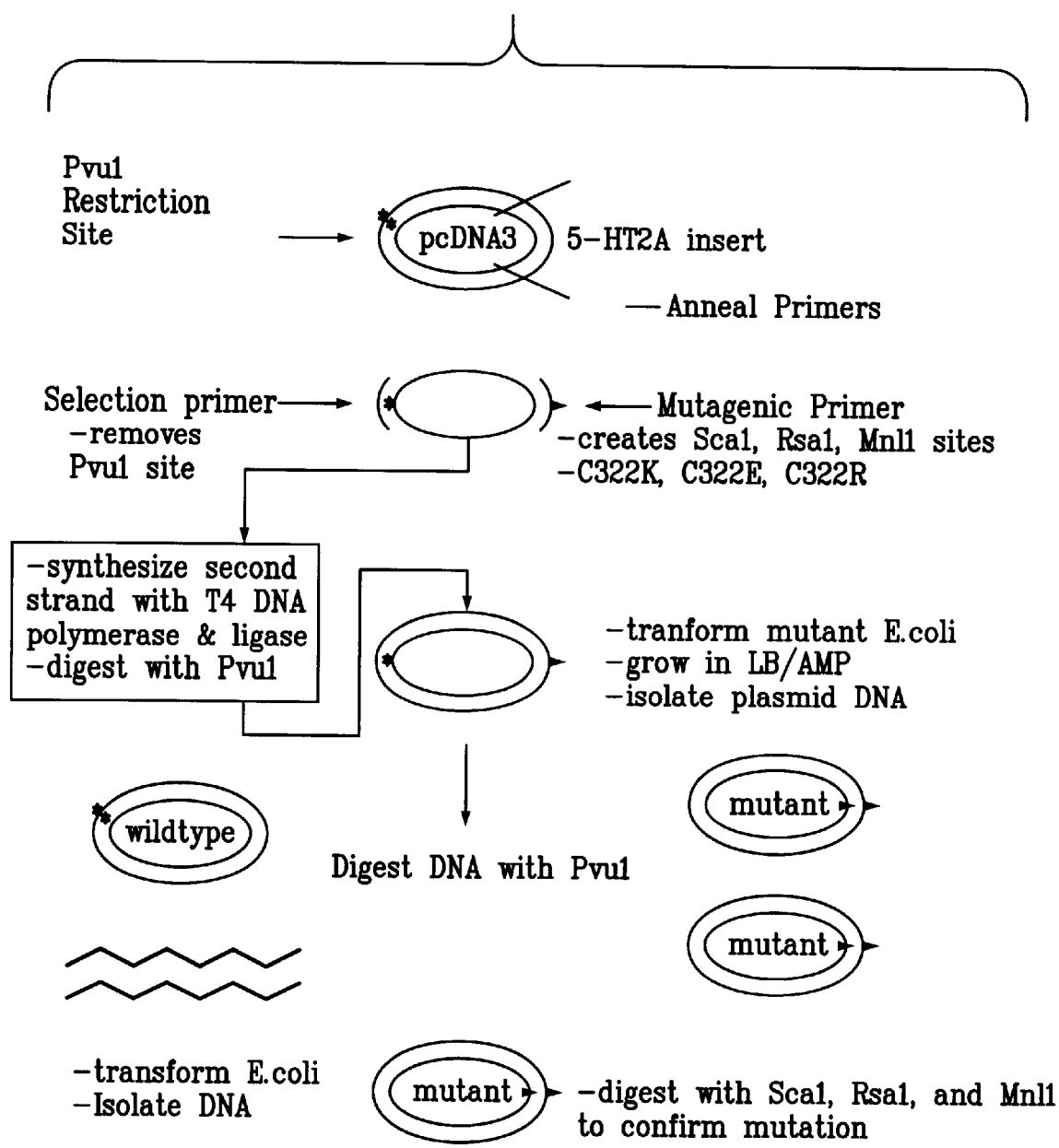
FIG. 8 shows a schematic outline of the 5-HT$_{2A}$ site-directed mutagenesis procedure.

Despite the disappointing results obtained by Burstein in mutating positions in the third intracellular loop of the M5 muscarinic acetylcholine receptor, the present inventive efforts focused on finding mutations at the carboxy end of the third intracellular loop near the sixth transmembrane helix in the serotonin receptors. DNA and amino acid sequences for rat 5-HT$_{2A}$ and 5-HT$_{2C}$ serotonin receptors were obtained from GeneBank as was the DNA and amino acid sequence for the $\alpha_{1B}$-adrenergic receptor. FIGS. 1A–1B, 2, 3A–3B, 4, 5 and 6A–6B list the full DNA and translated amino acid sequences for these receptors.

Receptor Alignment:

As noted above, Cotecchia et al. had identified amino acid position number 293 in the third intracellular loop adjoining the sixth transmembrane domain in the $\alpha_{1B}$-adrenergic receptor as a critical position, mutation of which lead to constitutive activity. However, the length of the serotonin receptors is different than the $\alpha_{1B}$-adrenergic receptor, and even had they been the same, matching the ends would not necessarily provide a structural or functional match. What was important was to find an alignment method which made sense in terms of locating the equivalent functional site to position 293 of the $\alpha_{1B}$-adrenergic receptor in the serotonin receptors.

A meaningful alignment method has been discovered based upon the fact that the transmembrane domains are highly conserved in G protein-coupled receptors. A series of conserved amino acid positions were identified in the sixth transmembrane domain which permit alignment of the transmembrane domain and the adjacent third intracellular loop between receptors. In FIG. 7 the conserved sixth transmembrane domain amino acid sequence WxPFFI (SEQ ID NO: 26) (x may be variable) has been used to align the three receptors. Alignment using this sequence also aligns the LGIV sequence found at the intracellular beginning of the sixth transmembrane domain which is connected to the third intracellular loop. This alignment indicates that in the 5-HT$_{2A}$ receptor the cysteine at position #322 corresponds to the alanine at position #293 in the $\alpha_{1B}$-adrenergic receptor. In the 5-HT$_{2C}$ receptor, the corresponding amino acid is a serine at position #312.

It should be noted that position 293 is not the only position in the $\alpha_{1B}$-adrenergic receptor which, when mutated, produced a constitutively active receptor. While Cotecchia et al.[1] reported that the A293L mutation produced the greatest constitutive activation, they also noted that the K290H mutation also induced dramatic constitutive activity. There are clearly other sites in the third intracellular loop of each of these receptors that can be mutated. In the future, other sites on other receptors may be reported. However, the alignment methodology presented above should serve to permit the structural correlation between different receptors so that information gleaned from one receptor may be utilized to mutate another receptor. However, the evidence presently available suggests that the third position removed from the beginning of the transmembrane domain represented by position 293 in the $\alpha_{1B}$-adrenergic receptor seems to play a crucial role in the binding and activation of the coupled G protein, and that mutations introduced at that position alter the tertiary structure of the region.

As noted earlier, Kjelsberg et al.[2] further demonstrated that substitution of any of the 19 amino acids at position 293 of the $\alpha_{1B}$-adrenergic receptor produced constitutive activity. However, the relative activity increased in the following order of amino acids: S, N, D, G, T, H, W, Y, P, V, L, M, Q, I, F, C, R, K, and E. In that study, replacing the native amino acid with amino acids having long basic or acidic side chains produced the greatest degree of constitutive activity, while amino acids with aromatic substituents produced an intermediate degree of constitutive activity. It is proposed that this order, with minor variations, exists for most G protein-coupled receptors due to the importance of the third position removed from the beginning of the transmembrane domain. A reasonable starting place for mutating receptors should therefore involve mutation to one of the amino acids at the most active end of the above list. Further, the tertiary structure of the region may be significantly altered by substituting an amino acid with longer side chains or of different polarity from the native amino acid.

Figure 9:
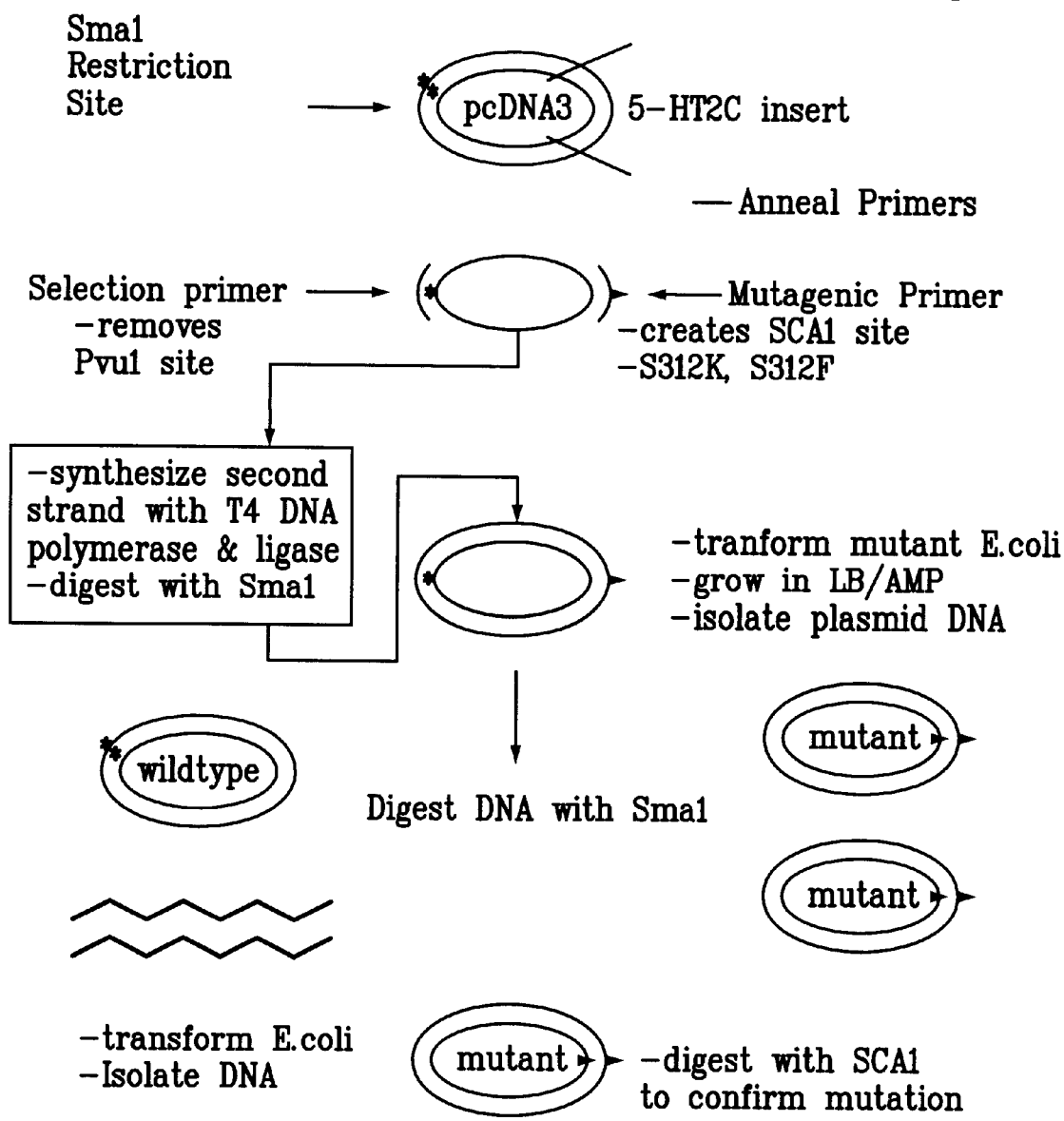
FIG. 9 shows a schematic outline of the 5-HT$_{2C}$ site-directed mutagenesis procedure.

Efficient Screening of Mutant Receptors:

When performing site-directed mutagenesis, it is common (and necessary) laboratory practice to fully sequence the cloned receptor to confirm that the mutation has been incorporated. However, because colonies containing the mutant receptor cannot be distinguished from those that do not, it is necessary to sequence each colony. A method, outlined schematically by way of example in FIG. 8 for the 5-HT$_{2A}$ cys→lys receptor mutation and in FIG. 9 for the 5-HT$_{2C}$ ser→lys and ser→phe receptor mutations, has been devised that rapidly and easily eliminates most non-mutated colonies, and from those remaining, identifies the mutant colony so that unnecessary sequencing is avoided. A two-pronged approach is used. The first prong is designed to prevent non-mutated vector from being incorporated during the first transformation by digesting the vector. E coli will only incorporate uncut (circular) plasmid DNA. Recognizing the limitations of the first prong, namely, that all restriction digests are not 100% complete so that some of the colonies at the end of the procedure will contain native DNA instead of mutant DNA, the second prong is designed to easily identify among the remaining colonies, those colonies containing the desired mutation after a second transformation.

To begin, a unique restriction site, not occurring in the native amino acid sequence, is incorporated into the mutant. It is possible to introduce the unique restriction site because of the degeneracy of the genetic code. The unique restriction site is ideally located within or near the amino acid(s) which specify the structural mutation which is being introduced into the mutant. Thus, the restriction site can be located on the same mutagenic primer as the structural mutation.

In addition, during the initial annealing, a second primer is used to remove a restriction site specific to the vector being used. When the second strand is synthesized with polymerase and ligase, only the second strand of the vector (the one not containing the mutations) will contain the original vector restriction site. Subsequently, after transformation, the colonies can be treated with the restriction enzyme specific for the vector site and only those resulting from the wildtype vector will be digested. Digested (cut) DNA will not be taken up by E. coli during the second transformation step. The colonies containing the mutated vector will not be digested and will be taken up by E. coli during the final transformation step.

Each resulting colony can be tested to see whether the restriction enzyme, which recognizes the unique site introduced by the mutated primer, digests the DNA. Only samples from colonies containing the desired mutation will be digested. These colonies can then be sequenced to confirm the insertion of the mutated amino acid. It is unnecessary to sequence colonies whose DNA is not digested by the restriction enzyme. This procedure yields a much more highly efficient method by saving both time and expense of sequencing every colony which results from the transformation experiment.

Measurement of Receptor-Coupled Second Messenger Activation:

In order to measure the stimulation produced through the 5-HT$_{2A}$ and the 5-HT$_{2C}$ receptors, an assay was utilized which measures the accumulation of inositol phosphates, the product that is formed when phosphatidylinositol 4,5-bisphosphate is hydrolyzed to DAG and IP. This assay was established by Berridge and coworkers (1983) in studies of the blowfly salivary glands, and found to be an accurate measurement of the stimulation of phospholipase C through receptor activation. $^3$H-myoinositol is incorporated into the cell membrane by conversion to phosphatidylinositol 4,5-bisphosphate and upon receptor activation, is cleaved by phospholipase C to yield two products: diacylglycerol and $^3$H-inositol 1,4,5 triphosphate (IP$_3$).

Inositol-free media must be used for this assay because unlabeled inositol, which is normally found in many commercially available media, can result in less than maximal incorporation of radiolabeled inositol into the cell membrane, resulting in a reduction in the amount of $^3$H-IP that would be detected. The $^3$H-IP is recovered by anion-exchange chromatography in which IP is separated from anion-exchange resin using washes of increasing concentrations of formate.

IP$_3$ is rapidly hydrolyzed to IP$_2$ by an inositol triphosphatase which is then converted to IP by inositol bisphosphatase. Because IP$_3$ is hydrolyzed so quickly, accumulation of IP would be hard to measure unless the cycle of IP to inositol and phosphate is blocked. Lithium is used in this assay to block the enzyme which converts IP to inositol and phosphate (myo-inositol monophosphatase). This ensures that IP levels can accumulate and be experimentally measured and are not undergoing the normal rapid degradation pathway. These experiments are also performed in serum free media in order to remove serotonin that can be found in serum which would complicate experimental results.

The total IP levels were measured in order to obtain an accurate measurement of the total amount of stimulation that occurred. The actual experimental conditions and concentrations of reagents used in this assay are set forth in the methods and materials sections under each example below.

EXAMPLE 1

Constitutive Activation of the 5-HT$_{2A}$ Receptor

Three separate mutations of the 5-HT$_{2A}$ receptor were made. The cysteine at position 322 was mutated to lysine, glutamate, and arginine.

Materials and Methods for Site-directed Mutagenesis:

The rat 5-HT2A receptor cDNA was ligated into the mammalian expression vector pcDNA3 (Invitrogen) using EcoR1 (GIBCO). This construct served as the native template for site-directed mutagenesis performed using Clontech's transformer kit. Mutagenic primers (Midland Certified Reagent Company) were designed as follows: the C322K primer was complementary to amino acid nos. 318–329 of the native 5-HT2A cDNA, while changing amino acid no. 322 from cysteine (TGC) to lysine (AAG). The same primer was designed to incorporate a Sca1 restriction site using amino acid nos. 323 and 324 by changing the third base in amino acid no. 323, lysine, from AAG to AAA and the third base in amino acid no. 324, valine from GTG to GTA. The C322E and C322R were designed complementary to amino acid nos. 319–330 of the native 5-HT2A cDNA, while changing amino acid no. 322 from cysteine (TGC) to glutamate (GAG) and arginine (AGG). In the C322E primer, an Rsa1 site was introduced by changing the third base in amino acid no. 324, valine, from GTG to GTA. The C322R mutation in the primer created an Mnl1 site, by itself, at amino acid no. 319. The selection primer, complementary to bases 4,871–4,914 of the pcDNA3 vector, was designed to remove a unique PVUI site by changing base G to T at location 4891. Phosphorylated primers were annealed to 10 ng of alkaline-denatured plasmid template by heating to 65° C. for 5 min and cooling slowly to 37° C. Mutant DNA was synthesized using T4 DNA polymerase and ligase (Clontech) by incubating for 1 hr at 37° C., followed by digestion with PVU1 (GIBCO) and transformation of BMH71-18mutS *E. coli* (Clontech). Plasmid was purified using the Wizard miniprep kit (Promega), digested with PVU1, and used to transform DH5(*E.Coli* (GIBCO). Individual colonies were isolated and plasmid DNA was digested with SCA1, Mnl1 or Rsa1 to screen for C322K, C322E and C322R mutations, respectively (GIBCO). DNA sequencing (Sequenase version 2.1 kit,USB, $^{35}$Sd-ATP, New England Nuclear) was performed to confirm the incorporation of lysine, glutamate, or arginine at amino acid no. 322. Sequencing reactions were run on a 5% acrylamide/bis (19:1) gel (Bio-Rad) for 2 hr at 50° C., dried for 2 hr at 80° C., and exposed on Kodak Biomax MR film for 24 hr at −80° C.

In FIG. 27 (SEQ ID NO: 11) is shown the amino acid sequence of the 5-HT$_{2A}$ cys→lys mutant receptor with the mutated amino acid shown as a larger outlined letter. FIGS. 28A–28B (SEQ ID NO: 12) shows the resulting DNA sequence of the 5-HT$_{2A}$ cys→lys mutant receptor including the 5' and 3' untranslated regions with the translated codons underlined. The bases specifying the #322 lysine mutant are shown as larger outlined letters, and the starting and ending locations of the primer are also indicated. In addition to showing the mutated DNA sequence of the 5-HT$_{2A}$ cys→lys mutant receptor, FIGS. 29A–29B (SEQ ID NO: 13) shows the two bases, which were mutated to create the Sca1 site, as larger outlined letters and are indicated with arrows.

In FIG. 30 (SEQ ID NO: 14) is shown the amino acid sequence of the 5-HT$_{2A}$ cys→arg mutant receptor with the mutated amino acid shown as a larger outlined letter. FIG. 26 (SEQ ID NO: 15) shows the resulting DNA sequence of the 5-HT$_{2A}$ cys→arg mutant receptor including the 5' and 3' untranslated regions with the translated codons underlined. The bases specifying the #322 arginine mutant are shown as larger outlined letters, and the starting and ending locations of the primer are also indicated. FIGS. 32A–32B (SEQ ID NO: 16) showing the added restriction site is identical to FIGS. 31A–31B (SEQ ID NO: 15) since the arginine mutation to AGG creates, by itself, an Mnl1 restriction site at #319.

In FIG. 33 (SEQ ID NO: 17) is shown the amino acid sequence of the 5-HT$_{2A}$ cys→glu mutant receptor with the mutated amino acid shown as a larger outlined letter. FIGS. 34A–34B (SEQ ID NO: 18) shows the resulitng DNA sequence of the 5-HT$_{2A}$ cys→glu mutant receptor including the 5' and 3' untranslated regions with the translated codons underlined. The bases specifying the #322 glutamic acid mutant are shown as larger outlined letters, and the starting and ending locations of the primer are also indicated. FIGS. 35A–35B (SEQ ID NO: 19) shows the additional base mutation introduced in amino acid 324 to create an Rsa1 site. The base mutation is indicted by a larger outlined letter and an arrow.

Cell Culture and Transfection:

COS-7 cells were grown in Dulbecco's modified Eagle's medium (DMEM, Sigma) with 10% fetal bovine serum (Sigma) in 5% CO$_2$ at 37° C. and subcultured 1:8 twice a week. Twenty-four hours before transfection, cells were seeded at 30% confluence in 100-mm dishes for radioligand binding assays or at 10$^5$ cells per well in 24-well cluster plates for IP production assays. Cells were transfected with native or mutant 5-HT2A cDNA using Lipofectamine (GIBCO). This was accomplished by combining 20 μl of Lipofectamine with 2.5 μg of plasmid per 100-mm dish or 2 μl of Lipofectamine with 0.25 μg of plasmid per well. Transfections were performed in serum-free DMEM for 4 hr at 37° C.

Radioligand Binding:

Thirty-six hours after transfection, membranes were prepared from COS-7 cells by scraping and homogenizing in 50 mM Tris-HCl/5 mM MgCl$_2$/0.5 mM EDTA, pH 7.4 (assay buffer), and centrifugation at 10,000×g for 30 min. Membranes were resuspended in assay buffer, homogenized, and centrifuged again. After resuspension in assay buffer, 1-ml membrane aliquots (approximately 10 μg of protein measured by bicinchoninic acid assay) were added to each tube containing 1 ml of assay buffer with 0.5 nM [$^3$H] ketanserin and competing drugs. 10 μM spiperone was used to define non-specific binding. Saturation experiments were performed by using [$^3$H]ketanserin (0.1–5.0 nM). Samples were incubated at 23° C. for 30 minutes, filtered on a Brandel cell harvester, and counted in Ecoscint cocktail (National Diagnostics) in a Beckman liquid scintillation counter at 40% efficiency.

Phosphatidylinositol Hydrolysis:

Inositol phosphate (IP) production was measured using a modified combination of the methods of Berridge et al. (1982) and Conn and Sanders-Bush (1985). In brief, 24 h after transfection, cells were washed with phosphate-buffered saline (PBS) and labeled with 0.25 μCi/well of myo-[$^3$H]inositol (New England Nuclear) in inositol free/serum-free DMEM (GIBCO) for 12 h at 37° C. HPLC analysis of this culture medium, after incubation, has been reported to contain <$10^{10}$ M 5-HT (Barker et al. 1994). After labeling, cells were washed with PBS and preincubated in inositol-free/serum-free DMEM with 10 mM LiCl and 10 μM pargyline (assay medium) for 10 min at 37° C. When antagonists were used, they were added during the 10-min preincubation period. 5-HT (Sigma), or assay medium alone, was added to each well and incubation continued for an additional 35 min (Westphal et al., 1995). Assay medium was removed and cells were lysed in 250 μl of stop solution (1 M KOH/18 mM sodium borate/3.8 mM EDTA) and neutralized by adding 250 μl of 7.5% HCl. The contents of each well were extracted with 3 volumes of chloroform/methanol (1:2), centrifuged 5 min at 10,000×g, and the upper layer loaded onto a 1-ml AG1-X8 resin (100–200 mesh, Bio-Rad) column. Columns were washed with 10 ml of 5 mM myo-inositol and 10 ml of 5 mM sodium borate/60 mM sodium formate. Total IPs were eluted with 3 ml of 0.1 M formic acid/1 M ammonium formate. Radioactivity was measured by liquid scintillation counting in Ecoscint cocktail.

Demonstration of Constitutive Activation:

Constitutive activity of the mutated 5-HT$_{2A}$ receptors is demonstrated by the fact that the mutated receptors exhibit all the hallmark characteristics established for constitutive activation: a showing of increased agonist affinity, increased agonist potency, and coupling to the G protein second messenger system in the absence of agonist.

Figures 10, 11:
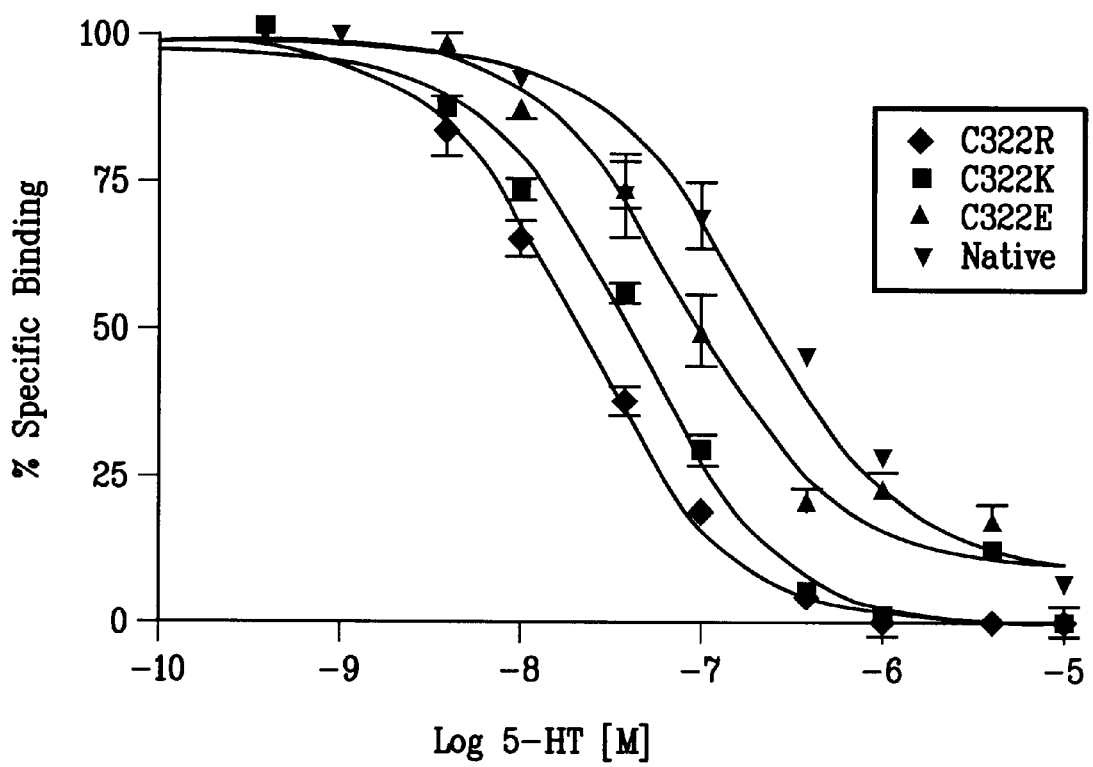
FIG. 10 shows the competition curves of 5-HT for $^3$H-ketanserin labeled native and mutant 5-HT$_{2A}$ receptors. 0.5 nM $^3$H-ketanserin was used to label the native and mutant receptors transiently transfected in COS-7 cells.
FIG. 11 shows the radioligand binding data of $^3$H-ketanserin labeled native and mutant 5-HT$_{2A}$ receptors in the presence of agonists and antagonists. 0.5 nM $^3$H-ketanserin was used to label the native and mutant 5-HT$_{2A}$ receptors expressed in COS-7 cells.

FIG. 10 shows the competition curves of 5-HT for $^3$H-ketanserin labeled native and mutant 5-HT$_{2A}$ receptors. 0.5nM $^3$H-ketanserin was used to label the native and mutant receptors transiently transfected in COS-7 cells. While the native receptor demonstrated a relatively low affinity for 5-HT ($K_i$=293 nM), the three mutant receptors displayed a high affinity for 5-HT with the cys→lys mutant exhibiting a 12-fold increase in affinity for 5-HT ($K_i$=25 nM), the cys→arg mutant exhibiting a 27-fold increase in affinity for 5-HT ($K_i$=11 nM). and the cys→glu mutant exhibiting a 3.4-fold increase in affinity for 5-HT ($K_i$=86 nM).

To determine whether other agonists would display a similar increase in affinity for the mutant receptors, two known agonists (DOM and DOB) were tested with both the native and cys→lys mutant. FIG. 11 shows the radioligand binding data of $^3$H-ketanserin labeled native and mutant 5-HT$_{2A}$ receptors in the presence of agonists and antagonists. 0.5 nM $^3$H-ketanserin was used to label the native and mutant 5-HT$_{2A}$ receptors expressed in COS-7 cells. The DOM and DOB agonists show increased affinity for the mutant receptor, as is seen for 5-HT. The $K_i$ for DOM shows a 5-fold increase, while the $K_i$ for DOB shows a 7.4-fold increase.

Figure 12:
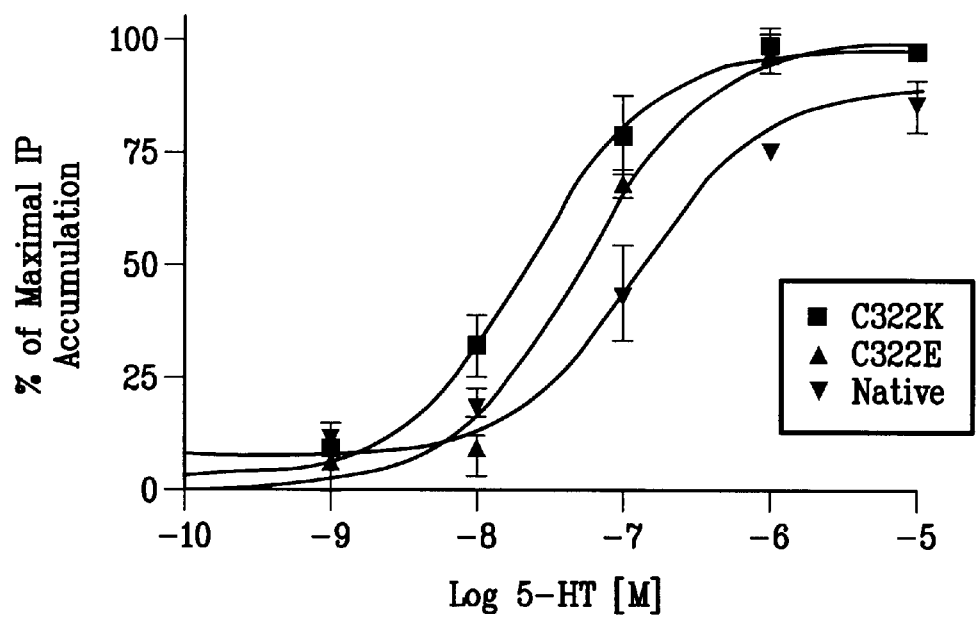
FIG. 12 shows the stimulation of IP production in COS-7 cells expressing native or mutant 5-HT$_{2A}$ receptors. IP production assays were performed using anion-exchange chromatography. The data are expressed as percent of maximal IP stimulation produced by 10 µM 5-HT.

To determine if the mutant 5-HT$_{2A}$ receptors would exhibit an increase in agonist potency relative to the native 5-HT$_{2A}$ receptor, 5-HT stimulation of the native and mutant 5-HT$_{2A}$ receptors was measured using an IP production assay. FIG. 12 shows the stimulation of IP production in COS-7 cells expressing native or mutant 5-HT$_{2A}$ receptors. Both the cys→lys and cys→glu mutant receptor curves exhibit a leftward shift away from the native curve in the 5-HT dose-response indicating that there was an increase in 5-HT potency at the mutant receptors. The cys→lys and cys→glu mutant receptors displayed EC$_{50}$ values of 25 nM and 61 nM, respectively, as compared to the native 5-HT$_{2A}$ receptor which had an EC$_{50}$ value of 152 nM.

Figure 13:
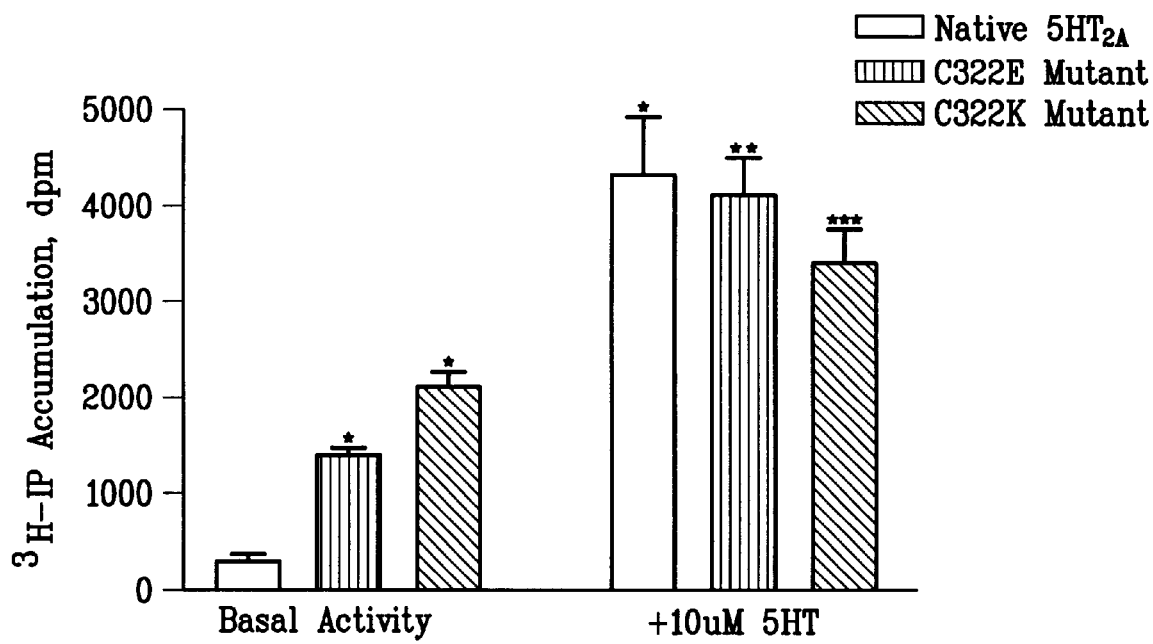
FIG. 13 shows the basal activity and 5-HT stimulation of the native and mutant 5-HT$_{2A}$ receptors. IP levels were measured in COS-7 cells with vector alone, native 5-HT$_{2A}$ receptors, or mutant 5-HT$_{2A}$ receptors. The data are expressed as dpms of IP stimulation minus basal levels of IP produced by vector. Basal activity of vector alone was typically 400 dpms.

FIG. 13 shows the basal activity and 5-HT stimulation of the native and mutant 5-HT$_{2A}$ receptors. As can be seen, both the cys→lys and the cys→glu mutant 5-HT$_{2A}$ receptors show dramatic increases in basal intracellular inositol phosphate (IP) accumulation compared to the native receptor. The cys→lys mutant receptor produced a 345% (8-fold) increase in IP levels over the vector control. The cys→glu mutant receptor produced a 158% (3.7-fold) increase in IP levels over the vector control. Upon the addition of 10 μM 5-HT, both the native and mutant receptors produced an additional increase in IP production. The basal activity of the cys→lys mutant was 48% of that of the maximally stimulated native 5-HT$_{2A}$ receptor. The basal activity of the cys→glu mutant was 31% of that of the maximally stimulated native 5-HT$_{2A}$ receptor.

In order to determine whether the above results were due to an increase in the number of expressed mutant receptors rather than to a change in the properties of the mutated receptors, saturation curves were generated. FIG. 14 shows a saturation analysis of $^3$H-ketanserin labeled native and cys→lys mutant receptors. B$_{MAX}$ values were determined by a BCA assay. For the native receptor the B$_{MAX}$=193+/−37 fmol/mg, while for the cys→lys mutant receptor, the B$_{MAX}$=218+/−31 fmol/mg. There is no significant difference in the B$_{MAX}$ values for the native and mutant receptors. The K$_D$ of $^3$H-ketanserin also did not differ between the native and mutant receptors. These data demonstrate that the results were not due to an increase in number of expressed mutant receptors compared to expressed native receptors.

Thus, the mutated 5-HT$_{2A}$ receptors meet all the criteria for constitutively activated receptors; they show a higher affinity for agonists; they show a higher potency for 5-HT; and they show activation (coupling) of the G protein second messenger pathway (IP production) even in the absence of agonist.

EXAMPLE 2

Constitutive Activation of 5-HT$_2$ Receptor

Materials and Methods for Site-directed Mutagenesis:

The rat 5-HT$_{2C}$ receptor cDNA was ligated into the mammalian expression vector pcDNA3 (Invitrogen) using BamHI (Gibco). This construct served as the native template for site-directed mutagenesis performed using Clonetech's Transformer kit. Mutagenic primers (Midland Certified Reagent Company) were designed complementary to amino acids #308–317 of the native 5-HT$_{2C}$ cDNA, while changing amino acid #312 from serine (TCC) to lysine (AAG) or phenylalanine (TTC). The same primers were designed to incorporate an Sca1 restriction site at amino acid #314 by changing the third codon in valine from GTC to GTA. The selection primer, complementary to bases 2081–3017 of the pcDNA3 vector, was designed to remove a unique Sma1 site by changing glycine at base 2093 from GGG to GGA. Phosphorylated primers were annealed to 10 ng of alkaline denatured plasmid template by heating to 65° C. for 5 minutes and cooling slowly to 37° C. Mutant DNA was synthesized using T4 DNA polymerase and ligase (Clonetech) by incubating for 1 hour at 37° C., followed by digestion with Sma1 (Gibco) and transformation of BMH71-18mutS *E. coli* (Clonetech). Plasmid was purified using the Wizard miniprep kit (Promega), digested with Sma1, and used to transform DH5α *E. coli* (Gibco). Individual colonies were isolated and plasmid DNA was digested with Sca1 to screen for S312K and S312F mutants (Gibco). S312K and S312F mutant plasmids contain an additional Sca1 site and appear as two bands (2.3 Kb and 7.6 Kb) when run on a 1% agarose gel. DNA sequencing (Sequenase version 2.1 kit USB, $^{35}$Sd-ATP NEN) was performed to confirm the incorporation of lysine or phenylalanine at amino acid #312. Sequencing reactions were run on a 5% acrylamide/bis (19:1) gel (BioRad) for 2 hours at 50° C., dried for 2 hours at 80° C., and exposed to Kodak Biomax MR film for 24 hours at −80° C.

In FIG. 36 (SEQ ID NO: 20) is shown the amino acid sequence of the 5-HT$_{2C}$ ser→lys mutant receptor with the mutated amino acid shown as a larger outlined letter. FIGS. 37A–37B (SEQ ID NO: 21) shows the resulting DNA sequence of the 5-HT$_{2C}$ ser→lys mutant receptor including the 5' and 3' untranslated regions with the translated codons underlined. The bases specifying the #312 lysine mutant are shown as larger outlined letters, and the starting and ending locations of the primer are also indicated. In addition to showing the mutated DNA sequence of the 5-HT$_{2C}$ ser→lys mutant receptor, FIGS. 38A–38B (SEQ ID NO: 22) shows the base, which was mutated to create the Sca1 site, as a larger outlined letter indicated with an arrow.

In FIG. 39 (SEQ ID NO: 23) is shown the amino acid sequence of the 5-HT$_{2C}$ ser→phe mutant receptor with the mutated amino acid shown as a larger outlined letter. FIGS. 40A–40B (SEQ ID NO: 24) shows the resulting DNA sequence of the 5-HT$_{2C}$ ser→phe mutant receptor including the 5' and 3' untranslated regions with the translated codons underlined. The bases specifying the #312 phenylalanine mutant are shown as larger outlined letters, and the starting and ending locations of the primer are also indicated. In addition to showing the mutated DNA sequence of the 5-HT$_{2C}$ ser→phe mutant receptor, FIG. 36 (SEQ ID NO: 25) shows the base, which was mutated to create the Sca1 site, as a larger outlined letter indicated with an arrow.

Cell Culture and Transfection:

COS-7 cells were grown in Dulbecco's Modified Eagle's Medium (DMEM, Sigma) with 10% fetal bovine serum (Sigma) in 5% CO$_2$ at 37° C. and subcultured 1:8 twice a week. Twenty-four hours prior to transfection, cells were seeded at 30% confluence in 100 mm dishes for radioligand binding assays or at 10$^5$ cells/well in 24 well cluster plates for PI assays. Cells were transfected with native or mutant 5-HT2$_c$ cDNA using Lipofectamine (Gibco). This was accomplished by combining 20 µl of lipofectamine with 2.5 µg plasmid per 100 mm dish or 2 µl lipofectamine and 0.25 µg plasmid per well. Transfections were performed in serum-free DMEM for 4 hours at 37° C.

Radioligand Binding:

Thirty-six hours after transfection, membranes were prepared from COS-7 cells by scraping and homogenizing in 50 mM Tris-HCl/5 mM MgCl$_2$/0.5 mM EDTA pH 7.4 (assay buffer) and centrifugation at 10,000×g for 30 minutes. Membranes were resuspended in assay buffer, homogenized and centrifuged again. Following resuspension in assay buffer, 1 ml membrane aliquots (approximately 10 µg protein measured by BCA assay) were added to each tube containing 1 ml of assay buffer with 1 nM $^3$H-mesulergine and competing drugs. 10 µM mianserin was used to define non-specific binding. Saturation experiments were performed using $^3$H-mesulergine (0.1 nM–5.0 nM) or $^3$H-5-HT (0.1 nM-30 nM) in the absence of presence of 10 µM GppNHp (RBI). Samples were incubated at 37° C. for 30 minutes, filtered on a Brandel cell harvester, and counted in Ecoscint cocktail (National Diagnostics) in a Beckman liquid scintillation counter at 40% efficiency.

Phosphatidylinositol Hydrolysis:

Inositol phosphate (IP) production was measured using a modified combination of the methods of Berridge et al., 1982 and Conn and Sanders-Bush 1985. Briefly, 24 hours after transfection, cells were washed with PBS and labeled with 0.25 µCi/well of $^3$H-myoinositol (NEN) in inositol-free/serum-free DMEM (Gibco) for 12 hours at 37° C. Following labeling, cells were washed with PBS and pre-incubated in inositol-free/serum-free DMEM with 10 mM LiCl and 10 µM pargyline (assay medium) for 10 minutes at 37° C. When antagonists were used they were added during the 10 minute preincubation period. 5-HT (Sigma), or assay medium alone, was added to each well and incubation continued for an additional 35 minutes (Westphal et al., 1995). Assay medium was removed and cells were lysed in 250 µl of stop solution (1M KOH/18 mM NaBorate/3.8 mM EDTA) and neutralized by adding 250 µl of 7.5% HCl. The contents of each well were extracted with 3 volumes of chloroform:methanol (1:2), centrifuged 5 minutes at 10,000×g, and the upper layer loaded onto a 1 ml AG1-X8 resin (100–200 mesh, BioRad) column. Columns were washed with 10 mls of 5 mM myoinositol and 10 mls of 5 mM NaBorate/60 mM NaFormate. Total IPs were eluted with 3 mls of 0.1M formic acid/1 M ammonium formate. Radioactivity was measured by liquid scintillation counting in Ecoscint cocktail.

Stable Transfection:

Although not yet fully characterized, it has been found possible to create a stable cell line expressing mutant receptors by the following method. The rat 5-HT$_{2C}$-cDNA (edited VSI isoform) was used as a template for site-directed mutagenesis to convert amino acid 312 from serine to lysine as previously described. Native and S312K 5-HT$_{2C}$ cDNAs were ligated into the BamHI/EcoRI site of the pZeoSV2+ mammalian expression vector (Invitrogen) containing the zeocin resistance gene. NIH3T3 cells (ATCC) were stably transfected using the high efficiency BES method. Briefly, cells were seeded at 5×10$^5$ cells/100 mm culture dish in complete medium (DMEM/10% FBS) and grown in 5% CO$_2$ at 370 overnight. Twenty micrograms of pZeoSV2/5-HT$_{2C}$ DNA (linearized with BglII) was mixed with 500 µl of 0.25M CaCl$_2$ and 500 µl of 2×BES solution (50 mM N,N-bis-2-hydroxyethyl-2-aminoethanesulfonic acid; 280 mM NaCl; 1.5 mM Na$_2$HPO$_4$; pH to 6.95) and incubated at 25° C. for 20 minutes. The solution was added dropwise on top of the cells. The cells were incubated for 20 hours at 35° C. in 3% CO$_2$, washed twice with PBS, complete medium replenished, and incubated for 48 hours at 37° C. in 5% CO$_2$. Cells were split 1:4 into complete medium containing 500 µg/ml zeocin. Individual colonies were isolated and tested for 5-HT$_{2C}$ receptor expression by 3H-mesulergine binding.

Demonstration of Constitutive Activation:

Constitutive activity of the mutated 5-HT$_{2C}$ receptors is demonstrated by the fact that the mutated receptors also exhibit all the hallmark characteristics established for constitutive activation: a showing of increased agonist affinity, increased agonist potency, and coupling to the G protein second messenger system in the absence of agonist.

Figures 15, 16:
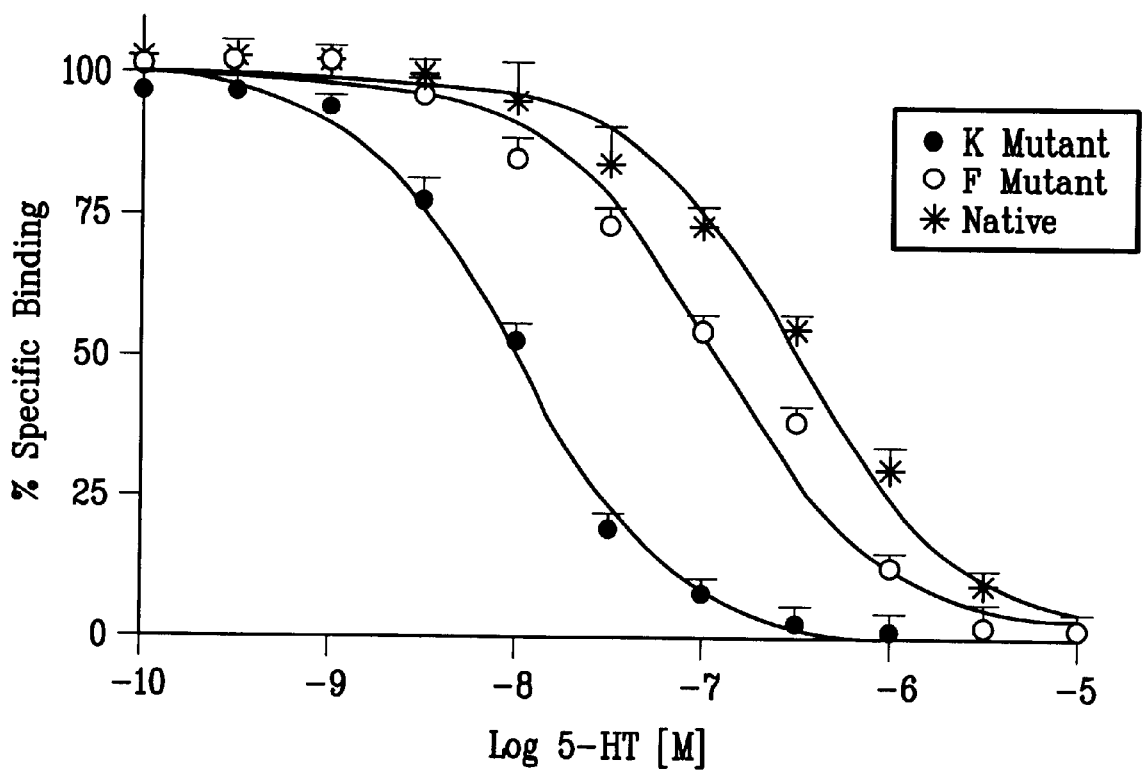
FIG. 15 shows the competition curves of 5-HT for $^3$H-mesulergine labeled native and mutant 5-HT$_{2C}$ receptors. 1 nM $^3$H-mesulergine was used to label the native and mutant receptors transiently transfected in COS-7 cells.
FIG. 16 shows the radioligand binding analysis of native and mutant 5-HT$_{2C}$ receptors. Native and mutant 5-HT$_{2C}$ receptors expressed in COS-7 cells were labeled with 1 nM $^3$H-mesulergine. 5-MT=5-methoxytryptamine.

FIG. 15 shows the competition curves of 5-HT for $^3$H-mesulergine labeled native and mutant 5-HT$_{2C}$ receptors. 0.5 nM $^3$H-mesulergine was used to label the native and mutant receptors transiently transfected in COS-7 cells. As shown in FIG. 15, the 5-HT competition isotherms for $^3$H-mesulergine labeled ser→lys and ser→phe mutant receptors display a marked leftward shift compared with native receptors. The affinity of 5-HT for ser→lys mutant receptors increased almost 30-fold from 203 nM in the native to 6.6 nM in the ser→lys mutant. Similarly, but on a smaller scale, the ser→phe mutation resulted in a 3-fold increase in 5-HT affinity to 76 nM.

To determine whether other agonists would display a similar increase in affinity for the mutant receptors, two known agonists, 5-methoxytryptamine and DOB were tested with the ser→lys mutant. FIG. 16 shows the radioligand binding analysis of native and mutant 5-HT$_{2C}$ receptors in the presence of agonists and antagonists. Native and mutant 5-HT$_{2C}$ receptors expressed in COS-7 cells were labeled with 1 nM 3H-mesulergine. The 5-MT and DOB agonists show increased affinity for the mutant receptor, as is seen for 5-HT. 5-methoxytryptamine and DOB display an 89-fold and 38-fold increase, respectively, in affinity for the ser→lys mutant receptors.

Figures 17, 18:
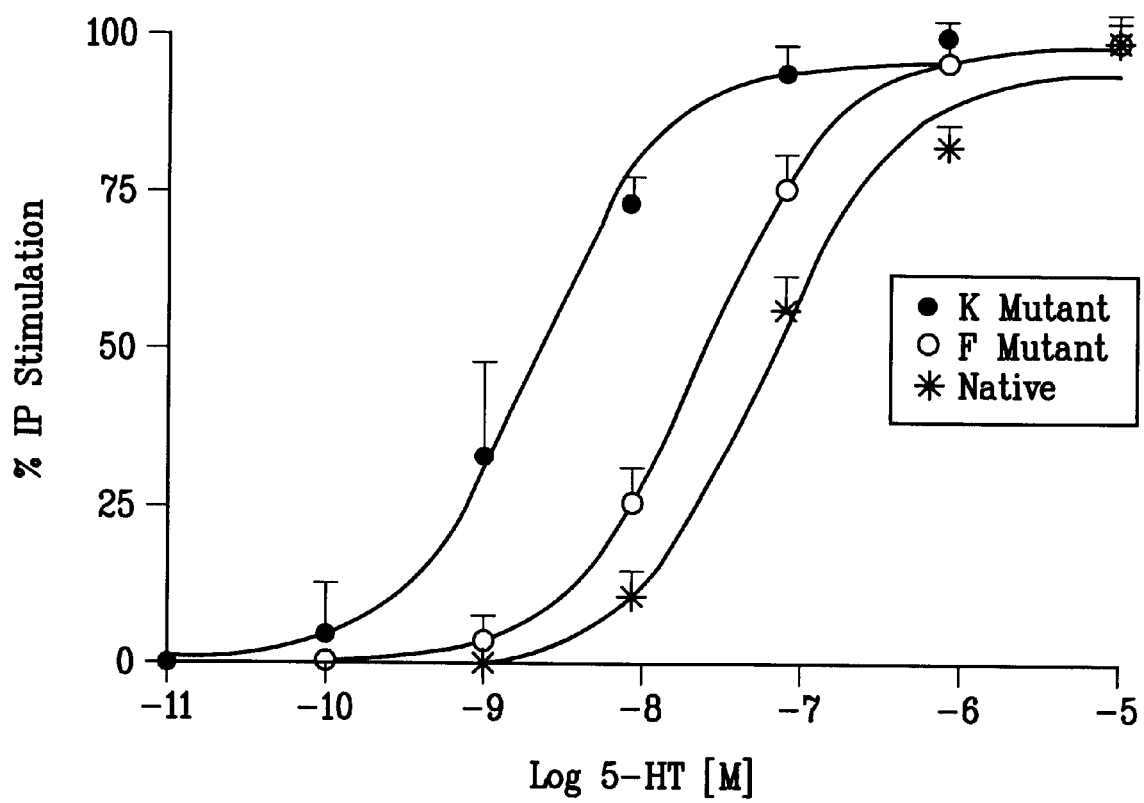
FIG. 17 shows the 5-HT stimulation of IP production in COS-7 cells transfected with the ser→lys or ser→phe mutated receptors. Cells were labeled with $^3$H-myoinositol and challenged with 5-HT (0.1 nM–10 nM). Total IP production was measured by anion exchange chromatography.
FIG. 18 shows the EC$_{50}$ values for the 5-HT stimulation of IP production in COS-7 cells transfected with native, mutant ser→lys receptor, and mutant ser→phe receptor.

To determine if the mutant 5-HT$_{2C}$ receptors would exhibit an increase in agonist potency relative to the native 5-HT$_{2C}$ receptor, 5-HT stimulation of the native and mutant 5-HT$_{2C}$ receptors was measured using an IP production assay. FIG. 17 shows the stimulation of IP production in COS-7 cells expressing native or mutant 5-HT$_{2C}$ receptors. Both the ser→lys and ser→phe mutant receptor curves exhibit a leftward shift away from the native curve in the 5-HT dose-response indicating that there was an increase in 5-HT potency for the mutant receptors. The shifts were similar in magnitude to the shifts in the 5-HT competition binding isotherms. FIG. 18 shows the 5-HT stimulation of IP production in COS-7 cells transfected with the ser→lys or ser→phe mutated receptors. As shown in FIG. 18, the EC$_{50}$ value for 5-HT mediated stimulation of IP production increased from 70 nM in cells transfected with native receptors to 2.7 nM in the ser→lys mutant and 28 nM in the ser→phe mutant.

Figure 19:
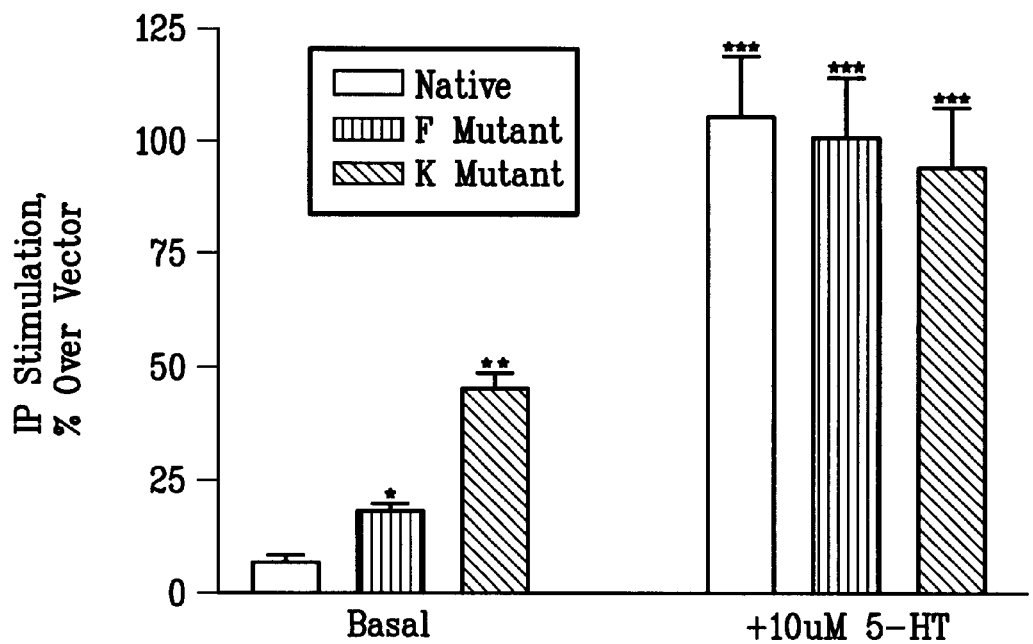
FIG. 19 shows the effect of the ser→lys and ser→phe mutations on basal levels of IP production by the mutated 5-HT$_{2C}$ receptors. IP levels were measured in COS-7 cells with vector alone, native 5-HT$_{2C}$ receptors, or mutant 5-HT$_{2C}$ receptors. The data are expressed as dpms of IP stimulation minus basal levels of IP produced by vector.

FIG. 19 shows the effect of the ser→lys and ser→phe mutations on basal levels of IP production by the mutated 5-HT$_{2C}$ receptors. Cells transfected with native 5-HT$_{2C}$ receptors displayed a small increase (9%, 225 dpm) in basal IP production over cells transfected with vector alone. Transfection with ser→lys and ser→phe mutant 5-HT$_{2C}$ receptors resulted in 5-fold and 2-fold increases, respectively, in basal levels of IP production when compared with cells expressing native 5-HT$_{2C}$ receptors. Basal levels of IP stimulated by ser→lys mutant receptors represented 50% of total IP production stimulated by native receptors in the presence of 10 μM 5-HT. 5-HT stimulated IP production 10 fold over basal levels in cells transfected with native receptors and 2-fold over basal levels in cells transfected with ser→lys mutant receptors. However, 5-HT elicited the same maximal IP response in cells transfected with native or mutant receptors.

Since receptor density can influence agonist binding affinity and potency in stimulating second messenger systems, saturation curves were generated. Therefore, $^3$H-mesulergine saturation analyses and Scatchard transformations were performed in parallel to control for variations in transfection efficiency and receptor expression levels. As shown in FIG. 18, the 5-HT$_{2C}$ receptor density was greater in cells transfected with native receptors than in cells transfected with either the ser→lys or the ser→phe mutant receptors. These data indicate that the increase in agonist binding affinity and potency of the mutated receptors did not result from increased receptor expression, but directly resulted from the mutations.

Thus, like the mutated 5-HT$_{2A}$ receptors, the mutated 5-HT$_{2C}$ receptors meet all the criteria for constitutively activated receptors; they show a higher affinity for agonists; they show a higher potency for 5-HT; and they show activation (coupling) of the G protein second messenger pathway (IP production) even in the absence of agonist.

Inverse Agonism at Constitutively Activated Serotonin Receptors

Figure 20:
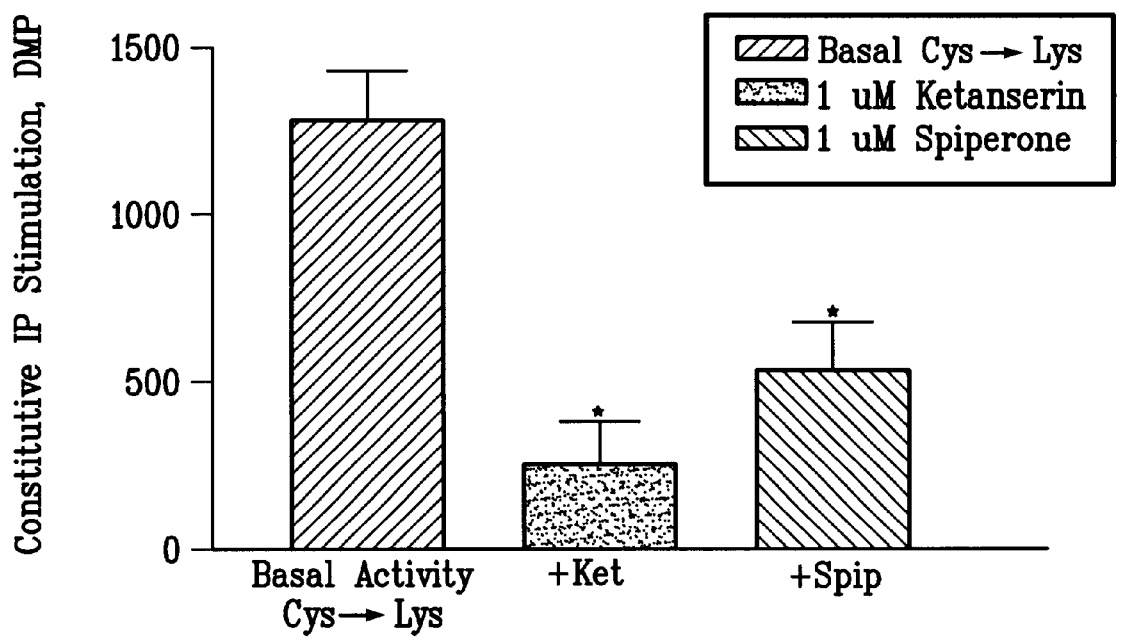
FIG. 20 shows the inverse agonist activity of spiperone and ketanserin on the mutated constitutively active 5-HT$_{2A}$ cys→lys receptor. Parallel transfections with the native 5-HT$_{2A}$ receptor were performed to determine native basal activity which was then subtracted from the mutant receptor basal activity to determine constitutive stimulation.

As noted above, the discovery and elucidation of the mechanisms of action of constitutively activated receptors has led to the recognition of a new class of receptor antagonists, identified as inverse agonists. The mutated 5-HT$_{2A}$ and 5-HT$_{2C}$ receptors of this invention were used to test the activity of known serotonin receptor antagonists. FIG. 11 shows the binding affinities of four known 5-HT$_{2A}$ antagonists to the native and cys→lys mutant 5-HT$_{2A}$ receptors. There is an apparent decease in the binding affinity of methysergide and mianserin at the mutant 5-HT$_{2A}$ receptors, but no change in binding affinity for spiperone and ketanserin. However, as shown in FIG. 20, both spiperone and ketanserin reversed the constitutive stimulation of IP production in cells expressing the mutant 5-HT$_{2A}$ receptor. Ketanserin and spiperone decreased the constitutive IP stimulation by 80% and 58% respectively.

Figure 21:
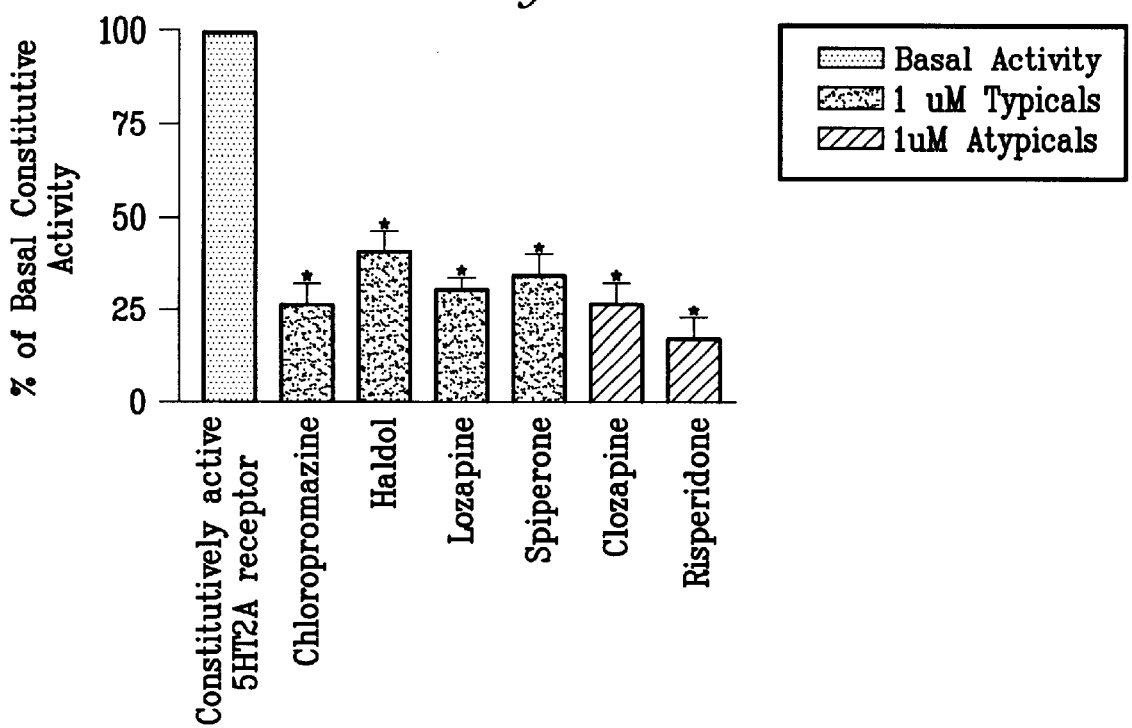
FIG. 21 shows the inverse agonist activity of chlorpromazine, haloperidol, loxapine, spiperone, clozapine and risperidone on the mutated constitutively active 5-HT$_{2A}$ cys→lys receptor.

Several antipsychotic drugs presently in use are thought to act at the 5-HT$_{2A}$ receptor. As shown in FIG. 21, all these drugs, chlorpromazine, haloperidol, loxapine, clozapine, and risperidone as well as spiperone reduce the constitutively activated IP basal activity of the mutated 5-HT$_{2A}$ receptor.

Figure 22:
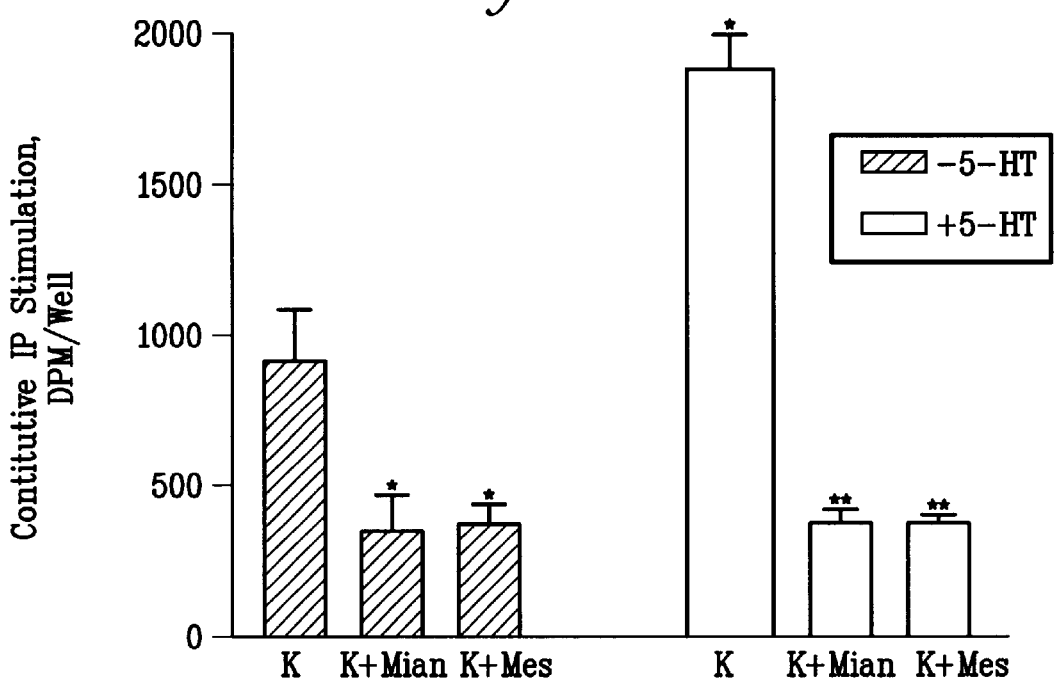
FIG. 22 shows the inverse agonist activity of mianserin and mesulergine on the mutated constitutively active 5-HT$_{2C}$ ser→lys receptor both in the presence and absence of 5-HT.

The constitutively active ser→lys mutated 5-HT$_{2C}$ receptor of this invention can also be used to screen compounds for inverse agonist activity. FIG. 22 shows that two classical 5-HT$_{2C}$ receptor antagonists, mianserin and mesulergine, exhibit inverse agonist activity by decreasing basal levels of PI hydrolysis associated with the constitutively active 5-HT$_{2C}$ mutant receptor. The inverse agonism of these compounds is apparent both in the presence and absence of serotonin.

The demonstration of inverse agonism at the mutated 5-HT$_{2A}$ and 5-HT$_{2C}$ receptors further characterizes the mutated serotonin receptors of this invention as being constitutively active. Not only have the 5-HT$_{2A}$ and 5-HT$_{2C}$ receptors been mutated to a constitutively active form, but a method has been disclosed for mutating all mammalian G protein-coupled monoamine receptors, including serotonin receptors, to a constitutively active form. Unlike the case of the M5 muscarinic acetylcholine receptor where mutations in the third cytoplasmic loop do not produce constitutive activation, the present invention clearly demonstrates that mutations in the third cytoplasmic loop of G protein-coupled serotonin receptors may be used to induce constitutive activation. Previously, third intracellular loop mutations near the transmembrane region had only been found to produce constitutively active receptors of the adrenergic type. With the present discoveries, it is now recognized that the alignment and positional mutation method of this invention is applicable to the general class of monoamine receptors of which the adrenergic and serotonin receptors are major subclasses. Further, based upon the present discoveries, it is expected that mutations may be introduced at other sites in the third cytoplasmic loop which will constitutively activate the G protein-coupled monoamine receptors including the serotonin receptors.

Additional Advances Enabled by the Discoveries of the Present Invention:

FIGS. 23A–23C (SEQ ID NO: 7) and 24 (SEQ ID NO: 8) show the DNA and amino acid sequences for the human 5-HT$_{2A}$ receptors. In FIGS. 23A–23C (SEQ ID NO: 7), it can be seen that the sixth transmembrane domain has the same WxPFFI conserved sequence (outlined type) as seen in the rat receptors. FIGS. 25A–25C (SEQ ID NO: 9) and 26 (SEQ ID NO: 10) show the DNA and amino acid sequences for the human 5-HT$_{2C}$ receptors. In FIG. 21A (SEQ ID NO: 9) it can be seen that the sixth transmembrane domain also has the same WxPFFI conserved sequence (outlined type) as seen in the rat receptors. Both of these human receptors may, therefore, be similarly aligned with the rat α1-adrenergic, 5-HT$_{2A}$, and 5-HT$_{2C}$ receptors to identify the amino acid positions which may be mutated to produce constitutively active human receptors following the methodologies of this invention.

Having identified mutations which constitutively activate the 5-HT$_{2A}$ and 5-HT$_{2C}$ serotonin receptors, it is now possible to create transgenic mammals incorporating these mutations using techniques well known in the art. This will provide an opportunity to study the physiological consequences of constitutive receptor activation and may lead to the development of novel therapeutic agents.

Those skilled in the art will recognize that various modifications, additions, substitutions and variations of the illustrative examples set forth herein can be made without departing from the spirit of the invention and are, therefore, considered within the scope of the invention.

REFERENCES

1. Cotecchia, S, Exum, S., Caron, M., and Lefkowitz, R. (1990) *Regions of the α$_1$-adrenergic receptor involved in coupling to phosphatidylinositol hydrolysis and enhanced sensitivity of biological function.* Proc. Natl. Acad. Sci. Vol 87, 2896–2900
2. Kjelsberg, M., Cotecchia, S., Ostrowski, J. Caron, M. and Lefkowitz, R. (1992) *Constitutive Activation of the α$_{1B}$-Adrenergic Receptor by All Amino Acid Substitutions at a Single Site.* J. Biol. Chem. Vol. 267, 1430–1433
3. Samama, P., Cotecchia, S., Costa, T. and Lefkowitz, R. (1993) *A Mutation-induced Activated State of the B$_2$-Adrenergic Receptor.* J. Biol. Chem. Vol 268, 4625–4636
4. Burstein, E., Spalding, T., Hill-Eubanks, D., & Brann, M. (1995) *Structure-Function of Muscarinic Receptor Coupling to G Proteins.* J. Biol. Chem. Vol 270, 3141–3146
5. The native rat 5-HT$_{2A}$ receptor cDNA was generously donated by Dr. David Julius of the University of California, San Francisco.
6. The native rat 5HT$_{2C}$ receptor cDNA was generously donated by Dr. Beth Hoffman of the National Institutes of Health.

What is claimed is:

1. A method of constitutively activating G protein-coupled mammalian serotonin receptors; wherein said serotonin receptors are human and rat, comprising the following steps:
   a. aligning a conserved amino acid sequence occurring in the sixth transmembrane domain of the serotonin receptor with the conserved amino acid sequence in the sixth transmembrane domain of the $\alpha_{1B}$-adrenergic receptor for which a constitutively activated form having a mutation in the third intracellular loop is known;
   b. identifying in the aligned receptor sequences the amino acid position in the serotonin receptor which corresponds to the amino acid position in the third intracellular loop which produced constitutive activation in the $\alpha_{1B}$-adrenergic receptor; and
   c. mutating, by site-directed mutagenesis, the identified amino acid position in the serotonin receptor so that a different amino acid is substituted for the amino acid occurring in the native serotonin receptor.

2. The method of claim 1 in which the G protein-coupled serotonin receptor is a rat 5-HT$_{2A}$ receptor.

3. The method of claim 1 in which the G protein-coupled serotonin receptor is a rat 5-HT$_{2C}$ receptor.

4. The method of claim 1 in which the conserved amino acid sequence within the sixth transmembrane domain used for the alignment is WxPFFI, where x represents that any amino acid may occur at that position.

5. The method of claim 1 in which the G protein-coupled serotonin receptor is a human 5HT$_{2A}$ receptor.

6. The method of claim 1 in which the G protein-coupled serotonin receptor is a human 5HT$_{2C}$ receptor.

7. A constitutively active rat 5-HT$_{2A}$ receptor in which the amino acid corresponding to the cysteine residue at position 322 of SEQ.ID.NO.:2 has been mutated from the cysteine found in the native receptor to an amino acid selected from the group consisting of lysine, glutamic acid, and arginine.

8. A constitutively active rat 5-HT$_{2C}$ receptor in which the amino acid corresponding to the serine residue at position 312 of SEQ.ID.NO.:4 has been mutated from the serine found in the native receptor to an amino acid selected from the group consisting of lysine and phenylalanine.

9. A DNA encoding a constitutive active rat 5-HT$_{2A}$ receptor in which the amino acid corresponding to the cysteine residue at position 322 of SEQ.ID.NO.:1 has been mutated from the cysteine found in the native receptor to an amino acid selected from the group consisting of lysine, glutamic acid, and arginine.

10. A DNA encoding a constitutively active rat 5-HT$_{2C}$ receptor in which the amino acid corresponding to the serine residue at position 312 of SEQ.ID.NO.:3 has been mutated from the serine found in the native receptor to an amino acid selected from the group consisting of lysine and phenylalanine.

11. The constitutively active rat 5-HT$_{2A}$ receptor coded by the DNA sequence specified in SEQ.ID.NO.:13.

12. The constitutively active rat 5-HT$_{2C}$ receptor coded by the DNA sequence specified in SEQ.ID.NO.:16.

13. The constitutively active rat 5-HT$_{2A}$ receptor coded by the DNA sequence specified in SEQ.ID.NO.:19.

14. The constitutively active rat 5-HT$_{2C}$ receptor coded by the DNA sequence specified in SEQ.ID.NO.:22.

15. The constitutively active rat 5-HT$_{2C}$ receptor coded by the DNA sequence specified in SEQ.ID.NO.:25.

16. A constitutively active human 5-HT$_{2A}$ receptor in which the amino acid corresponding to the cysteine residue at position 322 of SEQ.ID.NO.:8 has been mutated from the cysteine found in the native receptor to an amino acid selected from the group consisting of lysine, glutamic acid, and arginine.

17. A constitutively active human 5-HT$_{2C}$ receptor in which the amino acid corresponding to the serine residue at position 310 of SEQ.ID.NO.:10 has been mutated from the serine found in the native receptor to an amino acid selected from the group consisting of lysine and phenylalanine.

18. A DNA encoding a constitutively active human 5-HT$_{2A}$ receptor in which the amino acid corresponding to the cysteine residue at position 322 of SEQ.ID.NO.:7 has been mutated from the cysteine found in the native receptor to an amino acid selected from the group consisting of lysine, glutamic acid, and arginine.

19. A DNA encoding a constitutively active human 5-HT$_{2C}$ receptor in which the amino acid corresponding to the serine residue at position 310 of SEQ.ID.NO.:9 has been mutated from the serine found in the native receptor to an amino acid selected from the group consisting of lysine and phenylalanine.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
        (A) LENGTH: 1566 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

```
CCCAGGCTAT GAACCCCTAG TCTCTCCACA CTTCATCTGC TACAACTTCC GGCTTAGACA      60

TGGAAATTCT TTGTGAAGAC AATATCTCTC TGAGCTCAAT TCCAAACTCC TTAATGCAAT     120

TAGGTGATGG CCCGAGGCTC TACCATAATG ACTTCAACTC CAGAGATGCT AACACTTCGG     180

AAGCATCGAA CTGGACAATT GATGCTGAAA ACAGAACCAA CCTCTCCTGT GAAGGGTACC     240

TCCCACCGAC ATGCCTCTCC ATTCTTCATC TCCAGGAAAA AAACTGGTCT GCTTTATTGA     300

CAACTGTCGT GATTATTCTC ACCATTGCTG GAAATATACT GGTCATCATG GCAGTGTCCC     360

TAGAAAAAAA GCTGCAGAAT GCCACCAACT ATTTCCTGAT GTCACTTGCC ATAGCTGATA     420

TGCTGCTGGG TTTCCTTGTC ATGCCTGTGT CCATGTTAAC CATCCTGTAT GGGTACCGGT     480

GGCCTTTGCC TAGCAAGCTC TGTGCGATCT GGATTTACCT GGATGTGCTC TTTTCTACGG     540

CATCCATCAT GCACCTCTGC GCCATCTCCC TGGACCGCTA TGTCGCCATC CAGAACCCCA     600

TTCACCACAG CCGCTTCAAC TCCAGAACCA AAGCCTTCCT GAAAATCATT GCCGTGTGGA     660
```

```
CCATATCTGT AGGTATATCC ATGCCAATCC CAGTCTTTGG ACTACAGGAT GATTCGAAGG      720

TCTTTAAGGA GGGGAGCTGC CTGCTTGCCG ATGACAACTT TGTTCTCATA GGCTCTTTTG      780

TGGCATTTTT CATCCCCCTA ACCATCATGG TGATCACCTA CTTCCTGACT ATCAAGTCAC      840

TTCAGAAAGA AGCCACCTTG TGTGTGAGTG ACCTCAGCAC TCGAGCCAAA CTAGCCTCCT      900

TCAGCTTCCT CCCTCAGAGT TCTCTGTCAT CAGAAAAGCT CTTCCAACGG TCCATCCACA      960

GAGAGCCAGG CTCCTACGCA GGCCGAAGGA CGATGCAGTC CATCAGCAAT GAGCAAAAGG     1020

CGTGCAAGGT GCTGGGCATC GTGTTCTTCC TGTTTGTTGT AATGTGGTGC CCATTCTTCA     1080

TCACCAATAT CATGGCCGTC ATCTGCAAAG AATCCTGCAA TGAAAATGTC ATCGGAGCCC     1140

TGCTCAATGT GTTTGTCTGG ATTGGTTATC TCTCCTCAGC TGTCAATCCA CTGGTATATA     1200

CGTTGTTCAA TAAAACTTAT AGGTCCGCCT TCTCAAGGTA CATTCAGTGT CAGTACAAGG     1260

AAAACAGAAA GCCACTGCAG TTAATTTTAG TGAACACTAT ACCAGCATTG GCCTACAAGT     1320

CTAGTCAGCT CCAGGTGGGA CAGAAAAAGA ACTCACAGGA AGATGCTGAG CAGACAGTTG     1380

ATGACTGCTC CATGGTTACA CTGGGGAAAC AACAGTCGGA AGAGAATTGT ACAGACAATA     1440

TTGAAACCGT GAATGAAAAG GTTAGCTGTG TGTGATGAAC TGGATGCTAT GGCAATTGCC     1500

CAGGGCATGT GAACAAGGTT ATACCCATGT GTGTGGGGCG GGGATAAGGA GGCTGCAACA     1560

AATTAG                                                               1566

(2) INFORMATION FOR SEQ ID NO: 2:

(i) SEQUENCE CHARACTERISTICS:
        (A) LENGTH: 471 amino acids
        (B) TYPE: amino acid
        (C) STRANDEDNESS:
        (D) TOPOLOGY: Not Relevant (ii) MOLECULE TYPE: protein (xi) SEQUENCE DESCRIPTION: SEQ ID NO: 2:

Met Glu Ile Leu Cys Glu Asp Asn Ile Ser Leu Ser Ser Ile Pro Asn
1               5                   10                  15

Ser Leu Met Gln Leu Gly Asp Gly Pro Arg Leu Tyr His Asn Asp Phe
            20                  25                  30

Asn Ser Arg Asp Ala Asn Thr Ser Glu Ala Ser Asn Trp Thr Ile Asp
        35                  40                  45

Ala Glu Asn Arg Thr Asn Leu Ser Cys Glu Gly Tyr Leu Pro Pro Thr
    50                  55                  60

Cys Leu Ser Ile Leu His Leu Gln Glu Lys Asn Trp Ser Ala Leu Leu
65                  70                  75                  80

Thr Thr Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Ile Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
```

```
                  180               185               190
Phe Leu Lys Ile Ile Ala Val Trp Thr Ile Ser Val Gly Ile Ser Met
            195               200               205
Pro Ile Pro Val Phe Gly Leu Gln Asp Asp Ser Lys Val Phe Lys Glu
        210               215               220
Gly Ser Cys Leu Leu Ala Asp Asp Asn Phe Val Leu Ile Gly Ser Phe
225               230               235                   240
Val Ala Phe Phe Ile Pro Leu Thr Ile Met Val Ile Thr Tyr Phe Leu
                245               250               255
Thr Ile Lys Ser Leu Gln Lys Glu Ala Thr Leu Cys Val Ser Asp Leu
            260               265               270
Ser Thr Arg Ala Lys Leu Ala Ser Phe Ser Phe Leu Pro Gln Ser Ser
        275               280               285
Leu Ser Ser Glu Lys Leu Phe Gln Arg Ser Ile His Arg Glu Pro Gly
290               295               300
Ser Tyr Ala Gly Arg Arg Thr Met Gln Ser Ile Ser Asn Glu Gln Lys
305               310               315               320
Ala Cys Lys Val Leu Gly Ile Val Phe Phe Leu Phe Val Val Met Trp
                325               330               335
Cys Pro Phe Phe Ile Thr Asn Ile Met Ala Val Ile Cys Lys Glu Ser
            340               345               350
Cys Asn Glu Asn Val Ile Gly Ala Leu Leu Asn Val Phe Val Trp Ile
        355               360               365
Gly Tyr Leu Ser Ser Ala Val Asn Pro Leu Val Tyr Thr Leu Phe Asn
370               375               380
Lys Thr Tyr Arg Ser Ala Phe Ser Arg Tyr Ile Gln Cys Gln Tyr Lys
385               390               395               400
Glu Asn Arg Lys Pro Leu Gln Leu Ile Leu Val Asn Thr Ile Pro Ala
                405               410               415
Leu Ala Tyr Lys Ser Ser Gln Leu Gln Val Gly Gln Lys Lys Asn Ser
            420               425               430
Gln Glu Asp Ala Glu Gln Thr Val Asp Asp Cys Ser Met Val Thr Leu
        435               440               445
Gly Lys Gln Gln Ser Glu Glu Asn Cys Thr Asp Asn Ile Glu Thr Val
450               455               460
Asn Glu Lys Val Ser Cys Val
465               470

(2) INFORMATION FOR SEQ ID NO: 3:

(i) SEQUENCE CHARACTERISTICS:
        (A) LENGTH: 2246 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

GGCGCTCTGG TGCTCACTGA GGAAGCTTCC TTAGGTGTAC CGATCTTAAT GATTGAGCCC      60

TTGGAGCAGC AAGATTGTTA ATCTTGGTTG CTCCTTTGGC CTGTCTATCC CTTACCTTCC    120

TATTACATAT GAACTTTTCT TCGTTCTGCA CATCGATTGT CGTCGGCGTC GTGGAGATCG    180

TCGTGGTGCT CCGGTGGTGG TCTTCGTCCG CTTAGAATAG TGTAGTTAGT TAGGGGCCTT    240

CAAAGAAGAA AGAAGAAGCG ATTGGCGCGG AGAGATGCTG GAGGTGTCAG TTTCTATGCT    300
```

-continued

```
AGAGTAGGGT AGTGAAACAA TCCCCAGCCA AACCTTTCCG GGGGGCGCAG GTTGCCCACA    360

GGAGGTCGAC TTGCCGGCGC TGTCCTTCGC GCCGAGCTCC CTCCATCCTT CTTTCCGTCT    420

GCTGAGACGC AAGGTTGCGG CGCGCACGCT GAGCAGCGCA CTGACTGCCG CGGGCTCCGC    480

TGGGCGATTG CAGCCGAGTC CGTTTCTCGT CTAGCTGCCG CCGCGGCGAC CTGCCTGGTC    540

TTCCTCCCGG ACGCTAGCGG GTTGTCAACT ATTACCTGCA AGCATAGGCC AACGAACACC    600

TTCTTTCCAA ATTAATTGGA ATGAAACAAT TCTGTTAACT TCCTAATTCT CAGTTTGAAA    660

CTCTGGTTGC TTAAGCCTGA AGCAATCATG GTGAACCTTG GCAACGCGGT GCGCTCGCTC    720

CTGATGCACC TAATCGGCCT ATTGGTTTGG CAATTCGATA TTTCCATAAG TCCAGTAGCA    780

GCTATAGTAA CTGACACTTT TAATTCCTCC GATGGTGGAC GCTTGTTTCA ATTCCCGGAC    840

GGGGTACAAA ACTGGCCAGC ACTTTCAATC GTCGTGATTA AATCATGAC AATAGGGGGC     900

AACATTCTTG TTATCATGGC AGTAAGCATG GAGAAGAAAC TGCACAATGC AACCAATTAC    960

TTCTTAATGT CCCTAGCCAT TGCTGATATG CTGGTGGGAC TACTTGTCAT GCCCCTGTCC   1020

CTGCTTGCTA TTCTTTATGA TTATGTCTGG CCTTTACCTA GATATTTGTG CCCCGTCTGG   1080

ATTTCACTAG ATGTGCTATT TTCAACTGCG TCCATCATGC ACCTCTGCGC CATATCGCTG   1140

GACCGGTATG TAGCAATACG TAATCCTATT GAGCATAGCC GGTTCAATTC GCGGACTAAG   1200

GCCATCATGA AGATTGCCAT CGTTTGGGCA ATATCAATAG GAGTTTCAGT TCCTATCCCT   1260

GTGATTGGAC TGAGGGACGA AAGCAAAGTG TTCGTGAATA ACACCACGTG CGTGCTCAAT   1320

GACCCCAACT TCGTTCTCAT CGGGTCCTTC GTGGCATTCT TCATCCCGTT GACGATTATG   1380

GTGATCACCT ACTTCTTAAC GATCTACGTC CTGCGCCGTC AAACTCTGAT GTTACTTCGA   1440

GGTCACACCG AGGAGGAACT GGCTAATATG AGCCTGAACT TTCTGAACTG CTGCTGCAAG   1500

AAGAATGGTG GTGAGGAAGA GAACGCTCCG AACCCTAATC CAGATCAGAA ACCACGTCGA   1560

AAGAAGAAAG AAAAGCGTCC CAGAGGCACC ATGCAAGCTA TCAACAACGA AAAGAAAGCT   1620

TCCAAAGTCC TTGGCATTGT ATTCTTTGTG TTTCTGATCA TGTGGTGCCC GTTTTTCATC   1680

ACCAATATCC TGTCGGTTCT TTGTGGGAAG GCCTGTAACC AAAAGCTAAT GGAGAAGCTT   1740

CTCAATGTGT TTGTGTGGAT TGGCTATGTG TGTTCAGGCA TCAATCCTCT GGTGTACACT   1800

CTCTTTAATA AAATTTACCG AAGGGCTTTC TCTAAATATT TGCGCTGCGA TTATAAGCCA   1860

GACAAAAAGC CTCCTGTTCG ACAGATTCCT AGGGTTGCTG CCACTGCTTT GTCTGGGAGG   1920

GAGCTCAATG TTAACATTTA TCGGCATACC AATGAACGTG TGGCTAGGAA AGCTAATGAC   1980

CCTGAGCCTG GCATAGAGAT GCAGGTGGAG AACTTAGAGC TGCCAGTCAA CCCCTCTAAT   2040

GTGGTCAGCG AGAGGATTAG TAGTGTGTAA GCGAAGAGCA GCGCAGACTT CCTACAGGAA   2100

AGTTCCTGTA GGAAAGTCCT CCCCACCCCC CGTGATTTTC CTGTGAATCA TAACTAATGT   2160

AAATATTGCT GTGTGACAAG ACAGTGTTTT TATAAATAGC TTTGCAACCC TGTACTTTAC   2220

ATCATGCGTT AATAGTGAGA TTCGGG                                         2246
```

(2) INFORMATION FOR SEQ ID NO: 4:

(i) SEQUENCE CHARACTERISTICS:
        (A) LENGTH: 460 amino acids
        (B) TYPE: amino acid
        (C) STRANDEDNESS:
        (D) TOPOLOGY: Not Relevant (ii) MOLECULE TYPE: protein (xi) SEQUENCE DESCRIPTION: SEQ ID NO: 4:

-continued

```
Met Val Asn Leu Gly Asn Ala Val Arg Ser Leu Leu Met His Leu Ile
1               5                   10                  15

Gly Leu Leu Val Trp Gln Phe Asp Ile Ser Ile Ser Pro Val Ala Ala
                20                  25                  30

Ile Val Thr Asp Thr Phe Asn Ser Ser Asp Gly Gly Arg Leu Phe Gln
            35                  40                  45

Phe Pro Asp Gly Val Gln Asn Trp Pro Ala Leu Ser Ile Val Val Ile
    50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95

Ala Ile Ala Asp Met Leu Val Gly Leu Leu Val Met Pro Leu Ser Leu
                100                 105                 110

Leu Ala Ile Leu Tyr Asp Tyr Val Trp Pro Leu Pro Arg Tyr Leu Cys
            115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Ile Arg Asn Pro
145                 150                 155                 160

Ile Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
                180                 185                 190

Ile Gly Leu Arg Asp Glu Ser Lys Val Phe Val Asn Asn Thr Thr Cys
            195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Ala Asn Met Ser Leu Asn Phe Leu Asn Cys Cys Cys Lys Lys
                260                 265                 270

Asn Gly Gly Glu Glu Asn Ala Pro Asn Pro Asn Pro Asp Gln Lys
            275                 280                 285

Pro Arg Arg Lys Lys Lys Glu Lys Arg Pro Arg Gly Thr Met Gln Ala
    290                 295                 300

Ile Asn Asn Glu Lys Lys Ala Ser Lys Val Leu Gly Ile Val Phe Phe
305                 310                 315                 320

Val Phe Leu Ile Met Trp Cys Pro Phe Phe Ile Thr Asn Ile Leu Ser
                325                 330                 335

Val Leu Cys Gly Lys Ala Cys Asn Gln Lys Leu Met Glu Lys Leu Leu
                340                 345                 350

Asn Val Phe Val Trp Ile Gly Tyr Val Cys Ser Gly Ile Asn Pro Leu
            355                 360                 365

Val Tyr Thr Leu Phe Asn Lys Ile Tyr Arg Arg Ala Phe Ser Lys Tyr
    370                 375                 380

Leu Arg Cys Asp Tyr Lys Pro Asp Lys Pro Pro Val Arg Gln Ile
385                 390                 395                 400

Pro Arg Val Ala Ala Thr Ala Leu Ser Gly Arg Glu Leu Asn Val Asn
                405                 410                 415

Ile Tyr Arg His Thr Asn Glu Arg Val Ala Arg Lys Ala Asn Asp Pro
```

```
                    420             425             430
Glu Pro Gly Ile Glu Met Gln Val Glu Asn Leu Glu Leu Pro Val Asn
            435             440             445

Pro Ser Asn Val Val Ser Glu Arg Ile Ser Ser Val
450             455             460
```

(2) INFORMATION FOR SEQ ID NO: 5:

(i) SEQUENCE CHARACTERISTICS:
       (A) LENGTH: 515 amino acids
       (B) TYPE: amino acid
       (C) STRANDEDNESS:
       (D) TOPOLOGY: Not Relevant (ii) MOLECULE TYPE: protein (xi) SEQUENCE DESCRIPTION: SEQ ID NO: 5:

```
Met Asn Pro Asp Leu Asp Thr Gly His Asn Thr Ser Ala Pro Ala His
1               5                   10                  15

Trp Gly Glu Leu Lys Asp Asp Asn Phe Thr Gly Pro Asn Gln Thr Ser
                20                  25                  30

Ser Asn Ser Thr Leu Pro Gln Leu Asp Val Thr Arg Ala Ile Ser Val
            35                  40                  45

Gly Leu Val Leu Gly Ala Phe Ile Leu Phe Ala Ile Val Gly Asn Ile
        50                  55                  60

Leu Val Ile Leu Ser Val Ala Cys Asn Arg His Leu Arg Thr Pro Thr
65                  70                  75                  80

Asn Tyr Phe Ile Val Asn Leu Ala Ile Ala Asp Leu Leu Ser Phe
                85                  90                  95

Thr Val Leu Pro Phe Ser Ala Thr Leu Glu Val Leu Gly Tyr Trp Val
            100                 105                 110

Leu Leu Ser Phe Phe Cys Asp Ile Trp Ala Ala Val Asp Val Leu Cys
        115                 120                 125

Cys Thr Ala Ser Ile Leu Ser Leu Cys Ala Ile Ser Ile Asp Arg Tyr
    130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                165                 170                 175

Ser Ile Gly Pro Leu Leu Gly Trp Lys Glu Pro Ala Pro Asn Asp Asp
            180                 185                 190

Lys Glu Cys Gly Val Thr Glu Glu Pro Phe Tyr Ala Leu Phe Ser Ser
        195                 200                 205

Leu Gly Ser Phe Tyr Ile Pro Leu Ala Val Ile Leu Val Met Tyr Cys
    210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
                245                 250                 255

Ser Lys Asn Phe His Glu Asp Thr Leu Ser Ser Thr Lys Ala Lys Gly
            260                 265                 270

His Asn Pro Arg Ser Ser Ile Ala Val Lys Leu Phe Lys Phe Ser Arg
        275                 280                 285

Glu Lys Lys Ala Ala Lys Thr Leu Gly Ile Val Val Gly Met Phe Ile
    290                 295                 300

Leu Cys Trp Leu Pro Phe Phe Ile Ala Leu Pro Leu Gly Ser Leu Phe
```

```
305                 310                 315                 320
Ser Thr Leu Lys Pro Pro Asp Ala Val Phe Lys Val Val Phe Trp Leu
                325                 330                 335
Gly Tyr Phe Asn Ser Cys Leu Asn Pro Ile Ile Tyr Pro Cys Ser Ser
                340                 345                 350
Lys Glu Phe Lys Arg Ala Phe Met Arg Ile Leu Gly Cys Gln Cys Arg
                355                 360                 365
Gly Gly Arg Arg Arg Arg Arg Arg Arg Leu Gly Ala Cys Ala Tyr
        370                 375                 380
Thr Tyr Arg Pro Trp Thr Arg Gly Gly Ser Leu Glu Arg Ser Gln Ser
385                 390                 395                 400
Arg Lys Asp Ser Leu Asp Asp Ser Gly Ser Cys Met Ser Gly Thr Gln
                405                 410                 415
Arg Thr Leu Pro Ser Ala Ser Pro Ser Pro Gly Tyr Leu Gly Arg Gly
                420                 425                 430
Thr Gln Pro Pro Val Glu Leu Cys Ala Phe Pro Glu Trp Lys Pro Gly
                435                 440                 445
Ala Leu Leu Ser Leu Pro Glu Pro Pro Gly Arg Arg Gly Arg Leu Asp
        450                 455                 460
Ser Gly Pro Leu Phe Thr Phe Lys Leu Leu Gly Asp Pro Glu Ser Pro
465                 470                 475                 480
Gly Thr Glu Gly Asp Thr Ser Asn Gly Gly Cys Asp Thr Thr Thr Asp
                485                 490                 495
Leu Ala Asn Gly Gln Pro Gly Phe Lys Ser Asn Met Pro Leu Ala Pro
                500                 505                 510
Gly His Phe
    515

(2) INFORMATION FOR SEQ ID NO: 6:

(i) SEQUENCE CHARACTERISTICS:
        (A) LENGTH: 2108 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

GGGCGGACTT TAAAATGAAT CCCGATCTGG ACACCGGCCA CAACACATCA GCACCTGCCC      60

ACTGGGGAGA GTTGAAAGAT GACAACTTCA CTGGCCCCAA CCAGACCTCG AGCAACTCCA     120

CACTGCCCCA GCTGGACGTC ACCAGGGCCA TCTCTGTGGG CCTGGTGCTG GGCGCCTTCA     180

TCCTCTTTGC CATCGTGGGC AACATCTTGG TCATCCTGTC GGTGGCCTGC AACCGGCACC     240

TGCGGACGCC CACCAACTAC TTTATCGTCA ACCTGGCCAT TGCTGACCTG CTGTTGAGTT     300

TCACAGTACT GCCCTTCTCC GCTACCCTAG AAGTGCTTGG CTACTGGGTG CTGTTGAGTT     360

TCTTCTGTGA CATCTGGGCA GCGGTAGATG TCCTGTGCTG TACGGCCTCC ATCCTGAGCC     420

TATGTGCCAT CTCCATTGAC CGCTACATTG GGGTGCGATA CTCTCTGCAG TACCCCACGC     480

TGGTCACCCG CAGGAAGGCC ATCTTGGCGC TCCTCAGTGT GTGGGTCTTG TCCACGGTCA     540

TCTCCATCGG GCCTCTCCTT GGATGGAAAG AACCTGCGCC AATGATGAC AAAGAATGTG     600

GGGTCACCGA AGAACCCTTC TACGCCCTCT TTCCTCCCT GGGCTCCTTC TACATCCCGC     660

TCGCGGTCAT CCTGGTCATG TACTGCCGGG TCTACATCGT GGCCAAGAGG ACCACCAAGA     720

ATCTGGAGGC GGGAGTCATG AAGGAAATGT CCAACTCCAA GGAGCTGACC CTGAGGATCC     780
```

```
ACTCCAAGAA CTTTCATGAG GACACCCTCA GCAGTACCAA GGCCAAGGGC CACAACCCCA        840

GGAGTTCCAT AGCTGTCAAA CTTTTTAAGT TCTCCAGGGA AAAGAAAGCA GCCAAAACCT        900

TGGGCATTGT AGTCGGAATG TTCATCTTAT GTTGGCTCCC CTTCTTCATC GCTCTCCCGC        960

TTGGCTCCCT GTTCTCCACC CTAAAGCCCC CGGACGCCGT GTTCAAGGTG GTGTTCTGGC       1020

TGGGCTACTT CAACAGCTGC CTCAATCCCA TCATCTACCC GTGCTCCAGC AAGGAGTTCA       1080

AGCGCGCCTT CATGCGTATC CTTGGGTGCC AGTGCCGCGG TGGCCGCCGC CGCCGCCGCC       1140

GTCGCCGTCT AGGCGCGTGC GCTTACACCT ACCGGCCGTG GACCCGCGGC GGCTCGCTGG       1200

AGAGATCACA GTCGCGGAAG GACTCTCTGG ATGACAGCGG CAGCTGCATG AGCGGCACGC       1260

AGAGGACCCT GCCCTCGGCG TCGCCCAGCC CGGGCTACCT GGGTCGAGGA ACGCAGCCAC       1320

CCGTGGAGCT GTGCGCCTTC CCCGAGTGGA AACCCGGGGC GCTGCTCAGC TTGCCAGAGC       1380

CTCCTGGCCG CCGCGGCCGT CTCGACTCTG GGCCACTCTT CACCTTCAAG CTCCTGGGCG       1440

ATCCTGAGAG CCCGGGAACC GAAGGCGACA CCAGCAACGG GGGCTGCGAC ACCACGACCG       1500

ACCTGGCCAA CGGGCAGCCC GGCTTCAAGA GCAACATGCC CCTGGCGCCC GGGCACTTTT       1560

AGGGTCCCTT TTCATCCTCC CCCTCAACAC ACTCACACAT CGGGGTGGGG GAGAACACCA       1620

TCGTAGGGGC GGGAGGGCGC GTGGGGGGAG TGTCAGCCCT AGGTAGACAC AGGGTCGCAA       1680

GGGGACAAGG GGGGAGGGGG GCGGGGAGAG GGGCAGCTGC TTTTCTGGCA GGGGCATGGG       1740

TGCCAGGTAC AGCGAAGAGC TGGGCTGAGC ATGCTGAGAG CGTGGGGGGC CCCCCTAGTG       1800

GTTCCGGGAC TTAAGTCTCT CTCTCTTCTC TCTCTGTATA TACATAAAAT GAGTTCCTCT       1860

ATTCGTATTT ATCTGTGGGT ACACGTGCGT GTGTCTGTTC GGTGTACGTG TGGGCTGCAT       1920

GGGTGTGAGT GTGAGGCCTG CCCGCACGCG CGTGCCGGGG CAGAGCGAGT GCGCCCCTG       1980

GTGACGTCCA GGTGTGTTGT TTGTCTCTTG ACTTTGTACC TCTCAAGCCC CTCCCTGTTC       2040

TCTAGTCAAT GCTGGCACTT TGATAGGATC GGAAAACAAG TCAGATATTA AAGATCATTT       2100

CTCCTGTG                                                              2108

(2) INFORMATION FOR SEQ ID NO: 7:

(i) SEQUENCE CHARACTERISTICS:
        (A) LENGTH: 3016 base pairs
        (B) TYPE: nucleic acid
        (C) STRANDEDNESS: single
        (D) TOPOLOGY: Not Relevant (ii) MOLECULE TYPE: DNA (genomic)

(xi) SEQUENCE DESCRIPTION: SEQ ID NO: 7:

GAATTCGGGT GAGCCAGCTC CGGGAGAACA GCATGTACAC CAGCCTCAGT GTTACAGAGT         60

GTGGGTACAT CAAGGTGAAT GGTGAGCAGA AACTATAACC TGTTAGTCCT TCTACACCTC        120

ATCTGCTACA AGTTCTGGCT TAGACATGGA TATTCTTTGT GAAGAAAATA CTTCTTTGAG        180

CTCAACTACG AACTCCCTAA TGCAATTAAA TGATGACACC AGGCTCTACA GTAATGACTT        240

TAACTCTGGA GAAGCTAACA CTTCTGATGC ATTTAACTGG ACAGTCGACT CTGAAAATCG        300

AACCAACCTT TCCTGTGAAG GGTGCCTCTC ACCGTCGTGT CTCTCCTTAC TTCATCTCCA        360

GGAAAAAAAC TGGTCTGCTT TACTGACAGC CGTAGTGATT ATTCTAACTA TTGCTGGAAA        420

CATACTCGTC ATCATGGCAG TGTCCCTAGA GAAAAAGCTG CAGAATGCCA CCAACTATTT        480

CCTGATGTCA CTTGCCATAG CTGATATGCT GCTGGGTTTC CTTGTCATGC CCGTGTCCAT        540

GTTAACCATC CTGTATGGGT ACCGGTGGCC TCTGCCGAGC AAGCTTTGTG CAGTCTGGAT        600
```

```
TTACCTGGAC GTGCTCTTCT CCACGGCCTC CATCATGCAC CTCTGCGCCA TCTCGCTGGA    660
CCGCTACGTC GCCATCCAGA ATCCCATCCA CCACAGCCGC TTCAACTCCA GAACTAAGGC    720
ATTTCTGAAA ATCATTGCTG TTTGGACCAT ATCAGTAGGT ATATCCATGC CAATACCAGT    780
CTTTGGGCTA CAGGACGATT CGAAGGTCTT TAAGGAGGGG AGTTGCTTAC TCGCCGATGA    840
TAACTTTGTC CTGATCGGCT CTTTTGTGTC ATTTTTCATT CCCTTAACCA TCATGGTGAT    900
CACCTACTTT CTAACTATCA AGTCACTCCA GAAAGAAGCT ACTTTGTGTG TAAGTGATCT    960
TGGCACACGG GCCAAATTAG CTTCTTTCAG CTTCCTCCCT CAGAGTTCTT TGTCTTCAGA   1020
AAAGCTCTTC CAGCGGTCGA TCCATAGGGA GCCAGGGTCC TACACAGGCA GGAGGACTAT   1080
GCAGTCCATC AGCAATGAGC AAAAGGCATG CAAGGTGCTG GGCATCGTCT TCTTCCTGTT   1140
TGTGGTGATG TGGTGCCCTT TCTTCATCAC AAACATCATG GCCGTCATCT GCAAAGAGTC   1200
CTGCAATGAG GATGTCATTG GGCCCTGCT CAATGTGTTT GTTTGGATCG TTATCTCTC    1260
TTCAGCAGTC AACCCACTAG TCTACACACT GTTCAACAAG ACCTATAGGT CAGCCTTTTC   1320
ACGGTATATT CAGTGTCAGT ACAAGGAAAA CAAAAAACCA TTGCAGTTAA TTTTAGTGAA   1380
CACAATACCG GCTTTGGCCT ACAAGTCTAG CCAACTTCAA ATGGGACAAA AAAGAATTC    1440
AAAGCAAGAT GCCAAGACAA CAGATAATGA CTGCTCAATG GTTGCTCTAG GAAAGCAGCA   1500
TTCTGAAGAG GCTTCTAAAG ACAATAGCGA CGGAGTGAAT GAAAAGGTGA GCTGTGTGTG   1560
ATAGGCTAGT TGCCGTGGCA ACTGTGGAAG GCACACTGAG CAAGTTTTCA CCTATCTGGA   1620
AAAAAAAAAT ATGAGATTGG AAAAAATTAG ACAAGTCTAG TGGAACCAAC GATCATATCT   1680
GTATGCCTCA TTTTATTCTG TCAATGAAAA GCGGGGTTCA ATGCTACAAA ATGTGTGCTT   1740
GGAAAATGTT CTGACAGCAT TTCAGCTGTG AGCTTTCTGA TACTTATTTA TAACATTGTA   1800
AATGATATGT CTTTAAAATG ATTCACTTTT ATTGTATAAT TATGAAGCCC TAAGTAAATC   1860
TAAATTAACT TCTATTTTCA AGTGGAAACC TTGCTGCTAT GCTGTTCATT GATGACATGG   1920
GATTGAGTTG GTTACCTATT GCCGTAAATA AAAATAGCTA TAAATAGTGA AAATTTTATT   1980
GAATATAATG GCCTCTTAAA AATTATCTTT AAAACTTACT ATGGTATATA TTTTGAAAGG   2040
AGAAAAAAAA AAAGCCACTA AGGTCAGTGT TATAAAATCT GTATTGCTAA GATAATTAAA   2100
TGAAATACTT GACAACATTT TTCATAGATA CCATTTTGAA ATATTCACAA GGTTGCTGGC   2160
ATTTGCTGCA TTTCAAGTTA ATTCTCAGAA GTGAAAAGA CTTCAAATGT TATTCAATAA    2220
CTATTGCTGC TTTCTCTTCT ACTTCTTGTG CTTTACTCTG AATTTCCAGT GTGGTCTTGT   2280
TTAATATTTG TTCCTCTAGG TAAACTAGCA AAAGGATGAT TTAACATTAC CAAATGCCTT   2340
TCTAGCAATT GCTTCTCTAA AACAGCACTA TCGAGGTATT TGGTAACTTG CTGTGAAATG   2400
ACTGCATCAT GCATGCACTC TTTTGAGCAG TAAATGTATA TTGATGTAAC TGTGTCAGGA   2460
TTGAGGATGA ACTCAGGTTT CCGGCTACTG ACAGTGGTAG AGTCCTAGGA CATCTCTGTA   2520
AAAAGCAGGT GACTTTCCTA TGACACTCAT CAGGTAAACT GATGCTTTCA GATCCATCGG   2580
TTTATACTAT TTATTAAAAC CATTCTGCTT GGTTCCACAA TCATCTATTG AGTGTACATT   2640
TATGTGTGAA GCAAATTTCT AGATATGAGA AATATAAAAA TAATTAAAAC AAAATCCTTG   2700
CCTTCAAACG AAATGGCTCG GCCAGGCACG GAGGCTCGTG CATGTAATCC TAGCACTTTG   2760
GGAGGCTGAG ATGGGAGGAT CACTTGAGGC CAAGAGTTTG AGACCAACCT GGGTAACAAA   2820
GTGAGACCTC CCTGTCTCTA CAAAAAAAAT CAAAAAATTA TCTGATCCTT GTGGCACACA   2880
ACTGTGGTCC CAGCTACAGG GGAGGCTGAG ACGCAAGGAT CACTTGAGCC CAGAAGCTCA   2940
```

```
AGGCTGCAGT GAGCCAAGTT CACACCACTG CCATTTCCTC CTGGGCAACA GAGTGAGACC    3000

CTATCACCCC GAATTC                                                    3016
```

(2) INFORMATION FOR SEQ ID NO: 8:

(i) SEQUENCE CHARACTERISTICS:
        (A) LENGTH: 471 amino acids
        (B) TYPE: amino acid
        (C) STRANDEDNESS:
        (D) TOPOLOGY: Not Relevant (ii) MOLECULE TYPE: protein (xi) SEQUENCE DESCRIPTION: SEQ ID NO: 8:

```
Met Asp Ile Leu Cys Glu Glu Asn Thr Ser Leu Ser Ser Thr Thr Asn
1               5                   10                  15

Ser Leu Met Gln Leu Asn Asp Asp Thr Arg Leu Tyr Ser Asn Asp Phe
                20                  25                  30

Asn Ser Gly Glu Ala Asn Thr Ser Asp Ala Phe Asn Trp Thr Val Asp
            35                  40                  45

Ser Glu Asn Arg Thr Asn Leu Ser Cys Glu Gly Cys Leu Ser Pro Ser
50                  55                  60

Cys Leu Ser Leu Leu His Leu Gln Glu Lys Asn Trp Ser Ala Leu Leu
65                  70                  75                  80

Thr Ala Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
                100                 105                 110

Leu Met Ser Leu Ala Ile Ala Asp Met Leu Leu Gly Phe Leu Val Met
            115                 120                 125

Pro Val Ser Met Leu Thr Ile Leu Tyr Gly Tyr Arg Trp Pro Leu Pro
130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
            195                 200                 205

Pro Ile Pro Val Phe Gly Leu Gln Asp Asp Ser Lys Val Phe Lys Glu
210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
            260                 265                 270

Gly Thr Arg Ala Lys Leu Ala Ser Phe Ser Phe Leu Pro Gln Ser Ser
            275                 280                 285

Leu Ser Ser Glu Lys Leu Phe Gln Arg Ser Ile His Arg Glu Pro Gly
290                 295                 300

Ser Tyr Thr Gly Arg Arg Thr Met Gln Ser Ile Ser Asn Glu Gln Lys
305                 310                 315                 320

Ala Cys Lys Val Leu Gly Ile Val Phe Phe Leu Phe Val Val Met Trp
                325                 330                 335
```

```
Cys Pro Phe Phe Ile Thr Asn Ile Met Ala Val Ile Cys Lys Glu Ser
            340                 345                 350
Cys Asn Glu Asp Val Ile Gly Ala Leu Leu Asn Val Phe Val Trp Ile
            355                 360                 365
Gly Tyr Leu Ser Ser Ala Val Asn Pro Leu Val Tyr Thr Leu Phe Asn
            370                 375                 380
Lys Thr Tyr Arg Ser Ala Phe Ser Arg Tyr Ile Gln Cys Gln Tyr Lys
385                 390                 395                 400
Glu Asn Lys Lys Pro Leu Gln Leu Ile Leu Val Asn Thr Ile Pro Ala
                405                 410                 415
Leu Ala Tyr Lys Ser Ser Gln Leu Gln Met Gly Gln Lys Lys Asn Ser
            420                 425                 430
Lys Gln Asp Ala Lys Thr Thr Asp Asn Asp Cys Ser Met Val Ala Leu
            435                 440                 445
Gly Lys Gln His Ser Glu Glu Ala Ser Lys Asp Asn Ser Asp Gly Val
            450                 455                 460
Asn Glu Lys Val Ser Cys Val
465                 470

(2) INFORMATION FOR SEQ ID NO: 9:

(i) SEQUENCE CHARACTERISTICS:
        (A) LENGTH: 2733 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

GAATTCGGGA GCGTCCTCAG ATGCACCGAT CTTCCCGATA CTGCCTTTGG AGCGGCTAGA      60

TTGCTAGCCT TGGCTGCTCC ATTGGCCTGC CTTGCCCCTT ACCTGCCGAT TGCATATGAA    120

CTCTTCTTCT GTCTGTACAT CGTTGTCGTC GGAGTCGTCG CGATCGTCGT GGCGCTCGTG    180

TGATGGCCTT CGTCCGTTTA GAGTAGTGTA GTTAGTTAGG GGCCAACGAA GAAGAAAGAA    240

GACGCGATTA GTGCAGAGAT GCTGGAGGTG GTCAGTTACT AAGCTAGAGT AAGATAGCGG    300

AGCGAAAAGA GCCAAACCTA GCCGGGGGGC GCACGGTCAC CCAAAGGAGG TCGACTCGCC    360

GGCGCTTCCT ATCGCGCCGA GCTCCCTCCA TTCCTCTCCC TCCGCCGAGG CGCGAGGTTG    420

CGGCGCGCAG CGCAGCGCAG CTCAGCGCAC CGACTGCCGC GGGCTCCGCT GGGCGATTGC    480

AGCCGAGTCC GTTTCTCGTC TAGCTGCCGC CGCGGCGACC GCTGCCTGGT CTTCCTCCCG    540

GACGCTAGTG GGTTATCAGC TAACACCCGC GAGCATCTAT AACATAGGCC AACTGACGCC    600

ATCCTTCAAA AACAACTGTC TGGGAAAAAA AGAATAAAAA GTAGTGTGAG AGCAGAAAAC    660

GTGATTGAAA CACGACCAAT CTTTCTTCAG TGCCAAAGGG TGGAAAAGAA AGGATGATAT    720

GATGAACCTA GCCTGTTAAT TTCGTCTTCT CAATTTTAAA CTTTGGTTGC TTAAGACTGA    780

AGCAATCATG GTGAACCTGA GGAATGCGGT GCATTCATTC CTTGTGCACC TAATTGGCCT    840

ATTGGTTTGG CAATGTGATA TTTCTGTGAG CCCAGTAGCA GCTATAGTAA CTGACATTTT    900

CAATACCTCC GATGGTGGAC GCTTCAAATT CCCAGACGGG GTACAAAACT GGCCAGCACT    960

TTCAATCGTC ATCATAATAA TCATGACAAT AGGTGGCAAC ATCCTTGTGA TCATGGCAGT   1020

AAGCATGAAA AAGAAACTGC ACAATGCCAC CAATTACTTC TTAATGTCCC TAGCCATTGC   1080

TGATATGCTA GTGGGACTAC TTGTCATGCC CCTGTCTCTC CTGGCAATCC TTTATGATTA   1140
```

```
TGTCTGGCCA CTACCTAGAT ATTTGTGCCC CGTCTGGATT TCTTTAGATG TTTTATTTTC  1200

AACAGCGTCC ATCATGCACC TCTGCGCTAT ATCGCTGGAT CGGTATGTAG CAATACGTAA  1260

TCCTATTGAG CATAGCCGTT TCAATTCGCG GACTAAGGCC ATCATGAAGA TTGCTATTGT  1320

TTGGGCAATT TCTATAGGTG TATCAGTTCC TATCCCTGTG ATTGGACTGA GGGACGAAGA  1380

AAAGGTGTTC GTGAACAACA CGACGTGCGT GCTCAACGAC CCAAATTTCG TTCTTATTGG  1440

GTCCTTCGTA GCTTTCTTCA TACCGCTGAC GATTATGGTG ATTACGTATT GCCTGACCAT  1500

CTACGTTCTG CGCCGACAAG CTTTGATGTT ACTGCACGGC CACACCGAGG AACCGCCTGG  1560

ACTAAGTCTG GATTTCCTGA AGTGCTGCAA GAGGAATACG GCCGAGGAAG AGAACTCTGC  1620

AAACCCTAAC CAAGACCAGA ACGCACGCCG AAGAAAGAAG AAGGAGAGAC GTCCTAGGGG  1680

CACCATGCAG GCTATCAACA ATGAAAGAAA AGCTTCGAAA GTCCTTGGGA TTGTTTTCTT  1740

TGTGTTTCTG ATCATGTGGT GCCCATTTTT CATTACCAAT ATTCTGTCTG TTCTTTGTGA  1800

GAAGTCCTGT AACCAAAAGC TCATGGAAAA GCTTCTGAAT GTGTTTGTTT GGATTGGCTA  1860

TGTTTGTTCA GGAATCAATC CTCTGGTGTA TACTCTGTTC AACAAAATTT ACCGAAGGGC  1920

ATTCTCCAAC TATTTGCGTT GCAATTATAA GGTAGAGAAA AAGCCTCCTG TCAGGCAGAT  1980

TCCAAGAGTT GCCGCCACTG CTTTGTCTGG GAGGGAGCTT AATGTTAACA TTTATCGGCA  2040

TACCAATGAA CCGGTGATCG AGAAAGCCAG TGACAATGAG CCCGGTATAG AGATGCAAGT  2100

TGAGAATTTA GAGTTACCAG TAAATCCCTC CAGTGTGGTT AGCGAAAGGA TTAGCAGTGT  2160

GTGAGAAAGA ACAGCACAGT CTTTTCTACG GTACAAGCTA CATATGTAGG AAAATTTTCT  2220

TCTTTAATTT TTCTGTTGGT CTTAACTAAT GTAAATATTG CTGTCTGAAA AAGTGTTTTT  2280

ACATATAGCT TTGCAACCTT GTACTTTACA ATCATGCCTA CATTAGTGAG ATTTAGGGTT  2340

CTATATTTAC TGTTTATAAT AGGTGGAGAC TAACTTATTT TGATTGTTTG ATGAATAAAA  2400

TGTTTATTTT TGCTCTCCCT CCCTTCTTTC CTTCCTTTTT TCCTTTCTTC CTTCCTTTCT  2460

CTCTTTCTTT TGTGCATATG CAACGTTCA TGTTCATCTC AGGTGGCATT TGCAGGTGAC  2520

CAGAATGAGG CACATGACAG TGGTTATATT TCAACCACAC CTAAATTAAC AAATTCAGTG  2580

GACATTTGTT CTGGGTTAAC AGTAAATATA CACTTTACAT TCTTGCTCTG CTCATCTACA  2640

CATATAAACA CAGTAAGATA GGTTCTGCTT TCTGATACAT CTGTCAGTGA GTCAGAGGCA  2700

GAACCTAGTC TTGTTGTTCA TATAGGGGAA TTC                               2733
```

(2) INFORMATION FOR SEQ ID NO: 10:

(i) SEQUENCE CHARACTERISTICS:
        (A) LENGTH: 458 amino acids
        (B) TYPE: amino acid
        (C) STRANDEDNESS:
        (D) TOPOLOGY: Not Relevant (ii) MOLECULE TYPE: protein (xi) SEQUENCE DESCRIPTION: SEQ ID NO: 10:

```
Met Val Asn Leu Arg Asn Ala Val His Ser Phe Leu Val His Leu Ile
 1               5                  10                  15

Gly Leu Leu Val Trp Gln Cys Asp Ile Ser Val Ser Pro Val Ala Ala
                20                  25                  30

Ile Val Thr Asp Ile Phe Asn Thr Ser Asp Gly Gly Arg Phe Lys Phe
            35                  40                  45

Pro Asp Gly Val Gln Asn Trp Pro Ala Leu Ser Ile Val Ile Ile Ile
        50                  55                  60
```

-continued

```
Ile Met Thr Ile Gly Gly Asn Ile Leu Val Ile Met Ala Val Ser Met
 65                  70                  75                  80

Glu Lys Lys Leu His Asn Ala Thr Asn Tyr Phe Leu Met Ser Leu Ala
                 85                  90                  95

Ile Ala Asp Met Leu Val Gly Leu Leu Val Met Pro Leu Ser Leu Leu
            100                 105                 110

Ala Ile Leu Tyr Asp Tyr Val Trp Pro Leu Pro Arg Tyr Leu Cys Pro
        115                 120                 125

Val Trp Ile Ser Leu Asp Val Leu Phe Ser Thr Ala Ser Ile Met His
    130                 135                 140

Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
                165                 170                 175

Ile Val Trp Ala Ile Ser Ile Gly Val Ser Val Pro Ile Pro Val Ile
            180                 185                 190

Gly Leu Arg Asp Glu Glu Lys Val Phe Val Asn Asn Thr Thr Cys Val
        195                 200                 205

Leu Asn Asp Pro Asn Phe Val Leu Ile Gly Ser Phe Val Ala Phe Phe
    210                 215                 220

Ile Pro Leu Thr Ile Met Val Ile Thr Tyr Cys Leu Thr Ile Tyr Val
225                 230                 235                 240

Leu Arg Arg Gln Ala Leu Met Leu Leu His Gly His Thr Glu Glu Pro
                245                 250                 255

Pro Gly Leu Ser Leu Asp Phe Leu Lys Cys Cys Lys Arg Asn Thr Ala
            260                 265                 270

Glu Glu Glu Asn Ser Ala Asn Pro Asn Gln Asp Gln Asn Ala Arg Arg
        275                 280                 285

Arg Lys Lys Lys Glu Arg Arg Pro Arg Gly Thr Met Gln Ala Ile Asn
    290                 295                 300

Asn Glu Arg Lys Ala Ser Lys Val Leu Gly Ile Val Phe Phe Val Phe
305                 310                 315                 320

Leu Ile Met Trp Cys Pro Phe Phe Ile Thr Asn Ile Leu Ser Val Leu
                325                 330                 335

Cys Glu Lys Ser Cys Asn Gln Lys Leu Met Glu Lys Leu Leu Asn Val
            340                 345                 350

Phe Val Trp Ile Gly Tyr Val Cys Ser Gly Ile Asn Pro Leu Val Tyr
        355                 360                 365

Thr Leu Phe Asn Lys Ile Tyr Arg Arg Ala Phe Ser Asn Tyr Leu Arg
    370                 375                 380

Cys Asn Tyr Lys Val Glu Lys Lys Pro Pro Val Arg Gln Ile Pro Arg
385                 390                 395                 400

Val Ala Ala Thr Ala Leu Ser Gly Arg Glu Leu Asn Val Asn Ile Tyr
                405                 410                 415

Arg His Thr Asn Glu Pro Val Ile Glu Lys Ala Ser Asp Asn Glu Pro
            420                 425                 430

Gly Ile Glu Met Gln Val Glu Asn Leu Glu Leu Pro Val Asn Pro Ser
        435                 440                 445

Ser Val Val Ser Glu Arg Ile Ser Val
    450                 455
```

(2) INFORMATION FOR SEQ ID NO: 11:

(i) SEQUENCE CHARACTERISTICS:

(A) LENGTH: 471 amino acids
(B) TYPE: amino acid
(C) STRANDEDNESS:
(D) TOPOLOGY: Not Relevant (ii) MOLECULE TYPE: protein (xi) SEQUENCE DESCRIPTION: SEQ ID NO: 11:

```
Met Glu Ile Leu Cys Glu Asp Asn Ile Ser Leu Ser Ser Ile Pro Asn
  1               5                  10                  15

Ser Leu Met Gln Leu Gly Asp Gly Pro Arg Leu Tyr His Asn Asp Phe
             20                  25                  30

Asn Ser Arg Asp Ala Asn Thr Ser Glu Ala Ser Asn Trp Thr Ile Asp
         35                  40                  45

Ala Glu Asn Arg Thr Asn Leu Ser Cys Glu Gly Tyr Leu Pro Pro Thr
 50                  55                  60

Cys Leu Ser Ile Leu His Leu Gln Glu Lys Asn Trp Ser Ala Leu Leu
 65                  70                  75                  80

Thr Thr Val Val Ile Ile Leu Thr Ile Ala Gly Asn Ile Leu Val Ile
                 85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
            115                 120                 125

Pro Val Ser Met Leu Thr Ile Leu Tyr Gly Tyr Arg Trp Pro Leu Pro
            130                 135                 140

Ser Lys Leu Cys Ala Ile Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
            195                 200                 205

Pro Ile Pro Val Phe Gly Leu Gln Asp Asp Ser Lys Val Phe Lys Glu
            210                 215                 220

Gly Ser Cys Leu Leu Ala Asp Asp Asn Phe Val Leu Ile Gly Ser Phe
225                 230                 235                 240

Val Ala Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
            260                 265                 270

Ser Thr Arg Ala Lys Leu Ala Ser Phe Ser Phe Leu Pro Gln Ser Ser
            275                 280                 285

Leu Ser Ser Glu Lys Leu Phe Gln Arg Ser Ile His Arg Glu Pro Gly
            290                 295                 300

Ser Tyr Ala Gly Arg Arg Thr Met Gln Ser Ile Ser Asn Glu Gln Lys
305                 310                 315                 320

Ala Lys Lys Val Leu Gly Ile Val Phe Phe Leu Phe Val Val Met Trp
                325                 330                 335

Cys Pro Phe Phe Ile Thr Asn Ile Met Ala Val Ile Cys Lys Glu Ser
            340                 345                 350

Cys Asn Glu Asn Val Ile Gly Ala Leu Leu Asn Val Phe Val Trp Ile
            355                 360                 365

Gly Tyr Leu Ser Ser Ala Val Asn Pro Leu Val Tyr Thr Leu Phe Asn
```

```
                   370               375               380
Lys Thr Tyr Arg Ser Ala Phe Ser Arg Tyr Ile Gln Cys Gln Tyr Lys
385               390               395               400

Glu Asn Arg Lys Pro Leu Gln Leu Ile Leu Val Asn Thr Ile Pro Ala
                405               410               415

Leu Ala Tyr Lys Ser Ser Gln Leu Gln Val Gly Gln Lys Lys Asn Ser
                420               425               430

Gln Glu Asp Ala Glu Gln Thr Val Asp Asp Cys Ser Met Val Thr Leu
                435               440               445

Gly Lys Gln Gln Ser Glu Glu Asn Cys Thr Asp Asn Ile Glu Thr Val
450               455               460

Asn Glu Lys Val Ser Cys Val
465               470

(2) INFORMATION FOR SEQ ID NO: 12:

(i) SEQUENCE CHARACTERISTICS:
        (A) LENGTH: 1566 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

CCCAGGCTAT GAACCCCTAG TCTCTCCACA CTTCATCTGC TACAACTTCC GGCTTAGACA     60

TGGAAATTCT TTGTGAAGAC AATATCTCTC TGAGCTCAAT TCCAAACTCC TTAATGCAAT    120

TAGGTGATGG CCCGAGGCTC TACCATAATG ACTTCAACTC CAGAGATGCT AACACTTCGG    180

AAGCATCGAA CTGGACAATT GATGCTGAAA ACAGAACCAA CCTCTCCTGT GAAGGGTACC    240

TCCCACCGAC ATGCCTCTCC ATTCTTCATC TCCAGGAAAA AAACTGGTCT GCTTTATTGA    300

CAACTGTCGT GATTATTCTC ACCATTGCTG GAAATATACT GGTCATCATG GCAGTGTCCC    360

TAGAAAAAAA GCTGCAGAAT GCCACCAACT ATTTCCTGAT GTCACTTGCC ATAGCTGATA    420

TGCTGCTGGG TTTCCTTGTC ATGCCTGTGT CCATGTTAAC CATCCTGTAT GGGTACCGGT    480

GGCCTTTGCC TAGCAAGCTC TGTGCGATCT GGATTTACCT GGATGTGCTC TTTTCTACGG    540

CATCCATCAT GCACCTCTGC GCCATCTCCC TGGACCGCTA TGTCGCCATC CAGAACCCCA    600

TTCACCACAG CCGCTTCAAC TCCAGAACCA AAGCCTTCCT GAAAATCATT GCCGTGTGGA    660

CCATATCTGT AGGTATATCC ATGCCAATCC CAGTCTTTGG ACTACAGGAT GATTCGAAGG    720

TCTTTAAGGA GGGGAGCTGC CTGCTTGCCG ATGACAACTT TGTTCTCATA GGCTCTTTTG    780

TGGCATTTTT CATCCCCCTA ACCATCATGG TGATCACCTA CTTCCTGACT ATCAAGTCAC    840

TTCAGAAAGA AGCCACCTTG TGTGTGAGTG ACCTCAGCAC TCGAGCCAAA CTAGCCTCCT    900

TCAGCTTCCT CCCTCAGAGT TCTCTGTCAT CAGAAAAGCT CTTCCAACGG TCCATCCACA    960

GAGAGCCAGG CTCCTACGCA GGCCGAAGGA CGATGCAGTC CATCAGCAAT GAGCAAAAGG   1020

CGAAGAAGGT GCTGGGCATC GTGTTCTTCC TGTTTGTTGT AATGTGGTGC CCATTCTTCA   1080

TCACCAATAT CATGGCCGTC ATCTGCAAAG AATCCTGCAA TGAAAATGTC ATCGGAGCCC   1140

TGCTCAATGT GTTTGTCTGG ATTGGTTATC TCTCCTCAGC TGTCAATCCA CTGGTATATA   1200

CGTTGTTCAA TAAAACTTAT AGGTCCGCCT TCTCAAGGTA CATTCAGTGT CAGTACAAGG   1260

AAAACAGAAA GCCACTGCAG TTAATTTTAG TGAACACTAT ACCAGCATTG GCCTACAAGT   1320

CTAGTCAGCT CCAGGTGGGA CAGAAAAAGA ACTCACAGGA AGATGCTGAG CAGACAGTTG   1380
```

| ATGACTGCTC CATGGTTACA CTGGGGAAAC AACAGTCGGA AGAGAATTGT ACAGACAATA | 1440 |
| TTGAAACCGT GAATGAAAAG GTTAGCTGTG TGTGATGAAC TGGATGCTAT GGCAATTGCC | 1500 |
| CAGGGCATGT GAACAAGGTT ATACCCATGT GTGTGGGGCG GGGATAAGGA GGCTGCAACA | 1560 |
| AATTAG | 1566 |

(2) INFORMATION FOR SEQ ID NO: 13:

(i) SEQUENCE CHARACTERISTICS:
        (A) LENGTH: 1566 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

| CCCAGGCTAT GAACCCCTAG TCTCTCCACA CTTCATCTGC TACAACTTCC GGCTTAGACA | 60 |
| TGGAAATTCT TTGTGAAGAC AATATCTCTC TGAGCTCAAT TCCAAACTCC TTAATGCAAT | 120 |
| TAGGTGATGG CCCGAGGCTC TACCATAATG ACTTCAACTC CAGAGATGCT AACACTTCGG | 180 |
| AAGCATCGAA CTGGACAATT GATGCTGAAA ACAGAACCAA CCTCTCCTGT GAAGGGTACC | 240 |
| TCCCACCGAC ATGCCTCTCC ATTCTTCATC TCCAGGAAAA AAACTGGTCT GCTTTATTGA | 300 |
| CAACTGTCGT GATTATTCTC ACCATTGCTG GAAATATACT GGTCATCATG GCAGTGTCCC | 360 |
| TAGAAAAAAA GCTGCAGAAT GCCACCAACT ATTTCCTGAT GTCACTTGCC ATAGCTGATA | 420 |
| TGCTGCTGGG TTTCCTTGTC ATGCCTGTGT CCATGTTAAC CATCCTGTAT GGGTACCGGT | 480 |
| GGCCTTTGCC TAGCAAGCTC TGTGCGATCT GGATTTACCT GGATGTGCTC TTTTCTACGG | 540 |
| CATCCATCAT GCACCTCTGC GCCATCTCCC TGGACCGCTA TGTCGCCATC CAGAACCCCA | 600 |
| TTCACCACAG CCGCTTCAAC TCCAGAACCA AAGCCTTCCT GAAAATCATT GCCGTGTGGA | 660 |
| CCATATCTGT AGGTATATCC ATGCCAATCC CAGTCTTTGG ACTACAGGAT GATTCGAAGG | 720 |
| TCTTTAAGGA GGGGAGCTGC CTGCTTGCCG ATGACAACTT TGTTCTCATA GGCTCTTTTG | 780 |
| TGGCATTTTT CATCCCCCTA ACCATCATGG TGATCACCTA CTTCCTGACT ATCAAGTCAC | 840 |
| TTCAGAAAGA AGCCACCTTG TGTGTGAGTG ACCTCAGCAC TCGAGCCAAA CTAGCCTCCT | 900 |
| TCAGCTTCCT CCCTCAGAGT TCTCTGTCAT CAGAAAAGCT CTTCCAACGG TCCATCCACA | 960 |
| GAGAGCCAGG CTCCTACGCA GGCCGAAGGA CGATGCAGTC CATCAGCAAT GAGCAAAAGG | 1020 |
| CGAAGAAAGT ACTGGGCATC GTGTTCTTCC TGTTTGTTGT AATGTGGTGC CCATTCTTCA | 1080 |
| TCACCAATAT CATGGCCGTC ATCTGCAAAG AATCCTGCAA TGAAAATGTC ATCGGAGCCC | 1140 |
| TGCTCAATGT GTTTGTCTGG ATTGGTTATC TCTCCTCAGC TGTCAATCCA CTGGTATATA | 1200 |
| CGTTGTTCAA TAAAACTTAT AGGTCCGCCT TCTCAAGGTA CATTCAGTGT CAGTACAAGG | 1260 |
| AAAACAGAAA GCCACTGCAG TTAATTTTAG TGAACACTAT ACCAGCATTG GCCTACAAGT | 1320 |
| CTAGTCAGCT CCAGGTGGGA CAGAAAAAGA ACTCACAGGA AGATGCTGAG CAGACAGTTG | 1380 |
| ATGACTGCTC CATGGTTACA CTGGGGAAAC AACAGTCGGA AGAGAATTGT ACAGACAATA | 1440 |
| TTGAAACCGT GAATGAAAAG GTTAGCTGTG TGTGATGAAC TGGATGCTAT GGCAATTGCC | 1500 |
| CAGGGCATGT GAACAAGGTT ATACCCATGT GTGTGGGGCG GGGATAAGGA GGCTGCAACA | 1560 |
| AATTAG | 1566 |

(2) INFORMATION FOR SEQ ID NO: 14:

(i) SEQUENCE CHARACTERISTICS:

(A) LENGTH: 471 amino acids
(B) TYPE: amino acid
(C) STRANDEDNESS:
(D) TOPOLOGY: Not Relevant (ii) MOLECULE TYPE: protein (xi) SEQUENCE DESCRIPTION: SEQ ID NO: 14:

```
Met Glu Ile Leu Cys Glu Asp Asn Ile Ser Leu Ser Ser Ile Pro Asn
  1               5                  10                  15

Ser Leu Met Gln Leu Gly Asp Gly Pro Arg Leu Tyr His Asn Asp Phe
                 20                  25                  30

Asn Ser Arg Asp Ala Asn Thr Ser Glu Ala Ser Asn Trp Thr Ile Asp
             35                  40                  45

Ala Glu Asn Arg Thr Asn Leu Ser Cys Glu Gly Tyr Leu Pro Pro Thr
 50                  55                  60

Cys Leu Ser Ile Leu His Leu Gln Glu Lys Asn Trp Ser Ala Leu Leu
 65                  70                  75                  80

Thr Thr Val Val Ile Ile Leu Thr Ile Ala Gly Asn Ile Leu Val Ile
                 85                  90                  95

Met Ala Val Ser Leu Glu Lys Lys Leu Gln Asn Ala Thr Asn Tyr Phe
                100                 105                 110

Leu Met Ser Leu Ala Ile Ala Asp Met Leu Leu Gly Phe Leu Val Met
                115                 120                 125

Pro Val Ser Met Leu Thr Ile Leu Tyr Gly Tyr Arg Trp Pro Leu Pro
130                 135                 140

Ser Lys Leu Cys Ala Ile Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
                180                 185                 190

Phe Leu Lys Ile Ile Ala Val Trp Thr Ile Ser Val Gly Ile Ser Met
                195                 200                 205

Pro Ile Pro Val Phe Gly Leu Gln Asp Asp Ser Lys Val Phe Lys Glu
210                 215                 220

Gly Ser Cys Leu Leu Ala Asp Asp Asn Phe Val Leu Ile Gly Ser Phe
225                 230                 235                 240

Val Ala Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
                260                 265                 270

Ser Thr Arg Ala Lys Leu Ala Ser Phe Ser Phe Leu Pro Gln Ser Ser
                275                 280                 285

Leu Ser Ser Glu Lys Leu Phe Gln Arg Ser Ile His Arg Glu Pro Gly
                290                 295                 300

Ser Tyr Ala Gly Arg Arg Thr Met Gln Ser Ile Ser Asn Glu Gln Lys
305                 310                 315                 320

Ala Arg Lys Val Leu Gly Ile Val Phe Phe Leu Phe Val Val Met Trp
                325                 330                 335

Cys Pro Phe Phe Ile Thr Asn Ile Met Ala Val Ile Cys Lys Glu Ser
                340                 345                 350

Cys Asn Glu Asn Val Ile Gly Ala Leu Leu Asn Val Phe Val Trp Ile
                355                 360                 365

Gly Tyr Leu Ser Ser Ala Val Asn Pro Leu Val Tyr Thr Leu Phe Asn
```

```
Lys Thr Tyr Arg Ser Ala Phe Ser Arg Tyr Ile Gln Cys Gln Tyr Lys
385                 390                 395                 400

Glu Asn Arg Lys Pro Leu Gln Leu Ile Leu Val Asn Thr Ile Pro Ala
                405                 410                 415

Leu Ala Tyr Lys Ser Ser Gln Leu Gln Val Gly Gln Lys Lys Asn Ser
                420                 425                 430

Gln Glu Asp Ala Glu Gln Thr Val Asp Asp Cys Ser Met Val Thr Leu
                435                 440                 445

Gly Lys Gln Gln Ser Glu Glu Asn Cys Thr Asp Asn Ile Glu Thr Val
                450                 455                 460

Asn Glu Lys Val Ser Cys Val
465                 470
```

(2) INFORMATION FOR SEQ ID NO: 15:

(i) SEQUENCE CHARACTERISTICS:
        (A) LENGTH: 1566 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
CCCAGGCTAT GAACCCCTAG TCTCTCCACA CTTCATCTGC TACAACTTCC GGCTTAGACA      60
TGGAAATTCT TTGTGAAGAC AATATCTCTC TGAGCTCAAT TCCAAACTCC TTAATGCAAT     120
TAGGTGATGG CCCGAGGCTC TACCATAATG ACTTCAACTC CAGAGATGCT AACACTTCGG     180
AAGCATCGAA CTGGACAATT GATGCTGAAA ACAGAACCAA CCTCTCCTGT GAAGGGTACC     240
TCCCACCGAC ATGCCTCTCC ATTCTTCATC TCCAGGAAAA AAACTGGTCT GCTTTATTGA     300
CAACTGTCGT GATTATTCTC ACCATTGCTG GAAATATACT GGTCATCATG GCAGTGTCCC     360
TAGAAAAAAA GCTGCAGAAT GCCACCAACT ATTTCCTGAT GTCACTTGCC ATAGCTGATA     420
TGCTGCTGGG TTTCCTTGTC ATGCCTGTGT CCATGTTAAC CATCCTGTAT GGGTACCGGT     480
GGCCTTTGCC TAGCAAGCTC TGTGCGATCT GGATTTACCT GGATGTGCTC TTTTCTACGG     540
CATCCATCAT GCACCTCTGC GCCATCTCCC TGGACCGCTA TGTCGCCATC CAGAACCCCA     600
TTCACCACAG CCGCTTCAAC TCCAGAACCA AAGCCTTCCT GAAAATCATT GCCGTGTGGA     660
CCATATCTGT AGGTATATCC ATGCCAATCC CAGTCTTTGG ACTACAGGAT GATTCGAAGG     720
TCTTTAAGGA GGGGAGCTGC CTGCTTGCCG ATGACAACTT TGTTCTCATA GGCTCTTTTG     780
TGGCATTTTT CATCCCCCTA ACCATCATGG TGATCACCTA CTTCCTGACT ATCAAGTCAC     840
TTCAGAAAGA AGCCACCTTG TGTGTGAGTG ACCTCAGCAC TCGAGCCAAA CTAGCCTCCT     900
TCAGCTTCCT CCCTCAGAGT TCTCTGTCAT CAGAAAAGCT CTTCCAACGG TCCATCCACA     960
GAGAGCCAGG CTCCTACGCA GGCCGAAGGA CGATGCAGTC CATCAGCAAT GAGCAAAAGG    1020
CGAGGAAGGT GCTGGGCATC GTGTTCTTCC TGTTTGTTGT AATGTGGTGC CCATTCTTCA    1080
TCACCAATAT CATGGCCGTC ATCTGCAAAG AATCCTGCAA TGAAAATGTC ATCGGAGCCC    1140
TGCTCAATGT GTTTGTCTGG ATTGGTTATC TCTCCTCAGC TGTCAATCCA CTGGTATATA    1200
CGTTGTTCAA TAAAACTTAT AGGTCCGCCT TCTCAAGGTA CATTCAGTGT CAGTACAAGG    1260
AAAACAGAAA GCCACTGCAG TTAATTTTAG TGAACACTAT ACCAGCATTG GCCTACAAGT    1320
CTAGTCAGCT CCAGGTGGGA CAGAAAAAGA ACTCACAGGA AGATGCTGAG CAGACAGTTG    1380
```

```
ATGACTGCTC CATGGTTACA CTGGGGAAAC AACAGTCGGA AGAGAATTGT ACAGACAATA    1440

TTGAAACCGT GAATGAAAAG GTTAGCTGTG TGTGATGAAC TGGATGCTAT GGCAATTGCC    1500

CAGGGCATGT GAACAAGGTT ATACCCATGT GTGTGGGGCG GGGATAAGGA GGCTGCAACA    1560

AATTAG                                                              1566
```

(2) INFORMATION FOR SEQ ID NO: 16:

(i) SEQUENCE CHARACTERISTICS:
        (A) LENGTH: 1566 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

```
CCCAGGCTAT GAACCCCTAG TCTCTCCACA CTTCATCTGC TACAACTTCC GGCTTAGACA     60

TGGAAATTCT TTGTGAAGAC AATATCTCTC TGAGCTCAAT TCCAAACTCC TTAATGCAAT    120

TAGGTGATGG CCCGAGGCTC TACCATAATG ACTTCAACTC CAGAGATGCT AACACTTCGG    180

AAGCATCGAA CTGGACAATT GATGCTGAAA ACAGAACCAA CCTCTCCTGT GAAGGGTACC    240

TCCCACCGAC ATGCCTCTCC ATTCTTCATC TCCAGGAAAA AAACTGGTCT GCTTTATTGA    300

CAACTGTCGT GATTATTCTC ACCATTGCTG GAAATATACT GGTCATCATG GCAGTGTCCC    360

TAGAAAAAAA GCTGCAGAAT GCCACCAACT ATTTCCTGAT GTCACTTGCC ATAGCTGATA    420

TGCTGCTGGG TTTCCTTGTC ATGCCTGTGT CCATGTTAAC CATCCTGTAT GGGTACCGGT    480

GGCCTTTGCC TAGCAAGCTC TGTGCGATCT GGATTTACCT GGATGTGCTC TTTTCTACGG    540

CATCCATCAT GCACCTCTGC GCCATCTCCC TGGACCGCTA TGTCGCCATC CAGAACCCCA    600

TTCACCACAG CCGCTTCAAC TCCAGAACCA AAGCCTTCCT GAAAATCATT GCCGTGTGGA    660

CCATATCTGT AGGTATATCC ATGCCAATCC CAGTCTTTGG ACTACAGGAT GATTCGAAGG    720

TCTTTAAGGA GGGGAGCTGC CTGCTTGCCG ATGACAACTT TGTTCTCATA GGCTCTTTTG    780

TGGCATTTTT CATCCCCCTA ACCATCATGG TGATCACCTA CTTCCTGACT ATCAAGTCAC    840

TTCAGAAAGA AGCCACCTTG TGTGTGAGTG ACCTCAGCAC TCGAGCCAAA CTAGCCTCCT    900

TCAGCTTCCT CCCTCAGAGT TCTCTGTCAT CAGAAAAGCT CTTCCAACGG TCCATCCACA    960

GAGAGCCAGG CTCCTACGCA GGCCGAAGGA CGATGCAGTC CATCAGCAAT GAGCAAAAGG   1020

CGAGGAAGGT GCTGGGCATC GTGTTCTTCC TGTTTGTTGT AATGTGGTGC CCATTCTTCA   1080

TCACCAATAT CATGGCCGTC ATCTGCAAAG AATCCTGCAA TGAAAATGTC ATCGGAGCCC   1140

TGCTCAATGT GTTTGTCTGG ATTGGTTATC TCTCCTCAGC TGTCAATCCA CTGGTATATA   1200

CGTTGTTCAA TAAAACTTAT AGGTCCGCCT TCTCAAGGTA CATTCAGTGT CAGTACAAGG   1260

AAAACAGAAA GCCACTGCAG TTAATTTTAG TGAACACTAT ACCAGCATTG GCCTACAAGT   1320

CTAGTCAGCT CCAGGTGGGA CAGAAAAAGA ACTCACAGGA AGATGCTGAG CAGACAGTTG   1380

ATGACTGCTC CATGGTTACA CTGGGGAAAC AACAGTCGGA AGAGAATTGT ACAGACAATA   1440

TTGAAACCGT GAATGAAAAG GTTAGCTGTG TGTGATGAAC TGGATGCTAT GGCAATTGCC   1500

CAGGGCATGT GAACAAGGTT ATACCCATGT GTGTGGGGCG GGGATAAGGA GGCTGCAACA   1560

AATTAG                                                             1566
```

(2) INFORMATION FOR SEQ ID NO: 17:

(i) SEQUENCE CHARACTERISTICS:

(A) LENGTH: 471 amino acids
    (B) TYPE: amino acid
    (C) STRANDEDNESS:
    (D) TOPOLOGY: Not Relevant (ii) MOLECULE TYPE: protein (xi) SEQUENCE DESCRIPTION: SEQ ID NO: 17:

```
Met Glu Ile Leu Cys Glu Asp Asn Ile Ser Leu Ser Ser Ile Pro Asn
1               5                   10                  15

Ser Leu Met Gln Leu Gly Asp Gly Pro Arg Leu Tyr His Asn Asp Phe
            20                  25                  30

Asn Ser Arg Asp Ala Asn Thr Ser Glu Ala Ser Asn Trp Thr Ile Asp
        35                  40                  45

Ala Glu Asn Arg Thr Asn Leu Ser Cys Glu Gly Tyr Leu Pro Pro Thr
    50                  55                  60

Cys Leu Ser Ile Leu His Leu Gln Glu Lys Asn Trp Ser Ala Leu Leu
65                  70                  75                  80

Thr Thr Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Ile Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ala Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
            260                 265                 270

Ser Thr Arg Ala Lys Leu Ala Ser Phe Ser Phe Leu Pro Gln Ser Ser
        275                 280                 285

Leu Ser Ser Glu Lys Leu Phe Gln Arg Ser Ile His Arg Glu Pro Gly
    290                 295                 300

Ser Tyr Ala Gly Arg Arg Thr Met Gln Ser Ile Ser Asn Glu Gln Lys
305                 310                 315                 320

Ala Glu Lys Val Leu Gly Ile Val Phe Phe Leu Phe Val Val Met Trp
                325                 330                 335

Cys Pro Phe Phe Ile Thr Asn Ile Met Ala Val Ile Cys Lys Glu Ser
            340                 345                 350

Cys Asn Glu Asn Val Ile Gly Ala Leu Leu Asn Val Phe Val Trp Ile
        355                 360                 365

Gly Tyr Leu Ser Ser Ala Val Asn Pro Leu Val Tyr Thr Leu Phe Asn
```

```
                    370             375             380
Lys Thr Tyr Arg Ser Ala Phe Ser Arg Tyr Ile Gln Cys Gln Tyr Lys
385                 390             395             400

Glu Asn Arg Lys Pro Leu Gln Leu Ile Leu Val Asn Thr Ile Pro Ala
                405             410             415

Leu Ala Tyr Lys Ser Ser Gln Leu Gln Val Gly Gln Lys Lys Asn Ser
            420             425             430

Gln Glu Asp Ala Glu Gln Thr Val Asp Asp Cys Ser Met Val Thr Leu
        435             440             445

Gly Lys Gln Gln Ser Glu Glu Asn Cys Thr Asp Asn Ile Glu Thr Val
    450             455             460

Asn Glu Lys Val Ser Cys Val
465             470

(2) INFORMATION FOR SEQ ID NO: 18:

(i) SEQUENCE CHARACTERISTICS:
        (A) LENGTH: 1566 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

CCCAGGCTAT GAACCCCTAG TCTCTCCACA CTTCATCTGC TACAACTTCC GGCTTAGACA    60

TGGAAATTCT TTGTGAAGAC AATATCTCTC TGAGCTCAAT TCCAAACTCC TTAATGCAAT   120

TAGGTGATGG CCCGAGGCTC TACCATAATG ACTTCAACTC CAGAGATGCT AACACTTCGG   180

AAGCATCGAA CTGGACAATT GATGCTGAAA ACAGAACCAA CCTCTCCTGT GAAGGGTACC   240

TCCCACCGAC ATGCCTCTCC ATTCTTCATC TCCAGGAAAA AAACTGGTCT GCTTTATTGA   300

CAACTGTCGT GATTATTCTC ACCATTGCTG GAAATATACT GGTCATCATG GCAGTGTCCC   360

TAGAAAAAAA GCTGCAGAAT GCCACCAACT ATTTCCTGAT GTCACTTGCC ATAGCTGATA   420

TGCTGCTGGG TTTCCTTGTC ATGCCTGTGT CCATGTTAAC CATCCTGTAT GGGTACCGGT   480

GGCCTTTGCC TAGCAAGCTC TGTGCGATCT GGATTTACCT GGATGTGCTC TTTTCTACGG   540

CATCCATCAT GCACCTCTGC GCCATCTCCC TGGACCGCTA TGTCGCCATC CAGAACCCCA   600

TTCACCACAG CCGCTTCAAC TCCAGAACCA AAGCCTTCCT GAAAATCATT GCCGTGTGGA   660

CCATATCTGT AGGTATATCC ATGCCAATCC CAGTCTTTGG ACTACAGGAT GATTCGAAGG   720

TCTTTAAGGA GGGGAGCTGC CTGCTTGCCG ATGACAACTT TGTTCTCATA GGCTCTTTTG   780

TGGCATTTTT CATCCCCCTA ACCATCATGG TGATCACCTA CTTCCTGACT ATCAAGTCAC   840

TTCAGAAAGA AGCCACCTTG TGTGTGAGTG ACCTCAGCAC TCGAGCCAAA CTAGCCTCCT   900

TCAGCTTCCT CCCTCAGAGT TCTCTGTCAT CAGAAAAGCT CTTCCAACGG TCCATCCACA   960

GAGAGCCAGG CTCCTACGCA GGCCGAAGGA CGATGCAGTC CATCAGCAAT GAGCAAAAGG  1020

CGGAGAAGGT GCTGGGCATC GTGTTCTTCC TGTTTGTTGT AATGTGGTGC CCATTCTTCA  1080

TCACCAATAT CATGGCCGTC ATCTGCAAAG AATCCTGCAA TGAAAATGTC ATCGGAGCCC  1140

TGCTCAATGT GTTTGTCTGG ATTGGTTATC TCTCCTCAGC TGTCAATCCA CTGGTATATA  1200

CGTTGTTCAA TAAAACTTAT AGGTCCGCCT TCTCAAGGTA CATTCAGTGT CAGTACAAGG  1260

AAAACAGAAA GCCACTGCAG TTAATTTTAG TGAACACTAT ACCAGCATTG GCCTACAAGT  1320

CTAGTCAGCT CCAGGTGGGA CAGAAAAAGA ACTCACAGGA AGATGCTGAG CAGACAGTTG  1380
```

-continued

```
ATGACTGCTC CATGGTTACA CTGGGGAAAC AACAGTCGGA AGAGAATTGT ACAGACAATA    1440

TTGAAACCGT GAATGAAAAG GTTAGCTGTG TGTGATGAAC TGGATGCTAT GGCAATTGCC    1500

CAGGGCATGT GAACAAGGTT ATACCCATGT GTGTGGGGCG GGGATAAGGA GGCTGCAACA    1560

AATTAG                                                              1566
```

(2) INFORMATION FOR SEQ ID NO: 19:

(i) SEQUENCE CHARACTERISTICS:
        (A) LENGTH: 1566 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

```
CCCAGGCTAT GAACCCCTAG TCTCTCCACA CTTCATCTGC TACAACTTCC GGCTTAGACA      60

TGGAAATTCT TTGTGAAGAC AATATCTCTC TGAGCTCAAT TCCAAACTCC TTAATGCAAT     120

TAGGTGATGG CCCGAGGCTC TACCATAATG ACTTCAACTC CAGAGATGCT AACACTTCGG     180

AAGCATCGAA CTGGACAATT GATGCTGAAA ACAGAACCAA CCTCTCCTGT GAAGGGTACC     240

TCCCACCGAC ATGCCTCTCC ATTCTTCATC TCCAGGAAAA AAACTGGTCT GCTTTATTGA     300

CAACTGTCGT GATTATTCTC ACCATTGCTG GAAATATACT GGTCATCATG GCAGTGTCCC     360

TAGAAAAAAA GCTGCAGAAT GCCACCAACT ATTTCCTGAT GTCACTTGCC ATAGCTGATA     420

TGCTGCTGGG TTTCCTTGTC ATGCCTGTGT CCATGTTAAC CATCCTGTAT GGGTACCGGT     480

GGCCTTTGCC TAGCAAGCTC TGTGCGATCT GGATTTACCT GGATGTGCTC TTTTCTACGG     540

CATCCATCAT GCACCTCTGC GCCATCTCCC TGGACCGCTA TGTCGCCATC CAGAACCCCA     600

TTCACCACAG CCGCTTCAAC TCCAGAACCA AAGCCTTCCT GAAAATCATT GCCGTGTGGA     660

CCATATCTGT AGGTATATCC ATGCCAATCC CAGTCTTTGG ACTACAGGAT GATTCGAAGG     720

TCTTTAAGGA GGGGAGCTGC CTGCTTGCCG ATGACAACTT TGTTCTCATA GGCTCTTTTG     780

TGGCATTTTT CATCCCCCTA ACCATCATGG TGATCACCTA CTTCCTGACT ATCAAGTCAC     840

TTCAGAAAGA AGCCACCTTG TGTGTGAGTG ACCTCAGCAC TCGAGCCAAA CTAGCCTCCT     900

TCAGCTTCCT CCCTCAGAGT TCTCTGTCAT CAGAAAAGCT CTTCCAACGG TCCATCCACA     960

GAGAGCCAGG CTCCTACGCA GGCCGAAGGA CGATGCAGTC CATCAGCAAT GAGCAAAAGG    1020

CGGAGAAGGT ACTGGGCATC GTGTTCTTCC TGTTTGTTGT AATGTGGTGC CCATTCTTCA    1080

TCACCAATAT CATGGCCGTC ATCTGCAAAG AATCCTGCAA TGAAAATGTC ATCGGAGCCC    1140

TGCTCAATGT GTTTGTCTGG ATTGGTTATC TCTCCTCAGC TGTCAATCCA CTGGTATATA    1200

CGTTGTTCAA TAAAACTTAT AGGTCCGCCT TCTCAAGGTA CATTCAGTGT CAGTACAAGG    1260

AAAACAGAAA GCCACTGCAG TTAATTTTAG TGAACACTAT ACCAGCATTG GCCTACAAGT    1320

CTAGTCAGCT CCAGGTGGGA CAGAAAAAGA ACTCACAGGA AGATGCTGAG CAGACAGTTG    1380

ATGACTGCTC CATGGTTACA CTGGGGAAAC AACAGTCGGA AGAGAATTGT ACAGACAATA    1440

TTGAAACCGT GAATGAAAAG GTTAGCTGTG TGTGATGAAC TGGATGCTAT GGCAATTGCC    1500

CAGGGCATGT GAACAAGGTT ATACCCATGT GTGTGGGGCG GGGATAAGGA GGCTGCAACA    1560

AATTAG                                                              1566
```

(2) INFORMATION FOR SEQ ID NO: 20:

(i) SEQUENCE CHARACTERISTICS:

(A) LENGTH: 460 amino acids
(B) TYPE: amino acid
(C) STRANDEDNESS:
(D) TOPOLOGY: Not Relevant (ii) MOLECULE TYPE: protein (xi) SEQUENCE DESCRIPTION: SEQ ID NO: 20:

```
Met Val Asn Leu Gly Asn Ala Val Arg Ser Leu Leu Met His Leu Ile
1               5                   10                  15

Gly Leu Leu Val Trp Gln Phe Asp Ile Ser Ile Ser Pro Val Ala Ala
                20                  25                  30

Ile Val Thr Asp Thr Phe Asn Ser Ser Asp Gly Gly Arg Leu Phe Gln
            35                  40                  45

Phe Pro Asp Gly Val Gln Asn Trp Pro Ala Leu Ser Ile Val Val Ile
    50                  55                  60

Ile Ile Met Thr Ile Gly Gly Asn Ile Leu Val Ile Met Ala Val Ser
65              70                  75                  80

Met Glu Lys Lys Leu His Asn Ala Thr Asn Tyr Phe Leu Met Ser Leu
                85                  90                  95

Ala Ile Ala Asp Met Leu Val Gly Leu Leu Val Met Pro Leu Ser Leu
                100                 105                 110

Leu Ala Ile Leu Tyr Asp Tyr Val Trp Pro Leu Pro Arg Tyr Leu Cys
            115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Ile Arg Asn Pro
145                 150                 155                 160

Ile Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
                180                 185                 190

Ile Gly Leu Arg Asp Glu Ser Lys Val Phe Val Asn Asn Thr Thr Cys
            195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Ala Asn Met Ser Leu Asn Phe Leu Asn Cys Cys Cys Lys Lys
                260                 265                 270

Asn Gly Gly Glu Glu Glu Asn Ala Pro Asn Pro Asn Pro Asp Gln Lys
            275                 280                 285

Pro Arg Arg Lys Lys Lys Glu Lys Arg Pro Arg Gly Thr Met Gln Ala
    290                 295                 300

Ile Asn Asn Glu Lys Lys Ala Lys Lys Val Leu Gly Ile Val Phe Phe
305                 310                 315                 320

Val Phe Leu Ile Met Trp Cys Pro Phe Phe Ile Thr Asn Ile Leu Ser
                325                 330                 335

Val Leu Cys Gly Lys Ala Cys Asn Gln Lys Leu Met Glu Lys Leu Leu
                340                 345                 350

Asn Val Phe Val Trp Ile Gly Tyr Val Cys Ser Gly Ile Asn Pro Leu
            355                 360                 365

Val Tyr Thr Leu Phe Asn Lys Ile Tyr Arg Arg Ala Phe Ser Lys Tyr
```

```
                370             375             380
Leu Arg Cys Asp Tyr Lys Pro Asp Lys Lys Pro Pro Val Arg Gln Ile
385             390             395             400

Pro Arg Val Ala Ala Thr Ala Leu Ser Gly Arg Glu Leu Asn Val Asn
                405             410             415

Ile Tyr Arg His Thr Asn Glu Arg Val Ala Arg Lys Ala Asn Asp Pro
            420             425             430

Glu Pro Gly Ile Glu Met Gln Val Glu Asn Leu Glu Leu Pro Val Asn
        435             440             445

Pro Ser Asn Val Val Ser Glu Arg Ile Ser Ser Val
    450             455             460
```

(2) INFORMATION FOR SEQ ID NO: 21:

(i) SEQUENCE CHARACTERISTICS:
        (A) LENGTH: 2246 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

```
GGCGCTCTGG TGCTCACTGA GGAAGCTTCC TTAGGTGTAC CGATCTTAAT GATTGAGCCC     60

TTGGAGCAGC AAGATTGTTA ATCTTGGTTG CTCCTTTGGC CTGTCTATCC CTTACCTTCC    120

TATTACATAT GAACTTTTCT TCGTTCTGCA CATCGATTGT CGTCGGCGTC GTGGAGATCG    180

TCGTGGTGCT CCGGTGGTGG TCTTCGTCCG CTTAGAATAG TGTAGTTAGT TAGGGGCCTT    240

CAAAGAAGAA AGAAGAAGCG ATTGGCGCGG AGAGATGCTG GAGGTGTCAG TTTCTATGCT    300

AGAGTAGGGT AGTGAAACAA TCCCCAGCCA AACCTTTCCG GGGGCGCAG GTTGCCCACA    360

GGAGGTCGAC TTGCCGGCGC TGTCCTTCGC GCCGAGCTCC CTCCATCCTT CTTTCCGTCT    420

GCTGAGACGC AAGGTTGCGG CGCGCACGCT GAGCAGCGCA CTGACTGCCG CGGGCTCCGC    480

TGGGCGATTG CAGCCGAGTC CGTTTCTCGT CTAGCTGCCG CCGCGGCGAC CTGCCTGGTC    540

TTCCTCCCGG ACGCTAGCGG GTTGTCAACT ATTACCTGCA AGCATAGGCC AACGAACACC    600

TTCTTTCCAA ATTAATTGGA ATGAAACAAT TCTGTTAACT TCCTAATTCT CAGTTTGAAA    660

CTCTGGTTGC TTAAGCCTGA AGCAATCATG GTGAACCTTG GCAACGCGGT GCGCTCGCTC    720

CTGATGCACC TAATCGGCCT ATTGGTTTGG CAATTCGATA TTTCCATAAG TCCAGTAGCA    780

GCTATAGTAA CTGACACTTT TAATTCCTCC GATGGTGGAC GCTTGTTTCA ATTCCCGGAC    840

GGGGTACAAA ACTGGCCAGC ACTTTCAATC GTCGTGATTA TAATCATGAC AATAGGGGGC    900

AACATTCTTG TTATCATGGC AGTAAGCATG GAGAAGAAAC TGCACAATGC AACCAATTAC    960

TTCTTAATGT CCCTAGCCAT TGCTGATATG CTGGTGGGAC TACTTGTCAT GCCCCTGTCC   1020

CTGCTTGCTA TTCTTTATGA TTATGTCTGG CCTTTACCTA GATATTTGTG CCCCGTCTGG   1080

ATTTCACTAG ATGTGCTATT TTCAACTGCG TCCATCATGC ACCTCTGCGC CATATCGCTG   1140

GACCGGTATG TAGCAATACG TAATCCTATT GAGCATAGCC GGTTCAATTC GCGGACTAAG   1200

GCCATCATGA AGATTGCCAT CGTTTGGGCA ATATCAATAG GAGTTTCAGT TCCTATCCCT   1260

GTGATTGGAC TGAGGGACGA AAGCAAAGTG TTCGTGAATA ACACCACGTG CGTGCTCAAT   1320

GACCCCAACT TCGTTCTCAT CGGGTCCTTC GTGGCATTCT TCATCCCGTT GACGATTATG   1380

GTGATCACCT ACTTCTTAAC GATCTACGTC CTGCGCCGTC AAACTCTGAT GTTACTTCGA   1440

GGTCACACCG AGGAGGAACT GGCTAATATG AGCCTGAACT TTCTGAACTG CTGCTGCAAG   1500
```

```
AAGAATGGTG GTGAGGAAGA GAACGCTCCG AACCCTAATC CAGATCAGAA ACCACGTCGA    1560

AAGAAGAAAG AAAAGCGTCC CAGAGGCACC ATGCAAGCTA TCAACAACGA AAAGAAAGCT    1620

AAGAAAGTCC TTGGCATTGT ATTCTTTGTG TTTCTGATCA TGTGGTGCCC GTTTTTCATC    1680

ACCAATATCC TGTCGGTTCT TTGTGGGAAG GCCTGTAACC AAAAGCTAAT GGAGAAGCTT    1740

CTCAATGTGT TTGTGTGGAT TGGCTATGTG TGTTCAGGCA TCAATCCTCT GGTGTACACT    1800

CTCTTTAATA AAATTTACCG AAGGGCTTTC TCTAAATATT TGCGCTGCGA TTATAAGCCA    1860

GACAAAAAGC CTCCTGTTCG ACAGATTCCT AGGGTTGCTG CCACTGCTTT GTCTGGGAGG    1920

GAGCTCAATG TTAACATTTA TCGGCATACC AATGAACGTG TGGCTAGGAA AGCTAATGAC    1980

CCTGAGCCTG GCATAGAGAT GCAGGTGGAG AACTTAGAGC TGCCAGTCAA CCCCTCTAAT    2040

GTGGTCAGCG AGAGGATTAG TAGTGTGTAA GCGAAGAGCA GCGCAGACTT CCTACAGGAA    2100

AGTTCCTGTA GGAAAGTCCT CCCCACCCCC CGTGATTTTC CTGTGAATCA TAACTAATGT    2160

AAATATTGCT GTGTGACAAG ACAGTGTTTT TATAAATAGC TTTGCAACCC TGTACTTTAC    2220

ATCATGCGTT AATAGTGAGA TTCGGG                                        2246
```

(2) INFORMATION FOR SEQ ID NO: 22:

(i) SEQUENCE CHARACTERISTICS:
        (A) LENGTH: 2246 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

```
GGCGCTCTGG TGCTCACTGA GGAAGCTTCC TTAGGTGTAC CGATCTTAAT GATTGAGCCC      60

TTGGAGCAGC AAGATTGTTA ATCTTGGTTG CTCCTTTGGC CTGTCTATCC CTTACCTTCC     120

TATTACATAT GAACTTTTCT TCGTTCTGCA CATCGATTGT CGTCGGCGTC GTGGAGATCG     180

TCGTGGTGCT CCGGTGGTGG TCTTCGTCCG CTTAGAATAG TGTAGTTAGT TAGGGGCCTT     240

CAAAGAAGAA AGAAGAAGCG ATTGGCGCGG AGAGATGCTG GAGGTGTCAG TTTCTATGCT     300

AGAGTAGGGT AGTGAAACAA TCCCCAGCCA AACCTTTCCG GGGGGCGCAG GTTGCCCACA     360

GGAGGTCGAC TTGCCGGCGC TGTCCTTCGC GCCGAGCTCC CTCCATCCTT CTTTCCGTCT     420

GCTGAGACGC AAGGTTGCGG CGCGCACGCT GAGCAGCGCA CTGACTGCCG CGGGCTCCGC     480

TGGGCGATTG CAGCCGAGTC CGTTTCTCGT CTAGCTGCCG CCGCGGCGAC CTGCCTGGTC     540

TTCCTCCCGG ACGCTAGCGG GTTGTCAACT ATTACCTGCA AGCATAGGCC AACGAACACC     600

TTCTTTCCAA ATTAATTGGA ATGAAACAAT TCTGTTAACT TCCTAATTCT CAGTTTGAAA     660

CTCTGGTTGC TTAAGCCTGA AGCAATCATG GTGAACCTTG GCAACGCGGT GCGCTCGCTC     720

CTGATGCACC TAATCGGCCT ATTGGTTTGG CAATTCGATA TTTCCATAAG TCCAGTAGCA     780

GCTATAGTAA CTGACACTTT TAATTCCTCC GATGGTGGAC GCTTGTTTCA ATTCCCGGAC     840

GGGGTACAAA ACTGGCCAGC ACTTTCAATC GTCGTGATTA TAATCATGAC AATAGGGGGC     900

AACATTCTTG TTATCATGGC AGTAAGCATG GAGAAGAAAC TGCACAATGC AACCAATTAC     960

TTCTTAATGT CCCTAGCCAT TGCTGATATG CTGGTGGGAC TACTTGTCAT GCCCCTGTCC    1020

CTGCTTGCTA TTCTTTATGA TTATGTCTGG CCTTTACCTA GATATTTGTG CCCCGTCTGG    1080

ATTTCACTAG ATGTGCTATT TTCAACTGCG TCCATCATGC ACCTCTGCGC CATATCGCTG    1140

GACCGGTATG TAGCAATACG TAATCCTATT GAGCATAGCC GGTTCAATTC GCGGACTAAG    1200
```

```
GCCATCATGA AGATTGCCAT CGTTTGGGCA ATATCAATAG GAGTTTCAGT TCCTATCCCT    1260

GTGATTGGAC TGAGGGACGA AAGCAAAGTG TTCGTGAATA ACACCACGTG CGTGCTCAAT    1320

GACCCCAACT TCGTTCTCAT CGGGTCCTTC GTGGCATTCT TCATCCCGTT GACGATTATG    1380

GTGATCACCT ACTTCTTAAC GATCTACGTC CTGCGCCGTC AAACTCTGAT GTTACTTCGA    1440

GGTCACACCG AGGAGGAACT GGCTAATATG AGCCTGAACT TTCTGAACTG CTGCTGCAAG    1500

AAGAATGGTG GTGAGGAAGA GAACGCTCCG AACCCTAATC CAGATCAGAA ACCACGTCGA    1560

AAGAAGAAAG AAAAGCGTCC CAGAGGCACC ATGCAAGCTA TCAACAACGA AAAGAAAGCT    1620

AAGAAAGTAC TTGGCATTGT ATTCTTTGTG TTTCTGATCA TGTGGTGCCC GTTTTTCATC    1680

ACCAATATCC TGTCGGTTCT TTGTGGGAAG GCCTGTAACC AAAAGCTAAT GGAGAAGCTT    1740

CTCAATGTGT TTGTGTGGAT TGGCTATGTG TGTTCAGGCA TCAATCCTCT GGTGTACACT    1800

CTCTTTAATA AAATTTACCG AAGGGCTTTC TCTAAATATT TGCGCTGCGA TTATAAGCCA    1860

GACAAAAAGC CTCCTGTTCG ACAGATTCCT AGGGTTGCTG CCACTGCTTT GTCTGGGAGG    1920

GAGCTCAATG TTAACATTTA TCGGCATACC AATGAACGTG TGGCTAGGAA AGCTAATGAC    1980

CCTGAGCCTG GCATAGAGAT GCAGGTGGAG AACTTAGAGC TGCCAGTCAA CCCCTCTAAT    2040

GTGGTCAGCG AGAGGATTAG TAGTGTGTAA GCGAAGAGCA GCGCAGACTT CCTACAGGAA    2100

AGTTCCTGTA GGAAAGTCCT CCCCACCCCC CGTGATTTTC CTGTGAATCA TAACTAATGT    2160

AAATATTGCT GTGTGACAAG ACAGTGTTTT TATAAATAGC TTTGCAACCC TGTACTTTAC    2220

ATCATGCGTT AATAGTGAGA TTCGGG                                         2246

(2) INFORMATION FOR SEQ ID NO: 23:

(i) SEQUENCE CHARACTERISTICS:
        (A) LENGTH: 460 amino acids
        (B) TYPE: amino acid
        (C) STRANDEDNESS:
        (D) TOPOLOGY: Not Relevant (ii) MOLECULE TYPE: protein (xi) SEQUENCE DESCRIPTION: SEQ ID NO: 23:

Met Val Asn Leu Gly Asn Ala Val Arg Ser Leu Met His Leu Ile
1               5                   10                  15

Gly Leu Leu Val Trp Gln Phe Asp Ile Ser Ile Ser Pro Val Ala Ala
            20                  25                  30

Ile Val Thr Asp Thr Phe Asn Ser Ser Asp Gly Gly Arg Leu Phe Gln
        35                  40                  45

Phe Pro Asp Gly Val Gln Asn Trp Pro Ala Leu Ser Ile Val Val Ile
    50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Ile Arg Asn Pro
145                 150                 155                 160
```

```
Ile Glu His Ser Arg Phe Asn Ser Arg Thr Lys Ala Ile Met Lys Ile
            165                 170                 175
Ala Ile Val Trp Ala Ile Ser Ile Gly Val Ser Val Pro Ile Pro Val
        180                 185                 190
Ile Gly Leu Arg Asp Glu Ser Lys Val Phe Val Asn Asn Thr Thr Cys
            195                 200                 205
Val Leu Asn Asp Pro Asn Phe Val Leu Ile Gly Ser Phe Val Ala Phe
    210                 215                 220
Phe Ile Pro Leu Thr Ile Met Val Ile Thr Tyr Phe Leu Thr Ile Tyr
225                 230                 235                 240
Val Leu Arg Arg Gln Thr Leu Met Leu Leu Arg Gly His Thr Glu Glu
            245                 250                 255
Glu Leu Ala Asn Met Ser Leu Asn Phe Leu Asn Cys Cys Cys Lys Lys
            260                 265                 270
Asn Gly Gly Glu Glu Glu Asn Ala Pro Asn Pro Asn Pro Asp Gln Lys
            275                 280                 285
Pro Arg Arg Lys Lys Lys Glu Lys Arg Pro Arg Gly Thr Met Gln Ala
    290                 295                 300
Ile Asn Asn Glu Lys Lys Ala Phe Lys Val Leu Gly Ile Val Phe Phe
305                 310                 315                 320
Val Phe Leu Ile Met Trp Cys Pro Phe Phe Ile Thr Asn Ile Leu Ser
            325                 330                 335
Val Leu Cys Gly Lys Ala Cys Asn Gln Lys Leu Met Glu Lys Leu Leu
            340                 345                 350
Asn Val Phe Val Trp Ile Gly Tyr Val Cys Ser Gly Ile Asn Pro Leu
            355                 360                 365
Val Tyr Thr Leu Phe Asn Lys Ile Tyr Arg Arg Ala Phe Ser Lys Tyr
    370                 375                 380
Leu Arg Cys Asp Tyr Lys Pro Asp Lys Lys Pro Pro Val Arg Gln Ile
385                 390                 395                 400
Pro Arg Val Ala Ala Thr Ala Leu Ser Gly Arg Glu Leu Asn Val Asn
            405                 410                 415
Ile Tyr Arg His Thr Asn Glu Arg Val Ala Arg Lys Ala Asn Asp Pro
            420                 425                 430
Glu Pro Gly Ile Glu Met Gln Val Glu Asn Leu Glu Leu Pro Val Asn
            435                 440                 445
Pro Ser Asn Val Val Ser Glu Arg Ile Ser Ser Val
    450                 455                 460

(2) INFORMATION FOR SEQ ID NO: 24:

(i) SEQUENCE CHARACTERISTICS:
        (A) LENGTH: 2246 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

GGCGCTCTGG TGCTCACTGA GGAAGCTTCC TTAGGTGTAC CGATCTTAAT GATTGAGCCC      60

TTGGAGCAGC AAGATTGTTA ATCTTGGTTG CTCCTTTGGC CTGTCTATCC CTTACCTTCC    120

TATTACATAT GAACTTTTCT TCGTTCTGCA CATCGATTGT CGTCGGCGTC GTGGAGATCG    180

TCGTGGTGCT CCGGTGGTGG TCTTCGTCCG CTTAGAATAG TGTAGTTAGT TAGGGGCCTT    240
```

```
CAAAGAAGAA AGAAGAAGCG ATTGGCGCGG AGAGATGCTG GAGGTGTCAG TTTCTATGCT      300
AGAGTAGGGT AGTGAAACAA TCCCCAGCCA AACCTTTCCG GGGGGCGCAG GTTGCCCACA      360
GGAGGTCGAC TTGCCGGCGC TGTCCTTCGC GCCGAGCTCC CTCCATCCTT CTTTCCGTCT      420
GCTGAGACGC AAGGTTGCGG CGCGCACGCT GAGCAGCGCA CTGACTGCCG CGGGCTCCGC      480
TGGGCGATTG CAGCCGAGTC CGTTTCTCGT CTAGCTGCCG CCGCGGCGAC CTGCCTGGTC      540
TTCCTCCCGG ACGCTAGCGG GTTGTCAACT ATTACCTGCA AGCATAGGCC AACGAACACC      600
TTCTTTCCAA ATTAATTGGA ATGAAACAAT TCTGTTAACT TCCTAATTCT CAGTTTGAAA      660
CTCTGGTTGC TTAAGCCTGA AGCAATCATG GTGAACCTTG GCAACGCGGT GCGCTCGCTC      720
CTGATGCACC TAATCGGCCT ATTGGTTTGG CAATTCGATA TTTCCATAAG TCCAGTAGCA      780
GCTATAGTAA CTGACACTTT TAATTCCTCC GATGGTGGAC GCTTGTTTCA ATTCCCGGAC      840
GGGGTACAAA ACTGGCCAGC ACTTTCAATC GTCGTGATTA TAATCATGAC AATAGGGGGC      900
AACATTCTTG TTATCATGGC AGTAAGCATG GAGAAGAAAC TGCACAATGC AACCAATTAC      960
TTCTTAATGT CCCTAGCCAT TGCTGATATG CTGGTGGGAC TACTTGTCAT GCCCCTGTCC     1020
CTGCTTGCTA TTCTTTATGA TTATGTCTGG CCTTTACCTA GATATTTGTG CCCCGTCTGG     1080
ATTTCACTAG ATGTGCTATT TTCAACTGCG TCCATCATGC ACCTCTGCGC CATATCGCTG     1140
GACCGGTATG TAGCAATACG TAATCCTATT GAGCATAGCC GGTTCAATTC GCGGACTAAG     1200
GCCATCATGA AGATTGCCAT CGTTTGGGCA ATATCAATAG GAGTTTCAGT TCCTATCCCT     1260
GTGATTGGAC TGAGGGACGA AAGCAAAGTG TTCGTGAATA ACACCACGTG CGTGCTCAAT     1320
GACCCCAACT TCGTTCTCAT CGGGTCCTTC GTGGCATTCT TCATCCCGTT GACGATTATG     1380
GTGATCACCT ACTTCTTAAC GATCTACGTC CTGCGCCGTC AAACTCTGAT GTTACTTCGA     1440
GGTCACACCG AGGAGGAACT GGCTAATATG AGCCTGAACT TTCTGAACTG CTGCTGCAAG     1500
AAGAATGGTG GTGAGGAAGA GAACGCTCCG AACCCTAATC CAGATCAGAA ACCACGTCGA     1560
AAGAAGAAAG AAAAGCGTCC CAGAGGCACC ATGCAAGCTA TCAACAACGA AAAGAAAGCT     1620
TTCAAAGTCC TTGGCATTGT ATTCTTTGTG TTTCTGATCA TGTGGTGCCC GTTTTTCATC     1680
ACCAATATCC TGTCGGTTCT TTGTGGGAAG GCCTGTAACC AAAAGCTAAT GGAGAAGCTT     1740
CTCAATGTGT TTGTGTGGAT TGGCTATGTG TGTTCAGGCA TCAATCCTCT GGTGTACACT     1800
CTCTTTAATA AAATTTACCG AAGGGCTTTC TCTAAATATT TGCGCTGCGA TTATAAGCCA     1860
GACAAAAAGC CTCCTGTTCG ACAGATTCCT AGGGTTGCTG CCACTGCTTT GTCTGGGAGG     1920
GAGCTCAATG TTAACATTTA TCGGCATACC AATGAACGTG TGGCTAGGAA AGCTAATGAC     1980
CCTGAGCCTG GCATAGAGAT GCAGGTGGAG AACTTAGAGC TGCCAGTCAA CCCCTCTAAT     2040
GTGGTCAGCG AGAGGATTAG TAGTGTGTAA GCGAAGAGCA GCGCAGACTT CCTACAGGAA     2100
AGTTCCTGTA GGAAAGTCCT CCCCACCCCC CGTGATTTTC CTGTGAATCA TAACTAATGT     2160
AAATATTGCT GTGTGACAAG ACAGTGTTTT TATAAATAGC TTTGCAACCC TGTACTTTAC     2220
ATCATGCGTT AATAGTGAGA TTCGGG                                         2246
```

(2) INFORMATION FOR SEQ ID NO: 25:

(i) SEQUENCE CHARACTERISTICS:
        (A) LENGTH: 2246 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

```
GGCGCTCTGG TGCTCACTGA GGAAGCTTCC TTAGGTGTAC CGATCTTAAT GATTGAGCCC      60
TTGGAGCAGC AAGATTGTTA ATCTTGGTTG CTCCTTTGGC CTGTCTATCC CTTACCTTCC     120
TATTACATAT GAACTTTTCT TCGTTCTGCA CATCGATTGT CGTCGGCGTC GTGGAGATCG     180
TCGTGGTGCT CCGGTGGTGG TCTTCGTCCG CTTAGAATAG TGTAGTTAGT TAGGGGCCTT     240
CAAAGAAGAA AGAAGAAGCG ATTGGCGCGG AGAGATGCTG GAGGTGTCAG TTTCTATGCT     300
AGAGTAGGGT AGTGAAACAA TCCCCAGCCA AACCTTTCCG GGGGGCGCAG GTTGCCCACA     360
GGAGGTCGAC TTGCCGGCGC TGTCCTTCGC GCCGAGCTCC CTCCATCCTT CTTTCCGTCT     420
GCTGAGACGC AAGGTTGCGG CGCGCACGCT GAGCAGCGCA CTGACTGCCG CGGGCTCCGC     480
TGGGCGATTG CAGCCGAGTC CGTTTCTCGT CTAGCTGCCG CCGCGGCGAC CTGCCTGGTC     540
TTCCTCCCGG ACGCTAGCGG GTTGTCAACT ATTACCTGCA AGCATAGGCC AACGAACACC     600
TTCTTTCCAA ATTAATTGGA ATGAAACAAT TCTGTTAACT TCCTAATTCT CAGTTTGAAA     660
CTCTGGTTGC TTAAGCCTGA AGCAATCATG GTGAACCTTG GCAACGCGGT GCGCTCGCTC     720
CTGATGCACC TAATCGGCCT ATTGGTTTGG CAATTCGATA TTTCCATAAG TCCAGTAGCA     780
GCTATAGTAA CTGACACTTT TAATTCCTCC GATGGTGGAC GCTTGTTTCA ATTCCCGGAC     840
GGGGTACAAA ACTGGCCAGC ACTTTCAATC GTCGTGATTA AATCATGAC AATAGGGGGC     900
AACATTCTTG TTATCATGGC AGTAAGCATG GAGAAGAAAC TGCACAATGC AACCAATTAC     960
TTCTTAATGT CCCTAGCCAT TGCTGATATG CTGGTGGGAC TACTTGTCAT GCCCCTGTCC    1020
CTGCTTGCTA TTCTTTATGA TTATGTCTGG CCTTTACCTA GATATTTGTG CCCCGTCTGG    1080
ATTTCACTAG ATGTGCTATT TTCAACTGCG TCCATCATGC ACCTCTGCGC CATATCGCTG    1140
GACCGGTATG TAGCAATACG TAATCCTATT GAGCATAGCC GGTTCAATTC GCGGACTAAG    1200
GCCATCATGA AGATTGCCAT CGTTTGGGCA ATATCAAATG GAGTTTCAGT TCCTATCCCT    1260
GTGATTGGAC TGAGGGACGA AAGCAAAGTG TTCGTGAATA ACACCACGTG CGTGCTCAAT    1320
GACCCCAACT TCGTTCTCAT CGGGTCCTTC GTGGCATTCT TCATCCCGTT GACGATTATG    1380
GTGATCACCT ACTTCTTAAC GATCTACGTC CTGCGCCGTC AAACTCTGAT GTTACTTCGA    1440
GGTCACACCG AGGAGGAACT GGCTAATATG AGCCTGAACT TTCTGAACTG CTGCTGCAAG    1500
AAGAATGGTG GTGAGGAAGA GAACGCTCCG AACCCTAATC CAGATCAGAA ACCACGTCGA    1560
AAGAAGAAAG AAAAGCGTCC CAGAGGCACC ATGCAAGCTA TCAACAACGA AAAGAAAGCT    1620
TTCAAAGTAC TTGGCATTGT ATTCTTTGTG TTTCTGATCA TGTGGTGCCC GTTTTTCATC    1680
ACCAATATCC TGTCGGTTCT TTGTGGGAAG GCCTGTAACC AAAAGCTAAT GGAGAAGCTT    1740
CTCAATGTGT TTGTGTGGAT TGGCTATGTG TGTTCAGGCA TCAATCCTCT GGTGTACACT    1800
CTCTTTAATA AAATTTACCG AAGGGCTTTC TCTAAATATT TGCGCTGCGA TTATAAGCCA    1860
GACAAAAAGC CTCCTGTTCG ACAGATTCCT AGGGTTGCTG CCACTGCTTT GTCTGGGAGG    1920
GAGCTCAATG TTAACATTTA TCGGCATACC AATGAACGTG TGGCTAGGAA AGCTAATGAC    1980
CCTGAGCCTG GCATAGAGAT GCAGGTGGAG AACTTAGAGC TGCCAGTCAA CCCCTCTAAT    2040
GTGGTCAGCG AGAGGATTAG TAGTGTGTAA GCGAAGAGCA GCGCAGACTT CCTACAGGAA    2100
AGTTCCTGTA GGAAAGTCCT CCCCACCCCC CGTGATTTTC CTGTGAATCA TAACTAATGT    2160
AAATATTGCT GTGTGACAAG ACAGTGTTTT TATAAATAGC TTTGCAACCC TGTACTTTAC    2220
ATCATGCGTT AATAGTGAGA TTCGGG                                         2246
```